(12) United States Patent
Finneran et al.

(10) Patent No.: US 8,032,210 B2
(45) Date of Patent: Oct. 4, 2011

(54) EMG DIAGNOSTIC SYSTEM AND METHOD

(75) Inventors: Mark T. Finneran, Wooster, OH (US); Timothy G. Biro, Hudson, OH (US)

(73) Assignee: SpineMatrix, Inc., Cincinnati, OH (US)

( * ) Notice: Subject to any disclaimer, the term of this patent is extended or adjusted under 35 U.S.C. 154(b) by 757 days.

(21) Appl. No.: 11/539,102

(22) Filed: Oct. 5, 2006

(65) Prior Publication Data

US 2007/0167859 A1 Jul. 19, 2007

Related U.S. Application Data

(60) Provisional application No. 60/725,021, filed on Oct. 6, 2005.

(51) Int. Cl.
*A61B 5/04* (2006.01)
(52) U.S. Cl. ........................................ 600/546; 600/382
(58) Field of Classification Search .................. 600/546, 600/594, 382, 393, 595; 607/46, 100
See application file for complete search history.

(56) References Cited

U.S. PATENT DOCUMENTS

| | | | |
|---|---|---|---|
| 4,655,227 A * | 4/1987 | Gracovetsky | 600/594 |
| 4,964,411 A | 10/1990 | Johnson et al. | |
| 5,163,440 A | 11/1992 | DeLuca et al. | |
| 5,505,208 A * | 4/1996 | Toomim et al. | 600/546 |
| 5,645,073 A | 7/1997 | Kadefors et al. | |
| 5,755,675 A * | 5/1998 | Sihvonen | 600/594 |
| 6,026,321 A | 2/2000 | Miyata et al. | |
| 6,280,394 B1 | 8/2001 | Maloney et al. | |
| 6,280,395 B1 | 8/2001 | Appel et al. | |
| 6,434,420 B1 | 8/2002 | Taheri | |
| 6,434,421 B1 | 8/2002 | Taheri | |
| 6,463,322 B1 | 10/2002 | Lutz et al. | |
| 6,547,746 B1 | 4/2003 | Marino | |
| 6,584,347 B1 | 6/2003 | Sinderby | |
| 6,865,409 B2 | 3/2005 | Getsla et al. | |
| 6,920,350 B2 | 7/2005 | Xue et al. | |
| 6,965,794 B2 | 11/2005 | Brody | |

OTHER PUBLICATIONS

Reger et al. "Analysis of Large Array Surface Myoelectric Potentials for the Low Back Muscles" 2001. p. 1-4.*

* cited by examiner

*Primary Examiner* — Max Hindenburg
*Assistant Examiner* — Renee Danega
(74) *Attorney, Agent, or Firm* — Christopher L. Parmelee; Walker & Jocke

(57) ABSTRACT

A system for detecting and analyzing electrical activity in the anatomy of an organism underlying an electromyographic (EMG) sensor device provides signals corresponding to electrical activity adjacent each electrode of sensor device. A method using the system may comprise determining EMG data for a patient using the EMG sensor device. The method may further include determining whether the determined EMG data for the patient corresponds to predetermined EMG data associated with at least one of a facet condition, a disc condition, and a muscle condition.

30 Claims, 41 Drawing Sheets

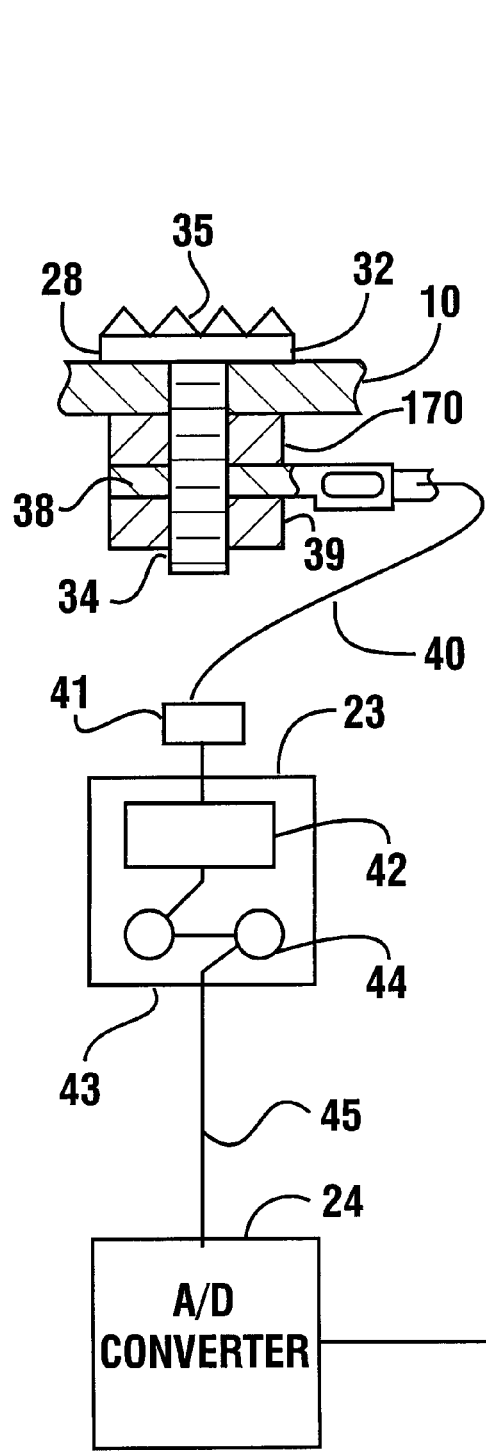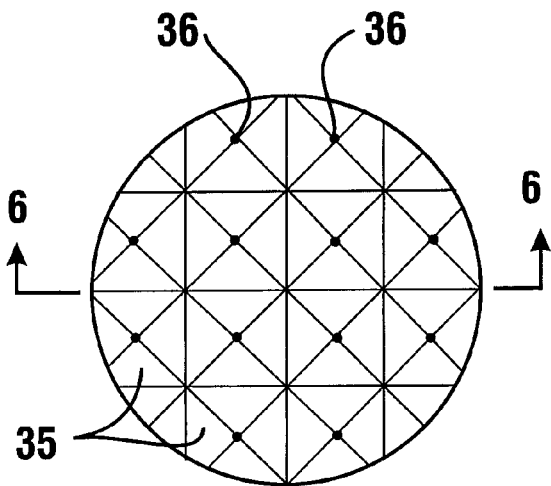
FIG. 5
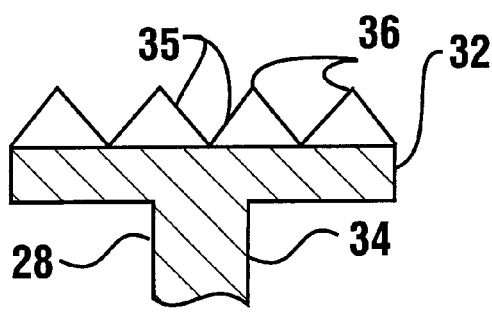
FIG. 6
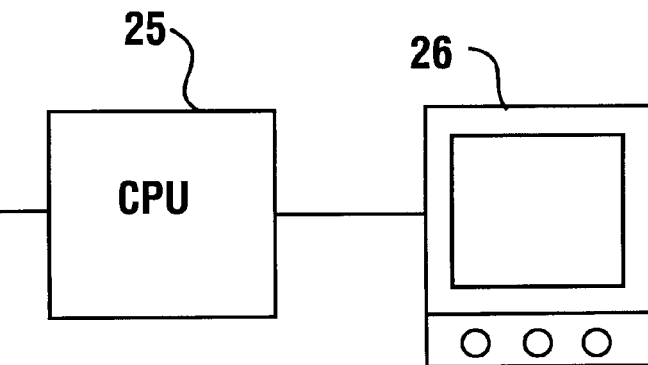
FIG. 4

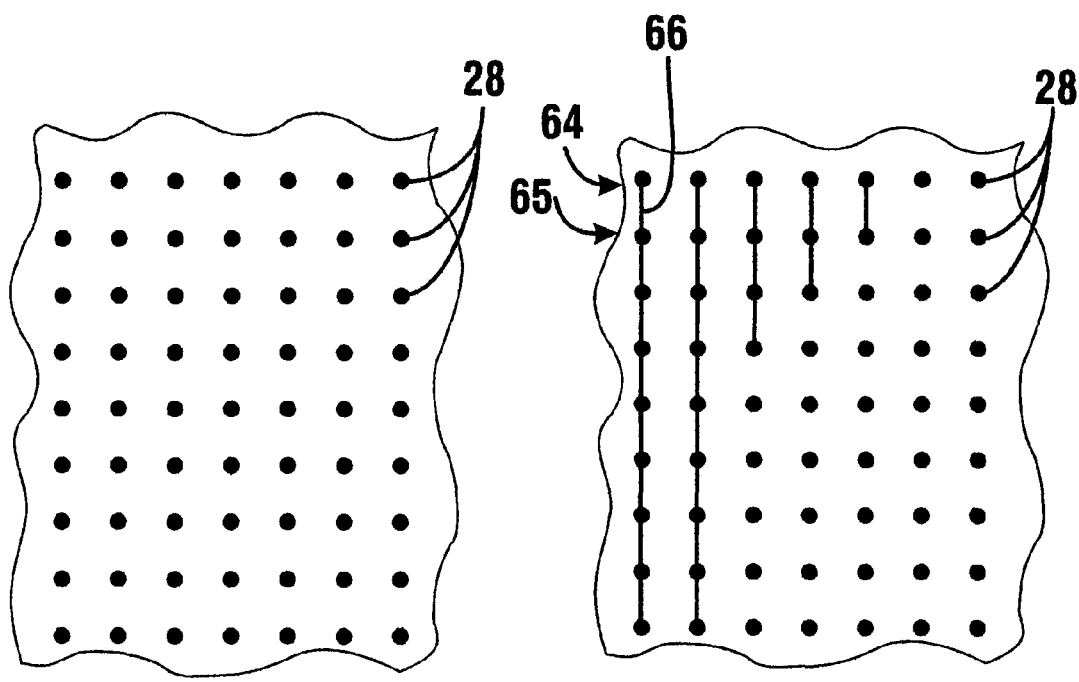
FIG. 10    FIG. 11
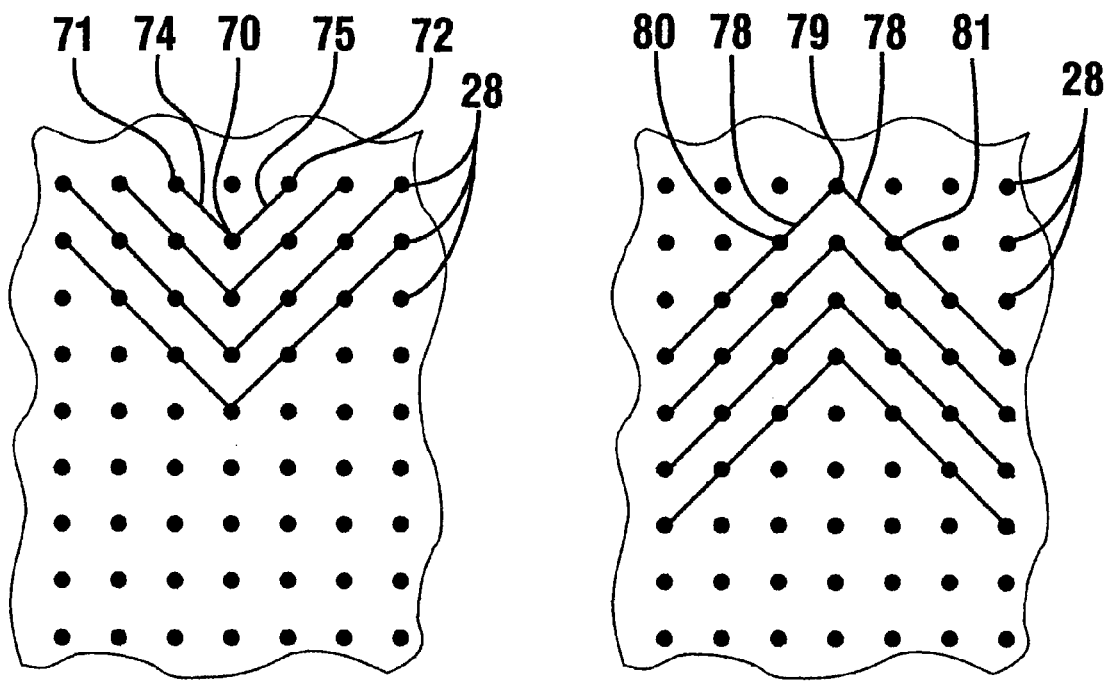
FIG. 12    FIG. 13

Software Program - Header Format (135)

Version Information: (152)

File version major
File version minor

Patient Information: (154)

Patient name
Patient initials
Age
Weight
Sex
Height (Feet and Inches)
Birth date
Current date
Comments

Pad Information: (155)

Model name
Vertical number of electrodes
Horizontal number of electrodes
Vertical electrode spacing (cm)
Horizontal electrode spacing (cm)

Calibration Information: (156)

Spinous process T-10x coordinate (pixels)
Spinous process T-10y coordinate (pixels)
Left PSIS x coordinate (pixels)
Left PSIS y coordinate (pixels)
Right PSIS x coordinate (pixels)
Right PSIS y coordinate (pixels)

Data Acquisition Settings: (157)

Number of channels scanned
Pre-amplifier gain
Analog digital board gain
Scan rate (seconds)
Scan period (seconds)
Pre-scan period (milliseconds)

Display Settings: (158)

Minimum voltage to display (display software will show voltages below this value as saturated)
Maximum voltage to display (display software will show voltages above this value as saturated)

FIG. 28

Software Program - File List

Analog-to-Digital (*A2D) Files (130)

A2D files contain the actual analog-to-digital values collected from the National Instruments hardware during a test. The files contain the header described above and the Analog-to-digital values. The structure of an A/D scan is:

<Scan 1, channel 1><Scan 1, channel 1, channel 3>...
<Scan 2, channel 1><Scan 2, channel 2, channel 3>...
Etc...

Each scan is stored in a two byte word in little endian format.

Voltage (*.DAT) Files (132)

DAT files contain the voltage data from a test, after it has been converted from A/D values to voltages and signal conditioning filters have been applied. The files contain the header described above followed by the voltage values. The Format is:

<Scan 1, channel 1><Scan 1, channel 2><Scan 1, channel 3>...
<Scan 2, channel 1><Scan 2, channel 2><Scan 2, channel 3>...
etc...

Each scan is stored as an IEEE double floating point value.

RMS (*.RMS) Files (134)

RMS files contain the RMS values of the differences between the voltage waveforms of adjacent electrodes. During display of an RMS file, the values can then be mapped to colors, and displayed as colored line segments. The files contain the header described above by the RMS information.

The RMS voltage differences is calculated for each pair of adjacent electrodes. The row and column position of each of the two electrodes are also stored.

First electrodes' row number
  First electrodes' column number
  Second electrodes' row number
  Second electrodes' column number
  RMS values The following information about the RMS values is also stored:

Minimum RMS value in scan
  Maximum RMS value in scan
  Total number of adjacent electrodes pairs

FIG. 29

Software Program
Source File Structure (160)

Document/view and visual interface: (161)

| | |
|---|---|
| PDIMFC.CPP | Main initialization of application, display of splash screen and about dialog box. |
| MAINFORM.CPP | Message handlers for main window, menu and toolbar commands |
| CHILDFORM.CPP | Message handlers for child windows (the views). |
| PDNIFCDOC.CPP | Document: handles the commands to create new RMS files open existing ones. |
| GRAPH.CPP | Document: reads RMS files and calculates the colors to display for RMS values. |
| PDINFCVIEW.CPP | View: Displays and handles user interface controls for the RMS graph display. |

Dialog popups: (162)

| | |
|---|---|
| DIALOGPATIENT. CPP | Dialog for entering patient information. |
| DIALOGCALIBRATE. CCP | Dialog for entering calibration information. |
| DIALOGDATAAQ.CPP | Dialog that allows user to launch acquisitions of data and view acquisition parameters (Scan rate, pre-amplifier gain, etc) |
| DIALOG SETTINGS. CPP | Dialog that allows editing of data acquisition and display parameters. |
| SPLASHDIALOG. CPP | Popup display of software titles and spiffy back picture. |

Data acquisition, filtering, and calculation: (163)

| | |
|---|---|
| DAQHW.CPP | Interface to National Instruments software. Sets A/D board parameters and starts data acquisition |
| READATOD.CPP | Routines for calculating RMS values, converting A/D values to voltage, and signal conditioning |
| FILTER.CPP | Filtering algorithms including high pass, low pass, and band pass with over-sampling |

Reading and writing header information and data: (164)

| | |
|---|---|
| PATIENT.CPP | Read/Write patient information. |
| CALIBRATE.CPP | Read/Write calibrate information. |
| SETTING.CPP | Read/Write settings information. |
| PAD.CPP | Read/Write pad information. |
| DATA.CPP | Read/Writa A/D scan. |

Utilities: (165)

| | |
|---|---|
| FILELIST.CPP | Routines for gathering unique descriptive file names and data files. |
| SORT.CPP | Routine for preforming heap sort. |
| COMPARE. CPP | Routine passed to sort function that handles comparison. |
| STDAFX.CPP | Includes and other preprocessor definitions. |

Bitmaps, icons, resource files: (166)

| | | |
|---|---|---|
| LEVEL1A.BMP, | LEVEL5B.BMP, | |
| LEVEL1B.BMP, | LEVEL6.BMP, | |
| LEVEL2.BMP, | LEVEL7.BMP | |
| LEVEL3.BMP, | LEVEL8.BMP | Pictures of backs for use in RMS display. |
| LEVEL4.BMP, | | |
| LEVEL5A,BMP, | BITMAP1.BMP | Pad displayed in calibration dialog. |
| | SPLASH1A.BMP | Splash screen. |
| | TOOLBAR.BMP | Toolbar used at top of main window. |

FIG. 30

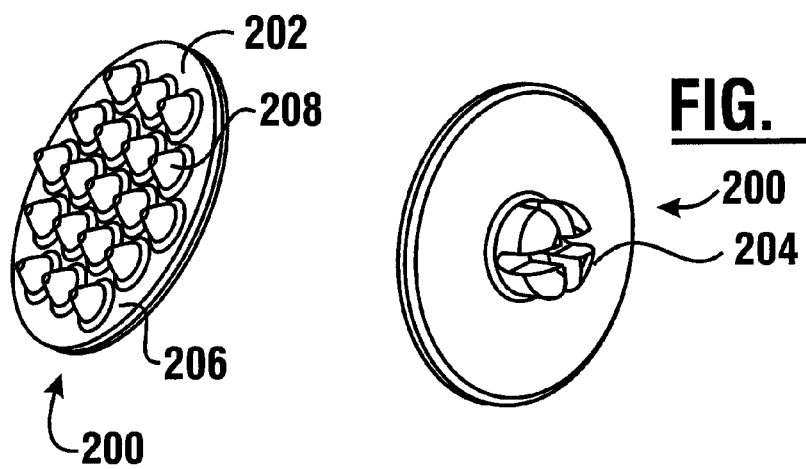
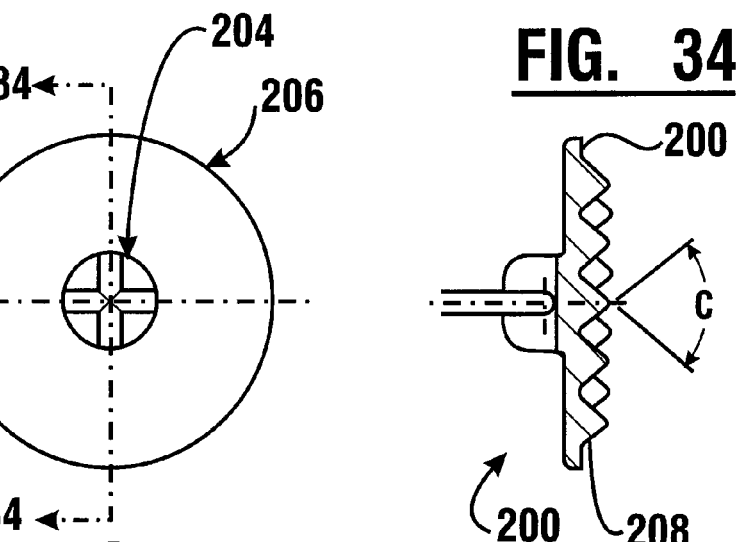
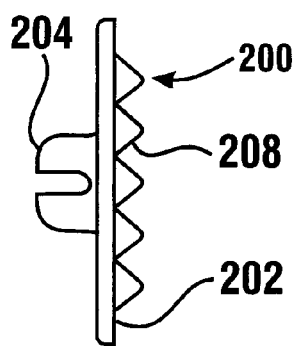
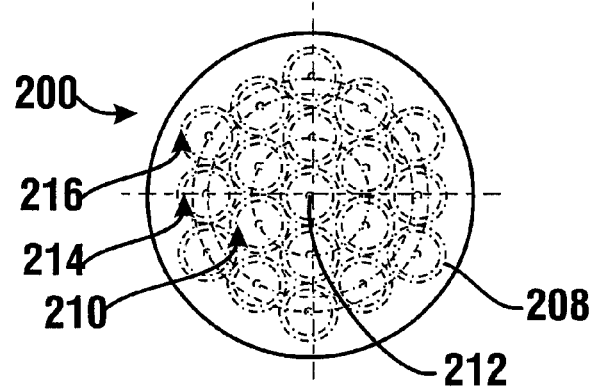

Normal Reference Ranges for Maximum RMS Values by Body Mass Index and Sex

| Position | BMI | Sex | N | Mean (SD) | Median (Interquartile Range) | Normal Reference Range |
|---|---|---|---|---|---|---|
| Upright | < 23 | Women | 38 | 18.6 (8.41) | 16.5 (13.0 to 20.7) | (8.5 to 38.8) |
|  |  | Men | 11 | 18.6 (10.23) | 17.0 (10.9 to 21.1) | (6.8 to 48.2) |
|  | 23-27 | Women | 31 | 12.8 (6.18) | 11.4 (8.2 to 15.9) | (5.4 to 28.7) |
|  |  | Men | 38 | 17.7 (6.90) | 16.3 (12.4 to 22.5) | (7.9 to 38.4) |
|  | > 27 | Women | 31 | 10.6 (4.11) | 9.5 (7.2 to 13.0) | (5.1 to 20.9) |
|  |  | Men | 33 | 14.6 (5.14) | 13.7 (10.6 to 18.5) | (7.4 to 28.0) |
| Flexion | < 23 | Women | 38 | 57.1 (29.40) | 46.8 (42.5 to 63.8) | (23.2 to 131.3) |
|  |  | Men | 11 | 67.7 (13.24) | 64.7 (56.9 to 76.3) | (47.2 to 96.4) |
|  | 23-27 | Women | 31 | 37.9 (14.44) | 34.3 (27.1 to 43.5) | (19.5 to 71.0) |
|  |  | Men | 38 | 46.6 (14.82) | 42.7 (35.3 to 56.5) | (25.0 to 84.9) |
|  | > 27 | Women | 31 | 26.4 (9.33) | 25.2 (17.9 to 33.4) | (12.5 to 54.6) |
|  |  | Men | 33 | 37.6 (12.18) | 35.6 (32.0 to 43.3) | (195 to 70.8) |
| Weighted | < 23 | All | 49 | 86.3 (39.42) | 75.5 (66.3 to 94.2) | (36.5 to 173.2) |
|  | 23-27 | All | 69 | 61.9 (27.00) | 59.6 (42.7 to 76.6) | (25.3 to 128.0) |
|  | > 27 | All | 64 | 43.6 (16.6) | 40.7 (30.8 to 53.1) | (19.2 to 86.1) |

FIG. 54

| 502 | 504 | 506 | 508 | 510 | 512 |
|---|---|---|---|---|---|
| Diagnosis | RMS | Sequence | Pattern | Balance | Co. Var. |
| Normal | IBW appropriate | Up<F<W | U, C, S, O | Balanced | < 10% |
| Muscle | Above Normal | Normal | Variable Uniformity<br>Unilateral<br>Asymmetrical<br>Organized | Unbalanced | Normal |
| Facet | Below Normal | Normal | Uniform<br>Unilateral shift<br>Organized | Balanced | >10% |
| Disc | Moderate elevation | Switched F/W | Uniform<br>Variable Symmetry<br>2D or Multifocal<br>Accommodation | Unbalanced | Variable |
| Chronic:<br>Pain-Free | Low | Normal or<br>Compressed | Uniform<br>Non-central<br>Asymmetrical<br>Disorganized<br>Accommodation | Unbalanced | Normal |
| Chronic:<br>Exacerbation | Normal | Compressed | Etiology dependant<br>History (Surgery, etc.)<br>Muscle<br>Facet<br>Disc | Unbalanced | Variable |

Legend:
IBW = Percent Ideal Body Weight
RMS = Average Maximum RMS per position
Co. Var. = Coefficient of Variation
Up = Upright
F = Flexion
W = Weighted
U = Uniform
C = Central
S = Symmetrical
O = Organized
2D = Two Dimensional Agonist Antagonist

FIG. 55  500

EMG DIAGNOSTIC SYSTEM AND METHOD

CONTINUATION DATA

This application claims benefit of U.S. Provisional Application Ser. No. 60/725,021 filed Oct. 6, 2005, which is hereby incorporated herein by reference.

TECHNICAL FIELD

An exemplary embodiment relates to a method and apparatus for monitoring and analyzing the level of muscle activity in a patient by the sensing and analysis of electromyographic signals derived from a non-invasive body surface electrode array positioned close to a muscle group. Particularly an exemplary embodiment relates to a method and system for evaluating levels of muscle activity such as muscle contraction in the back of a patient for purposes of distinguishing between different pain producing conditions.

BACKGROUND ART

Knowledge of the presence of electromyographic (EMG) signals in the muscles of humans, and the change of these signals with muscle activity, spawned development of electronic devices and techniques for monitoring those signals for the evaluation of the muscles. Human musculature, however, involves many hundreds of muscles in various muscle groups, which interact to provide skeletal support and movement. Much of the recent development has been concerned with the techniques and/or devices for monitoring the signals, analyzing the information obtained and providing reliable and useful data for the patient or treating physician.

U.S. Pat. No. 6,004,312 of Dec. 21, 1999, hereby incorporated by reference herein shows an example of a system and method for sensing and monitoring EMG signals in a patient. U.S. Pat. No. 6,745,062 of Jun. 1, 2004, hereby incorporated by reference herein shows a further example of a system and method for sensing and monitoring EMG signals using a flexible and extensible EMG electrode array placed adjacent the back of a patient.

Each of these patents shows examples of systems operative to acquire data representative of the relative level of muscle activity across a two dimensional area. These systems employ an EMG electrode array comprised of a two dimensional grid of electrodes. These electrodes are placed in adhesive contact with the patient using an electrically conductive adhesive such as hydrogel.

The electrical signals are captured from each of the electrodes in the array. In one example embodiment, to quantify the relative level of muscle activity detected for each electrode, these systems calculate a root-mean-square (RMS) voltage between each pairing of adjacent electrodes. Data representative of the calculated RMS values for adjacent electrodes may be visually displayed in a two dimensional image. Such an image can be superimposed above different muscle groups to assist in diagnosing a pain causing condition being experienced by the patient.

However, the lower back of a human patient has 48 paired symmetric muscles. Correlating the data produced from an electrode array to various combinations of the muscles in the lower back of a patient may not reveal which condition is causing pain in the lower back of the patient. Thus there exists a need for a new method and system for analyzing EMG data acquired from a patient's back for purposes of making an accurate determination as to what pain causing conditions the patient may or may not have.

DISCLOSURE OF INVENTION

An object of an exemplary embodiment is to provide a system and method for determining a pain causing condition of a patient.

A further object of an exemplary embodiment is to provide a system and method for determining a pain causing condition associated with a patient's back.

A further object of an exemplary embodiment is to provide a system and method for determining a pain causing condition associated with a patient's back using data acquired from an EMG electrode device.

Further objects of exemplary embodiments will be made apparent in the following Best Mode for Carrying Out the Invention and the appended Claims.

The electromyographic (EMG) diagnostic system of an exemplary embodiment is particularly suited for evaluation of the lower back of a human. The system may include an EMG sensor device comprised of a plurality of EMG sensors that is placed in operative connection with the back of a patient. In one embodiment the EMG sensors may include an array of EMG electrodes which are placed in contact adjacent the skin of the patient. However, in other embodiments, the EMG sensors may correspond to needles or other devices which puncture the skin. As used herein an EMG sensor device, shall be defined as any device or group of devices that are operative to detect electrical signals from a patient corresponding to a relative level of muscle activity at a plurality of positions in a two dimensional area of the patient.

The system may process the EMG signals to determine EMG data which characterizes different features associated with one or more measurements of EMG signals from a patient. The determined characterizations of the EMG data can then be correlated to predetermined characterizations associated with known back conditions. For example, different types of patterns associated with areas of elevated muscle activity across the detection area of the sensor device may be characterized. The patterns may be characterized in a manner which identifies features associated with one or more positions of electrode pair groupings of relatively higher or elevated muscle activity. Identified pattern characterizations may be compared or correlated to predetermined characterizations of patterns associated with known back conditions for purposes of identifying which of a plurality of back conditions is most likely associated with a particular patient.

For example, a facet condition such as facet joint syndrome may be identified from the presence in the detection area of a single continuous grouping of relatively higher muscle activity which transverses the vertebral column, but has a peak level of muscle activity that is laterally offset with respect to the longitudinal axis of the vertebral column. In another example, a disc condition such as discogenic low back pain may be identified from the presence in the detection area of two to three separated groupings of relatively higher muscle activity. In one example a disc condition may be indicated by the presence of three groupings of relatively higher muscle activity, where two of the groupings are located generally symmetrically on opposed sides of the spine, while a third grouping is located generally centered on the vertebral column relatively lower on the vertebral column than the first two groupings.

In one embodiment, the determination as to whether the patient is more likely associated with a facet condition, a disc condition, or another condition may be done manually. Such a manual determination may be carried out through inspection of a system generated image representative of the detection area, which image visually displays the grouping(s) of relatively higher levels of muscle activity. To determine a possible cause for back pain in the patient, the person performing the determination may attempt to visually match features of the grouping(s) identified in the image with the predetermined characterizations of groupings associated with known conditions such as a facet condition, a disc condition, or other conditions.

In another embodiment, the determination may be made through operation of a software program which evaluates the data to identify grouping(s) in the detection area and to match the identified groupings with predetermined characterization data stored in a data store for a facet condition, a disc condition, or other conditions.

In further exemplary embodiments, other EMG data determined responsive to the EMG signals may be evaluated either manually or by software when determining whether the patient has a facet condition, a disc condition, or another condition. For example, data from the detection area may be acquired and evaluated for the patient standing in different positions. Such positions may include the patient standing: in a first position with the back of the patient in a generally vertical orientation; in a second position with the back of the patient bent forward with respect to the generally vertical orientation; and in a third position with the arms of the patient held out in from of the patient while holding weights.

The EMG data associated with the different positions may then be evaluated to determine information useful for identifying a back condition. For example, such additional information may include determining from the EMG data, a maximum RMS voltage associated with each position of the patient, which is compared to normal ranges of maximum RMS voltage for patients without back conditions in the corresponding positions, of corresponding gender and/or with corresponding percent ideal body weight or body mass index.

As used herein, a "normal" back condition generally corresponds to a patient's back that does not have pain or an injury. In one embodiment, the term "acute" may correspond to a back condition in which a patient has had 6-12 weeks of pain or less, while "chronic" may correspond to back condition in which a patient has in excess of 6-12 weeks of pain. However it is to be understood that such definitions of acute and chronic may vary in the medical field, therefore alternative embodiments may not categorize a determined back condition as acute or chronic or may categorize a determined back condition as acute or chronic based on different definitions of these terms.

Also as used herein, facet joint syndrome corresponds to a facet injury and is referred to herein as a facet condition. A facet is one of many small joints in the spine. There are two facets for each vertebral level or disc level (one on the left and one on the right). Also as used herein, discongenic low back pain corresponds to a disc injury and is referred to herein as a disc condition. A disc is the ligamentous structure between two vertebral bodies. The outer ring, or annulus of the disc is designed to hold the bones together and to keep the soft central portion of the disc, the nucleus pulposis, in place. A disc condition injury may correspond to a disc that is sprained, herniated or slipped.

Other back conditions which may be diagnosed with the described exemplary embodiments may include a back muscle injury and other conditions which produce EMG data with identifying characteristics. For example an injury to one or more muscles associated with the spine is referred to herein as a muscle injury.

Other conditions that may be examined and identified using exemplary embodiments include: a "chronic pain free" condition which corresponds to a patient with chronic intermittent low back pain who is pain free at the time the person is examined; and "chronic exacerbation" which corresponds to a patient with chronic intermittent low back pain who has pain at the time of the examination.

An exemplary embodiment may include a method of analyzing EMG data to identify a back condition. Such a method may include a step of determining EMG data for a patient responsive to EMG signals detected from a detection area on a back of the patient using an EMG sensor device. In addition this described method may include determining whether the determined EMG data for the patient corresponds to predetermined EMG data associated with at least one of a facet condition and a disc condition and/or other back conditions.

An alternative exemplary embodiment may correspond to a system operative to carry out these steps. Such a system may include a processor of a computer that is operative to determine the EMG data responsive to the EMG signals. Such a system may display all or portions of the determined EMG data through a display device in operative connection with the processor. A technician may then compare the displayed EMG data for the patient to a table of predetermined sets of features of EMG data. In such a table, each set is associated with a different back condition (e.g. facet condition, disc condition, muscle condition). Thus by matching EMG data determined from the patient displayed on the output device to predetermined EMG data in the table, the technician may determine a back condition associated with the patient. In this described embodiment, the table of predetermined EMG data may be printed on a card or other object. In another exemplary embodiment, the processor may be operative to output the table through the display device.

In a further exemplary embodiment, the predetermined EMG data may be stored in a data store in operative connection with the processor. The processor may be operative to determine whether the determined EMG data for the patient corresponds to predetermined EMG data associated with at least one of a facet condition and a disc condition. The processor may than cause the display device to output which of the different back conditions was determined by the processor to correspond to the EMG data from the patient.

An alternative exemplary embodiment may include a method comprising detecting EMG signals from a detection area on a back of a patient using an EMG sensor device. This method may further include determining through operation of at least one processor, EMG data for the patient responsive to the detected EMG signals. In addition the method may include comparing the EMG data for the patient to predetermined EMG data, which correlates a plurality of back conditions to respective sets of features of EMG data. The back conditions correlated in the predetermined EMG data may include a facet condition, a disc condition, and/or other conditions such as a muscle condition. Also, this described method may include determining whether the EMG data for the patient is indicative of at least one of the facet condition, the disc condition, and/or other conditions responsive to the results of the comparing step.

This alternative exemplary embodiment may also be carried out by a system. The system may include a processor of a computer that is in operative communication with a data store. The data store may include the predetermined EMG data stored therein. The processor may be operative to carry out the described determining and comparing steps and may be operative to cause a display device to output which of the back conditions corresponds to the EMG data associated with the patient. However, it is to be understood that in alternative exemplary embodiments, a technician may carry out the comparing step to determine which of the back conditions corresponds to the EMG data determined by the system for the patient.

BRIEF DESCRIPTION OF DRAWINGS

FIG. 4 is a view partly in cross-section of a portion of the sensor pad of an exemplary embodiment, showing a single electrode and the electrical connection to the computer portion of an exemplary embodiment.

FIG. 5 is an enlarged plan view only of the single electrode shown in FIG. 4.

FIG. 6 is a cross-sectional view of a single electrode taken along the lines 6-6 of FIG. 5.

FIGS. 10-13 are schematic views of the screen of the display unit showing various configurations of color bar displays.

FIG. 28 is a chart of a portion of the software program of an exemplary embodiment, showing a header format.

FIG. 29 is a chart of a portion of the software program, showing a listing of files developed therein.

FIG. 30 is a chart of a portion of the software program, showing generally the Source File Structure.

FIG. 31 is a front isometric view of an alternative electrode configuration.

FIG. 32 is a back isometric view of the alternative electrode shown in FIG. 31.

FIG. 33 is a back plan view of the alternative electrode shown in FIG. 31.

FIG. 34 is a cross sectional view of the alternative electrode taken along line 34-34 in FIG. 33.

FIG. 35 is a side view of the alternative electrode.

FIG. 36 is a front plan view of the alternative electrode.

FIG. 54 is a table of normal reference ranges for maximum RMS voltage values by body mass index and sex.

FIG. 55 is a table of EMG data characteristics associated with different types of low back pain.

BEST MODES FOR CARRYING OUT INVENTION

Figure 1:
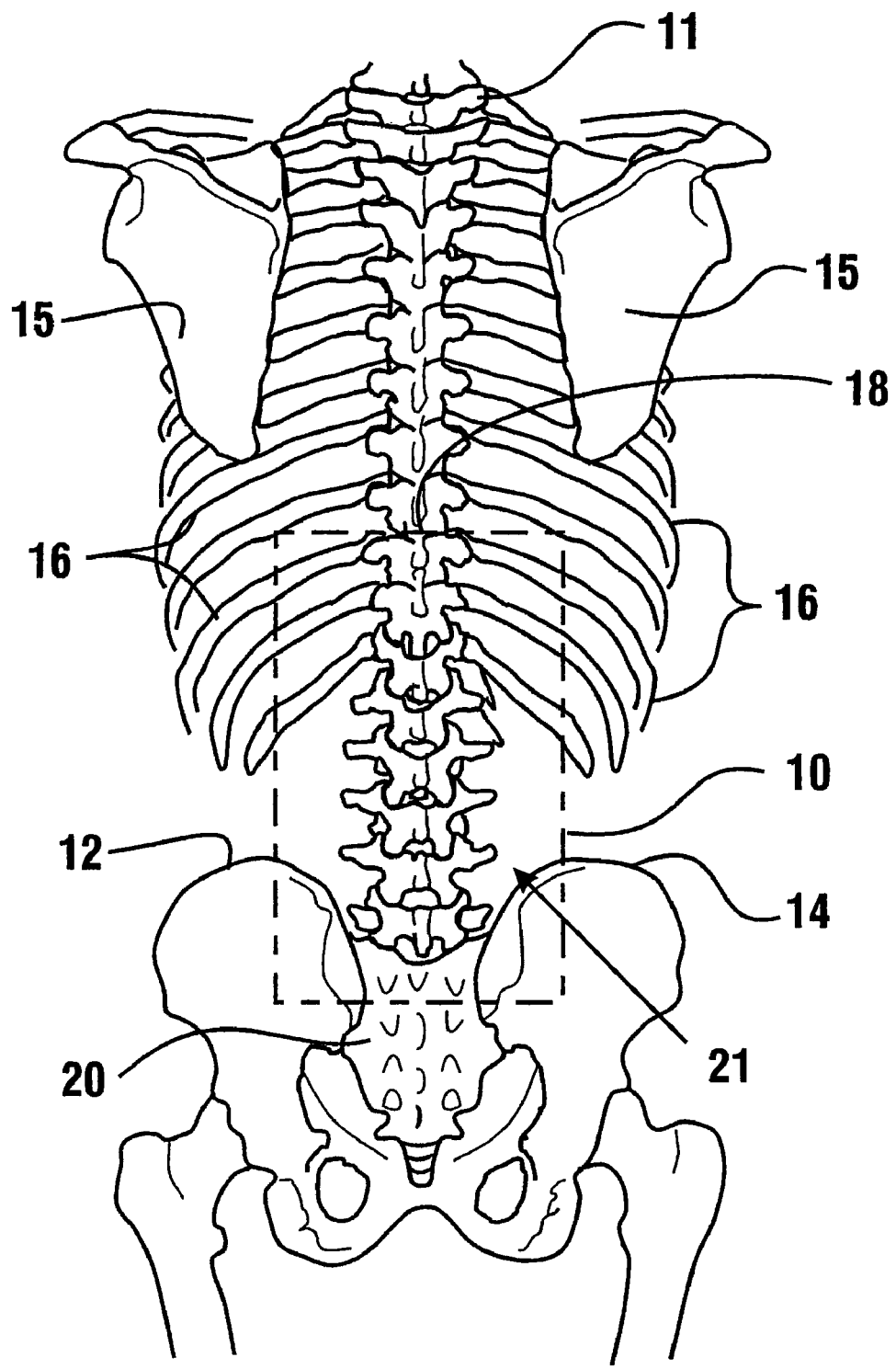
FIG. 1 is a simplified schematic overview of a portion of the lower back skeletal structure of a patient with an outline of a sensor pad depicted in position thereover.

Referring now to the drawings, and initially to FIG. 1, there is shown in schematic form of a sensor device 10 positioned in relation to a partial skeletal showing of the lower back of a patient, the latter comprising a vertebral column 11, left posterior superior iliac crest 12, right posterior superior iliac crest 14, portions of the scapula 15 and ribs 16. As will be described in greater detail hereafter, sensor device 10 is a device for collecting electromyographic (EMG) signals from the underlying muscle structure supporting and providing movement to the spine 21. As used herein the spine comprises the vertebral column 11, vertebrae, discs, facets, ligaments, muscles, muscles origins and insertions, spinal cord, spinal nerve roots, anterior spinal nerve, posterior primary ramus (PPR), medial division of PPR, and lateral division of PPR.

The muscle structure is a complicated array of muscles consisting of at least sixty-nine erector and intrinsic muscles in the thoracolumbosacral spine extending from about the tenth thoracic vertebrae 18 to the sacrum 20. These are the primary muscles with which exemplary embodiments are concerned and occur in layers from deep to superficial. Also formed in the superficial region of the lower back are several muscles which are not classical erector muscles. These latter muscles may also produce EMG signals which serve to complicate the evaluation process and may require discrimination, but which are not a primary source of the lower back pain syndrome affecting the greater portion of the patient population.

EMG signals and their relation to muscle functions are well understood at the current state of investigations. Muscles are controlled by nerves, the latter transmitting an electrical signal to a particular muscle and causing contraction thereof. The muscle itself is a volume conductor reacting to the signal of the associated nerve. There is a voltage change that occurs when a muscle contracts creating an electric potential that is directly proportional to the strength of contraction and that can be captured from the external surface area of the patient, in this instance being the surface area of the thoracolumbosacral spine.

Figure 2:
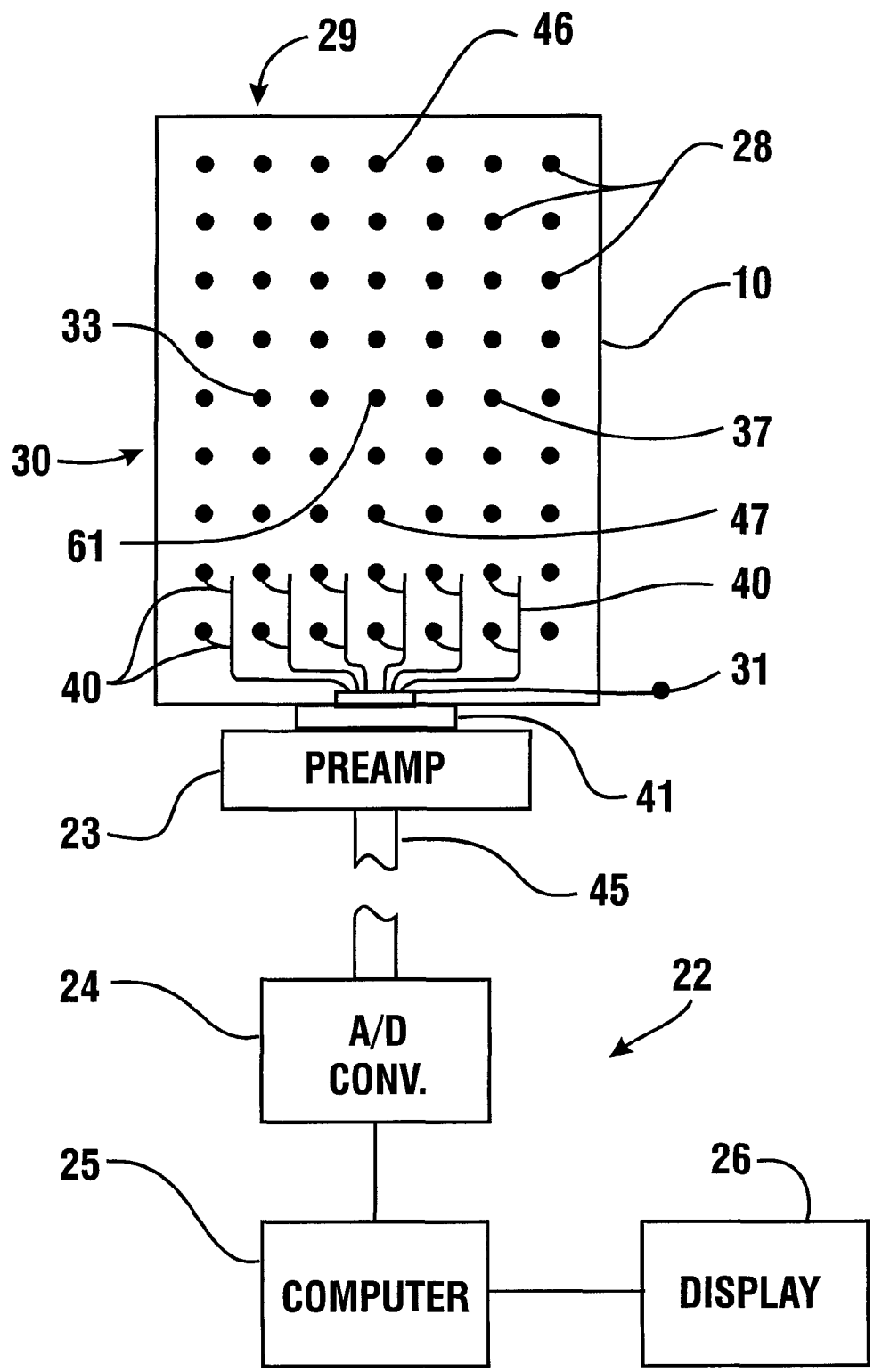
FIG. 2 is a schematic view of an exemplary embodiment, comprising the sensor pad in connection with electronic apparatus including a computer and display unit.

Referring now to FIG. 2 there is shown in schematic form, elements of an example EMG diagnositc system, comprising an EMG sensor device 101 and electronic apparatus 22 comprising preamplifier 23, converter 24, computer 25 and display unit 26. EMG sensor device 101 in one embodiment may correspond to a sensor pad comprised of a flat rectangular piece of siliconized rubber, approximately 0.157 cm (0.062 inch) thick, measuring about 30.48×30.48 cm (12×12 inches) and with a Durometer hardness on the order of 20 to 40.

The sensor pad 101 may further comprise an array of sixty-three electrodes 28, which may be made of 316 L stainless steel, silver or other materials. Electrodes 28 may be arranged in a 7×9 pattern, with the electrodes in each row and column being spaced 2.95 cm (1.162 inches) apart on center. A central column 29 of nine electrodes 28 is located in the middle of sensor pad to overlay the spine of the patient, and three equally spaced parallel columns of nine electrodes each are positioned on either side of the central column 29. Similarly, a central row 30 of seven electrodes 28 is positioned near the center of sensor pad 10, and four parallel rows of seven electrodes each are positioned on either side of central row 30. Ground electrode 31, may be a standard electrode preferably positioned on a wrist of the patient. Of course in other embodiments other configurations may be used.

In this described embodiment, all of the electrodes 28, may be identical and one configuration is shown in greater detail in FIGS. 4-6 as comprising a pyramidal tipped, bolt-shaped structure having a head 32 and integral threaded shaft 34. The head 32 is circular and includes a plurality of pyramids 35 distributed substantially evenly and projecting outwardly of the upper surface of head 32 to form the patient-contacting surface of electrode 28. The head 32 may be about 0.95 cm (0.375 inches) in diameter and have a thickness of about 0.20 cm (0.08 inches) from the lower surface thereof at the junction with shaft 34, to the tips 36 of pyramids 35. Pyramids 35 are formed by grinding electrode head 32 in a series of parallel and orthogonal passes or by electromachining to produce a square pyramidal shape having an altitude of about 0.107 cm (0.042 inches), an angle of about 90 degrees between opposing pyramid faces and culminating in a tip 36 having a radius of about 0.0127 cm (0.005 inch). Tips 36 are spaced about 0.2387 cm (0.094 inches) from one another and in this embodiment, result in an electrode 28 having twelve pyramids 35 and tips 36 at the signal-collecting surface thereof. It has been determined that this configuration of electrode 28 is useful in enhancing lower contact resistance when placed in position on a patient, thereby assuring better EMG signal reception and greater accuracy of the measurement.

In this described embodiment, each electrode 28 is mounted in an aperture in sensor pad 101 and retained in position by a nut 170 threaded to shaft 34. Alternatively, electrode 28 may have an unthreaded shaft 34 and be retained in position by a push connector. A solderless ring connector 38 is also received on shaft 34 and is firmly secured by outer nut 39 to provide an electrical interconnection with the signal gathering surface of electrode 28. An electrode wire 40 is crimped to connector 38 and each of the electrode wires 40 is routed over the surface of sensor pad 10 to a pigtail at the upper end of sensor pad 10 which terminates at a connector 41. Each electrode wire 40 is preferably a 30 gauge, multi strand, flexible copper wire which allows for some deformation of sensor pad 10 to conform to the lower back of a patient, while connector 41 allows for releasable connection of the sensor pad to the electrical circuitry to facilitate substitution of components of the apparatus. With an electrode head 32 diameter and spacing, as mentioned in the described embodiment, the edge to edge spacing of electrodes 28 in each column 29 and row 30 is about 2.0 cm (0.79 inches). This has been determined to provide enough distance between electrodes 28 to result in a meaningful signal difference between electrodes. Electrode 28 may also be used in connection with the reusable or disposable self adhesive sensor pads which are later discussed in detail.

An alternative electrode 200 used in connection with embodiments of the EMG diagnostic system of are shown in FIGS. 31-36. Electrode 200 includes a head portion 202 and a stem portion 204. The stem portion is suitable for electrical connection with electrode wires in a manner similar to the previously described embodiment.

The head portion of the electrode 200 includes a base surface 206 and a plurality of conical projections 208 extending forward therefrom. The conical projections 208 in one exemplary embodiment are comprised of nested circular arrangements of six cones each. A first set 210 of six cones is spaced in close relation about a central projection 212. A second set 214 of six cones is spaced in outward nested relation relative to the first set 210. A third set 216 is disposed outwardly relative to the second set 214. Each of the cones in the third set 216 are spaced in nested relation between cones in the second set. In the exemplary embodiment, each of the cones are arranged concentrically about the central projection 212 as shown in FIG. 36.

In one embodiment of the alternative electrode 200 the base surface is approximately 1.066 cm (0.420 inches) in diameter and the stem portion is approximately 0.318 cm (0.125 inches) in diameter. In this embodiment the first set of conical projections is spaced in a circle of about 0.391 cm (0.154 inches) in diameter. The second set of six cones is spaced on a circle about 0.678 cm (0.267 inches) in diameter and the third set of cones is spaced on a circle about 0.782 cm (0.308 inches) in diameter. Of course in other embodiments other configurations may be used.

The exemplary configuration of the conical projections provides for the projections to extend about 0.071 cm (0.028 inches) above the base surface. The incident angles of the walls bounding the cone extend at an angle C as shown in FIG. 34 which is about 79 degrees. The tips of the cones are rounded and have radii of about 0.0127 cm (0.005 inches). The thickness of the electrode 200 underlying the base surface is generally about 0.053 cm (0.021 inches). Of course in other embodiments other configurations may be used.

In the exemplary form of alternative electrode 200 the electrode is comprised of an ABS carbon-composite resin material. The ABS resin is preferably provided with a coating of a suitable conductive material which in the exemplary form of the electrode is a silver/silver chloride material. The coating is preferably deposited on the ABS resin body by electro-plating, vacuum metalization or similar processes. In alternative embodiments other approaches may be used.

A useful aspect of the described embodiment of the alternative electrode 200 is that the plated electrode contacts the patient's skin with a material that has a minimal electrolytic reaction with the skin of the patient. This minimizes the electrolytic currents which are produced as a result of contact and produces improved signals. In addition the arrangement of nested conical surfaces provides a relatively larger surface area for contact with the skin. The conical projections extend inward relative to the normal contour of the skin to provide signal acquisition from this area. This further enhances the ability of the electrode to acquire signals produced by the underlying anatomy. The structure of the exemplary form of the alternative electrode is also economical and may be produced using cost effective manufacturing processes. Further the exemplary form of the electrode provides an attractive and ornamental design.

The electronic circuitry comprising preamplifier 23 is located near sensor pad 101 for conditioning and amplifying the signals received at electrodes 28. Electrode wire 40 is connected to buffer amplifier 42, and the signal in turn is routed to low pass filter 43 and high pass filter 44 for each electrode 28 of sensor pad 10. Conditioning of the signals preferably occurs closely adjacent the patient and avoids remote transmission of very low level signals in a background of randomly generated noise signals. Buffer amplifier 42 minimizes leakage current through the electrode and errors due to electrode impedance changes. High pass filter 44 serves as an anti-aliasing filter, and low pass filter 43 prevents saturation of analog to digital (A/D) converter 24 by offset voltages, such filters being well understood in the art.

Figure 24:
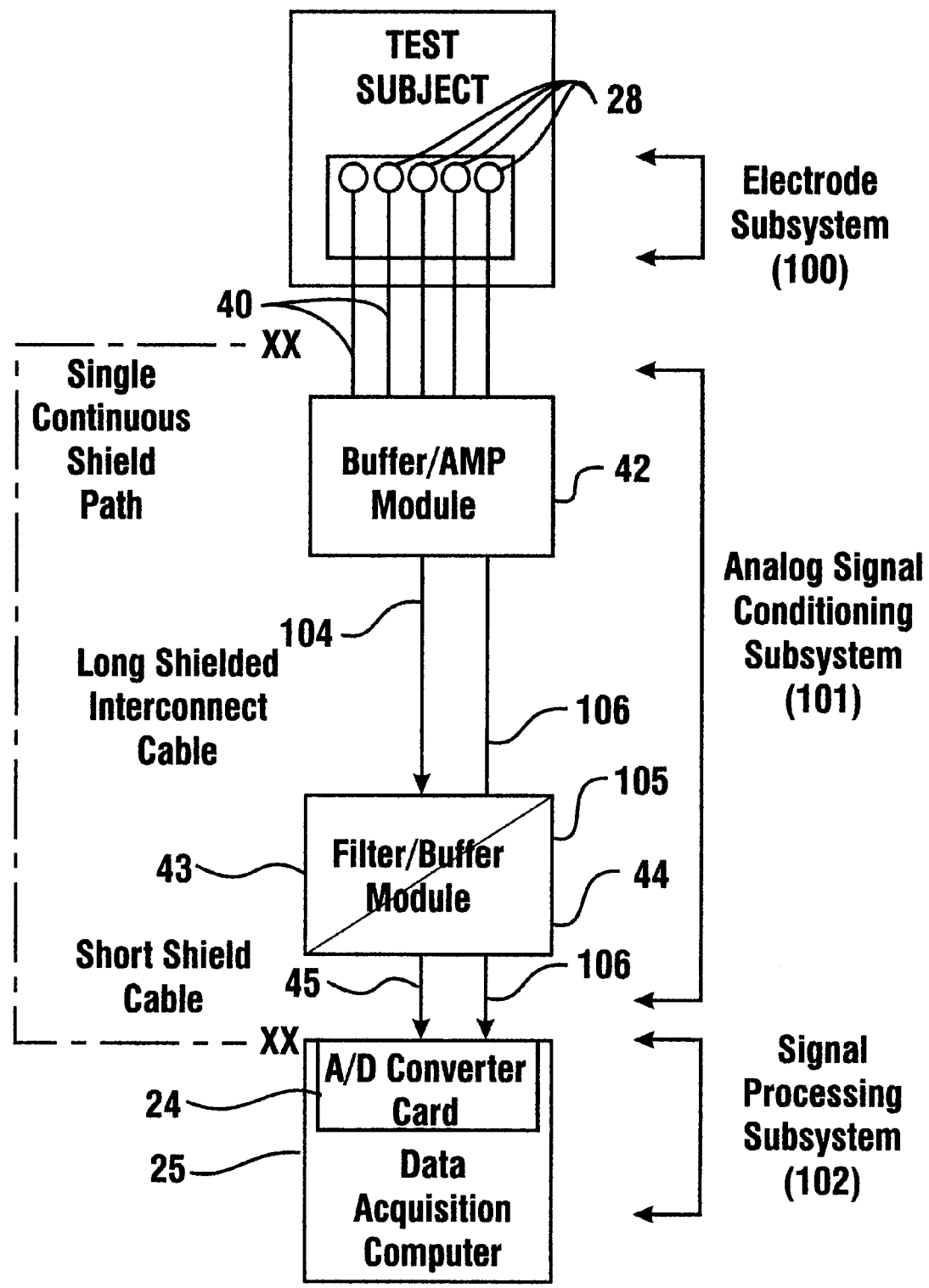
FIG. 24 is a schematic view of an exemplary embodiment, similar to that of FIGS. 2 and 4, in a modified showing of the interrelation of components.

As shown in FIG. 24 preamplifier 23 includes Buffer/Amplifier module 42 and Filter/Buffer module 105. Cable 45 connects the components of preamplifier 23 to analog to digital (A/D) converter 24 for transmission of the electrode signals for further processing and analysis.

Sensor pad 101 is applied to the back of a patient by orienting certain of the electrodes 28 to the skeletal structure of the patient. In one embodiment central electrode in the top row of electrode rows 30, i.e., electrode 46 is located over the spinous process of the tenth thoracic vertebrae 18. Two other landmarks are identified in a similar manner as the sensor pad 10 overlays the mid portion of the posterior superior iliac crest (PSIS). For example, the second and sixth electrodes 33, 37 respectively, in the center row of electrode rows 30 may be over the left PSIS and right PSIS. Alternatively, other landmarks may be used, such as an electrode overlying the fourth lumbar vertebrae, or other physiological reference point. This calibration information is then fed into the electronic apparatus 22 for appropriate adjustment of the voltage data received from electrodes 28 and subsequent visual display relative to predetermined displays of muscular anatomy appearing at display unit 26, in order to assure standardization of electrode placement.

In an alternative exemplary embodiment, an alternative protocol may be used for positioning and locating the electrode array. Such methods may be used in connection with sensor pad 10 as well as the reusable and self adhesive sensor pads later discussed.

Locating of the sensor pad begins with the patient in a neutral upright position. The patient's feet are preferably shoulder width apart, the head and face forward. The clinician positioning the electrode array may palpate both the left and right superior iliac crests to locate their position. Drawing an imaginary line directly between these two points, the clinician palpates the spinous process at this level which is L4 the fourth lumbar vertebrae. The clinician then marks the L4 spinous process with a water soluble marker. The electrode positioned in the middle column and seven rows from the top is then positioned directly over the L4 indicator. This electrode is marked 47 in FIG. 2.

Continuing with the location and calibration process, once the L4 electrode has been positioned the clinician palpates the most inferior point of the inferior angles of both scapulae. The clinician then envisions an imaginary line between these two points and palpates the spinous process at this level. This is the seventh thoracic vertebrae T7. The clinician may then use calipers or other suitable measuring device for measuring from the T7 spinous process to electrode 47 at L4. This measurement may be recorded, or in some embodiments input to the computer through an input device for correlating the output to the dimensions of the patient's anatomy in a manner that is later discussed.

Continuing with the protocol, with the patient in the same position the clinician finds the left superior iliac crest at its most lateral point. Using calipers or other measuring device the clinician measures from the most lateral aspect of the left iliac crest to the electrode at L4. This measurement is also recorded or in some embodiments input to the computer through an input device.

In some embodiments, the computer 25 includes software which is operative to scale outputs displayed responsive to the configuration of the patient's anatomy. This is achieved because the dimensions of the patient are known as are the distances between the electrodes. In this manner the computer is enabled to calculate or otherwise determine how the anatomical features underlying the electrodes correspond to the electrode positions for the given dimensional configuration of the patient. This enables signals from electrodes to be more accurately correlated to underlying anatomical structures, such as muscles which are exhibiting spasmodic conditions.

Figure 8:
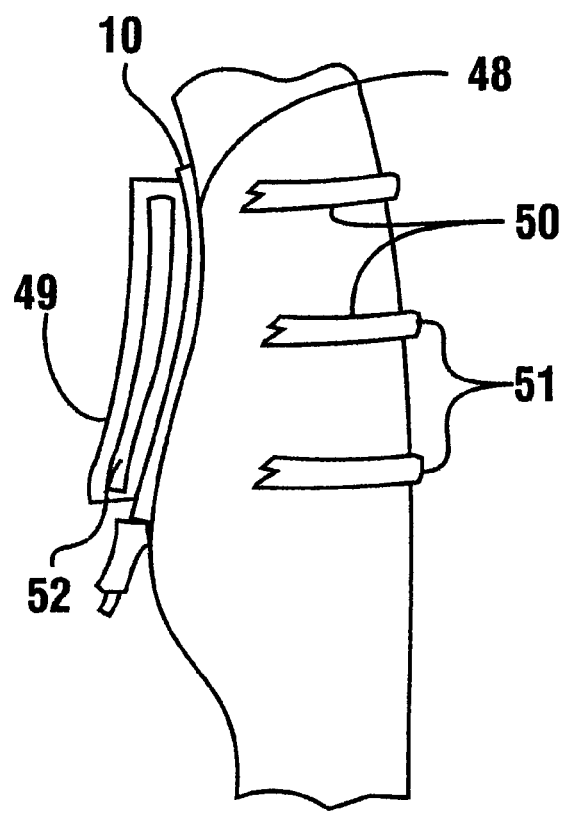
FIG. 8 is a schematic view of the lower torso of a patient with the sensor pad held in position by a retaining belt and a support pad.
Figure 9:
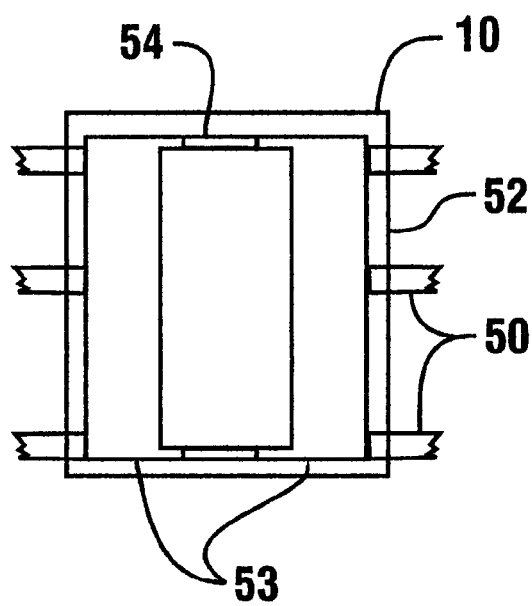
FIG. 9 is a plan view with parts removed of the retaining belt of FIG. 8, showing the support pad.
Figure 14:
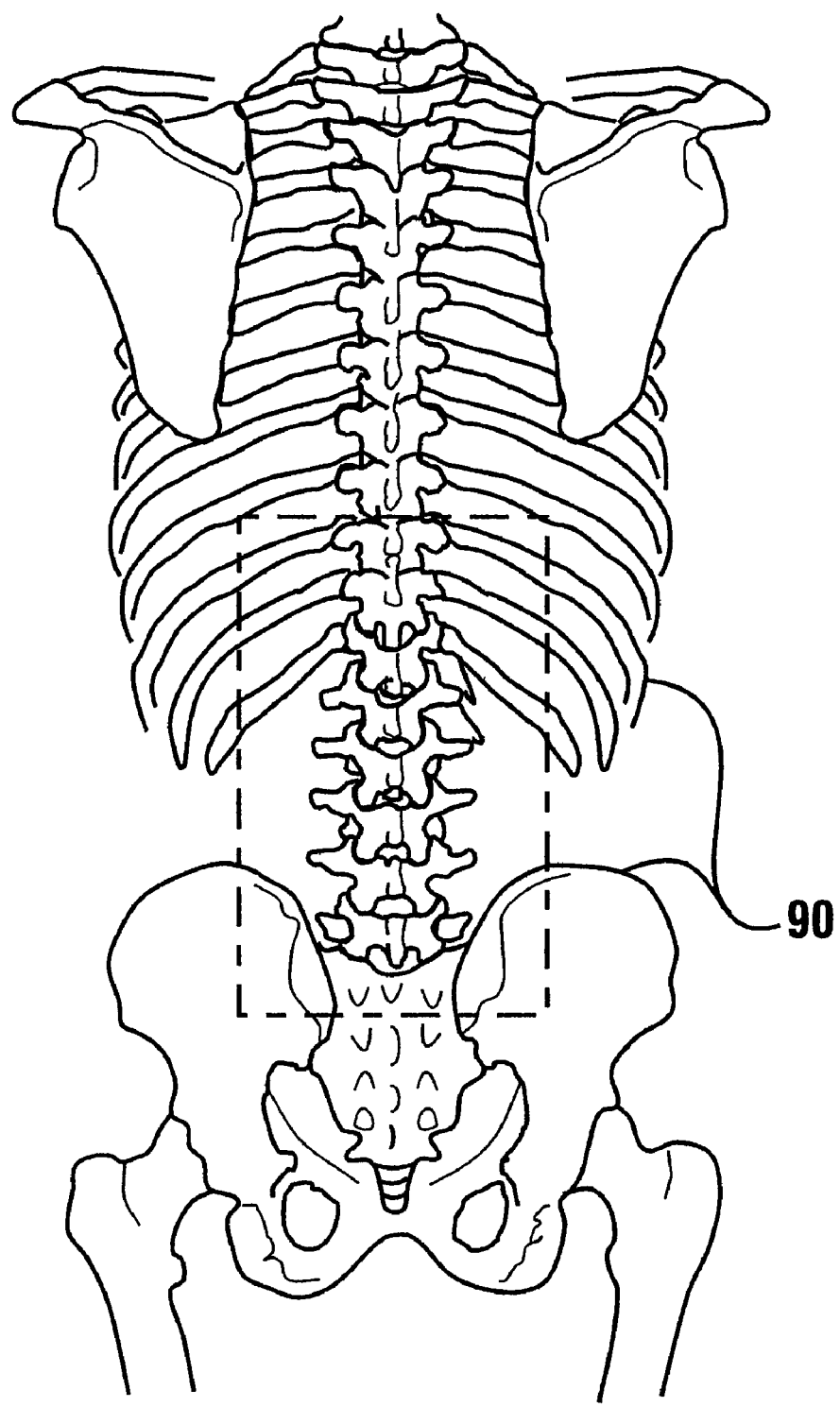
FIG. 14 is a schematic diagram of skeletal anatomy associated with the lower back of a normal human patient.
Figure 15:
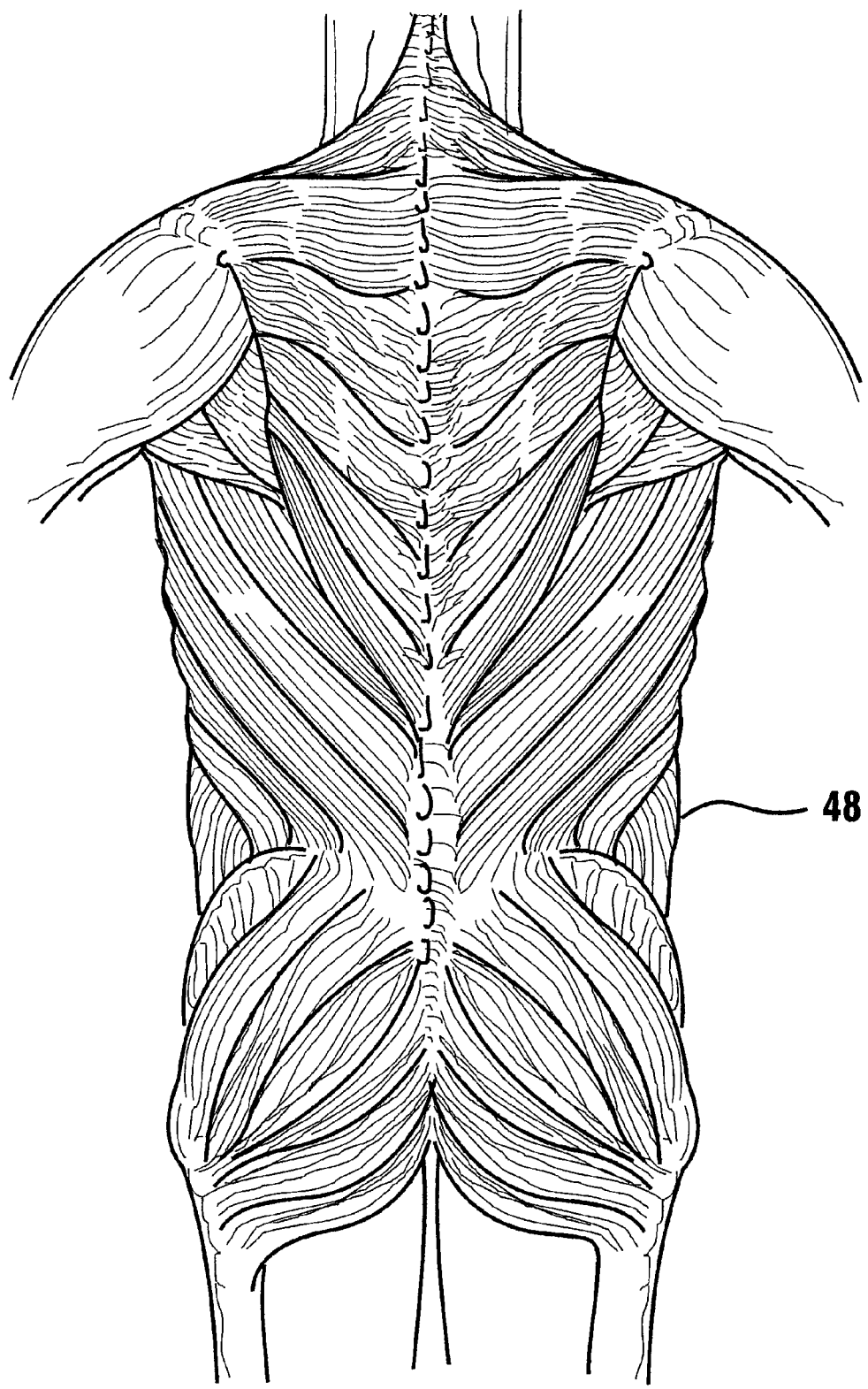
FIGS. 15-23 are schematic diagrams of various groups of musculature of a normal human patient shown in relation to the skeletal anatomy of FIG. 14.
Figure 16:
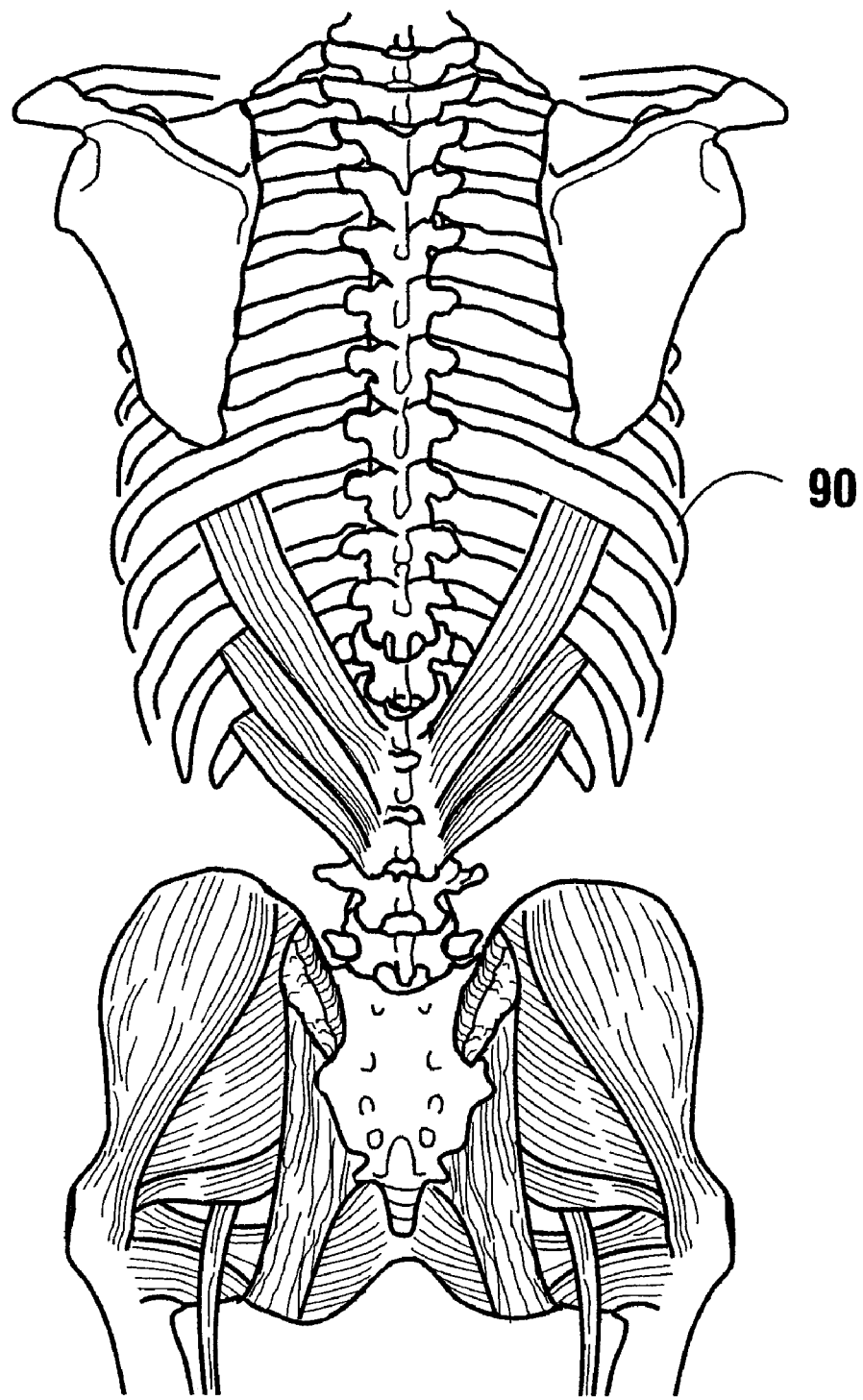
Figure 17:
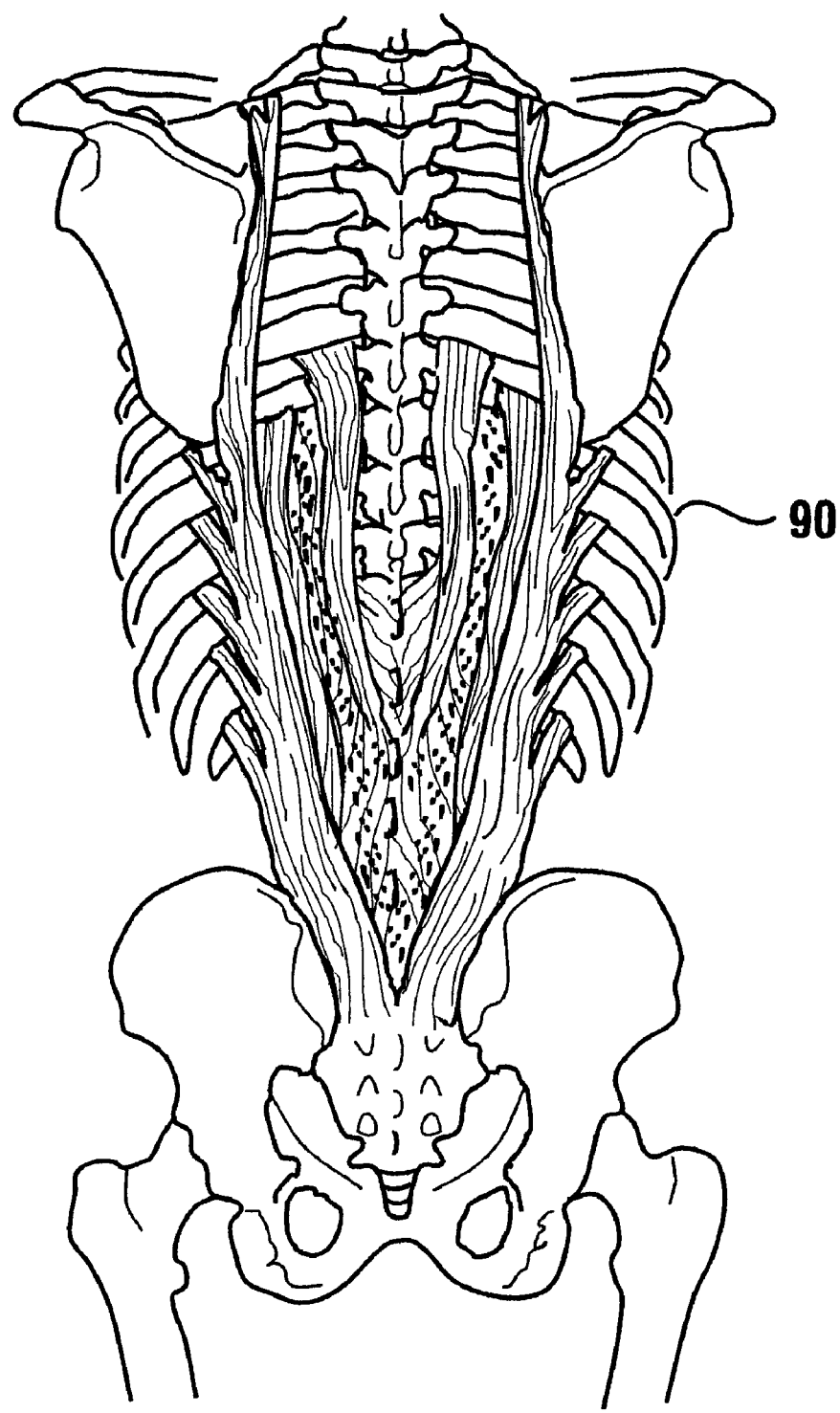
Figure 18:
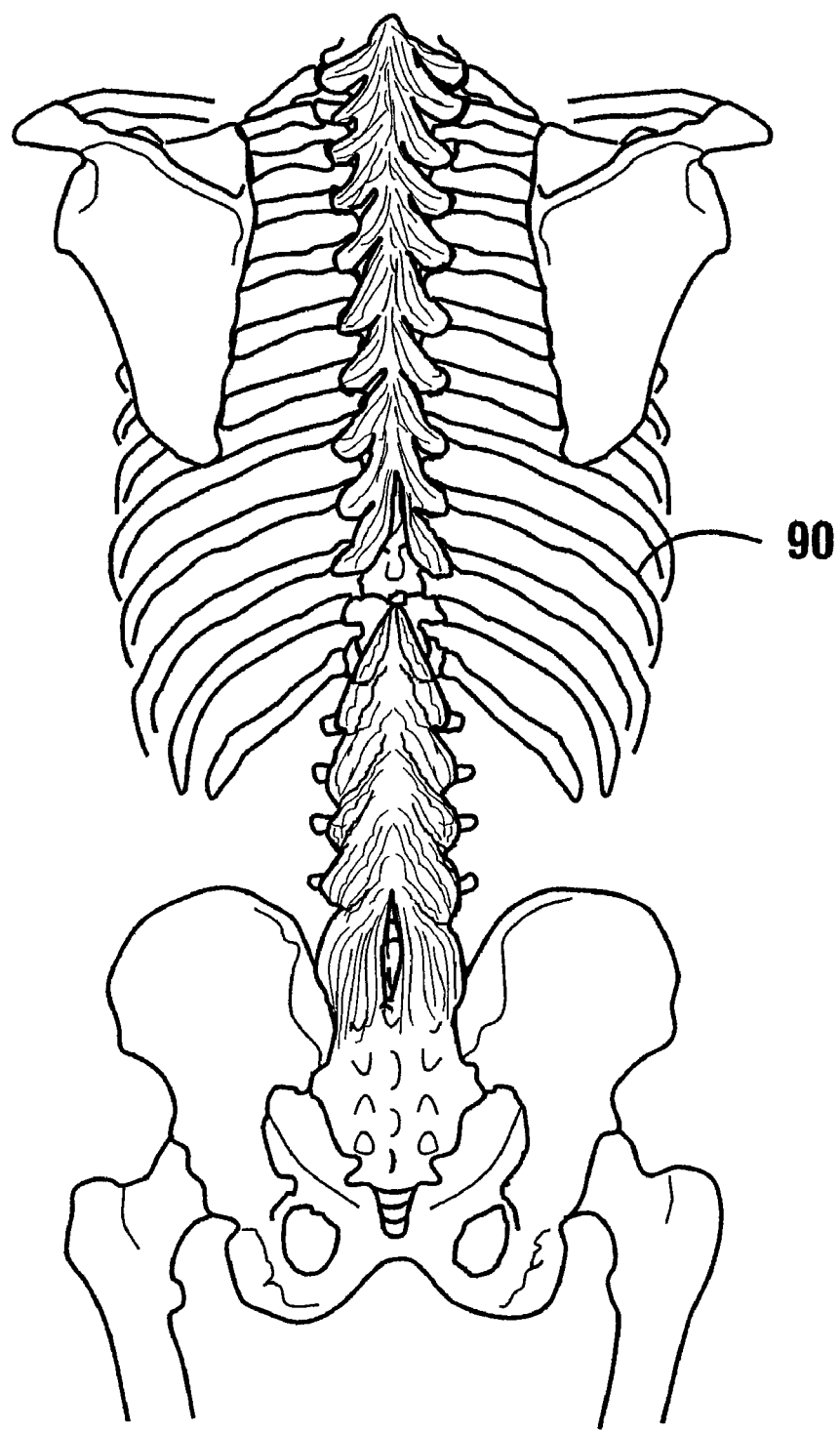
Figure 19:
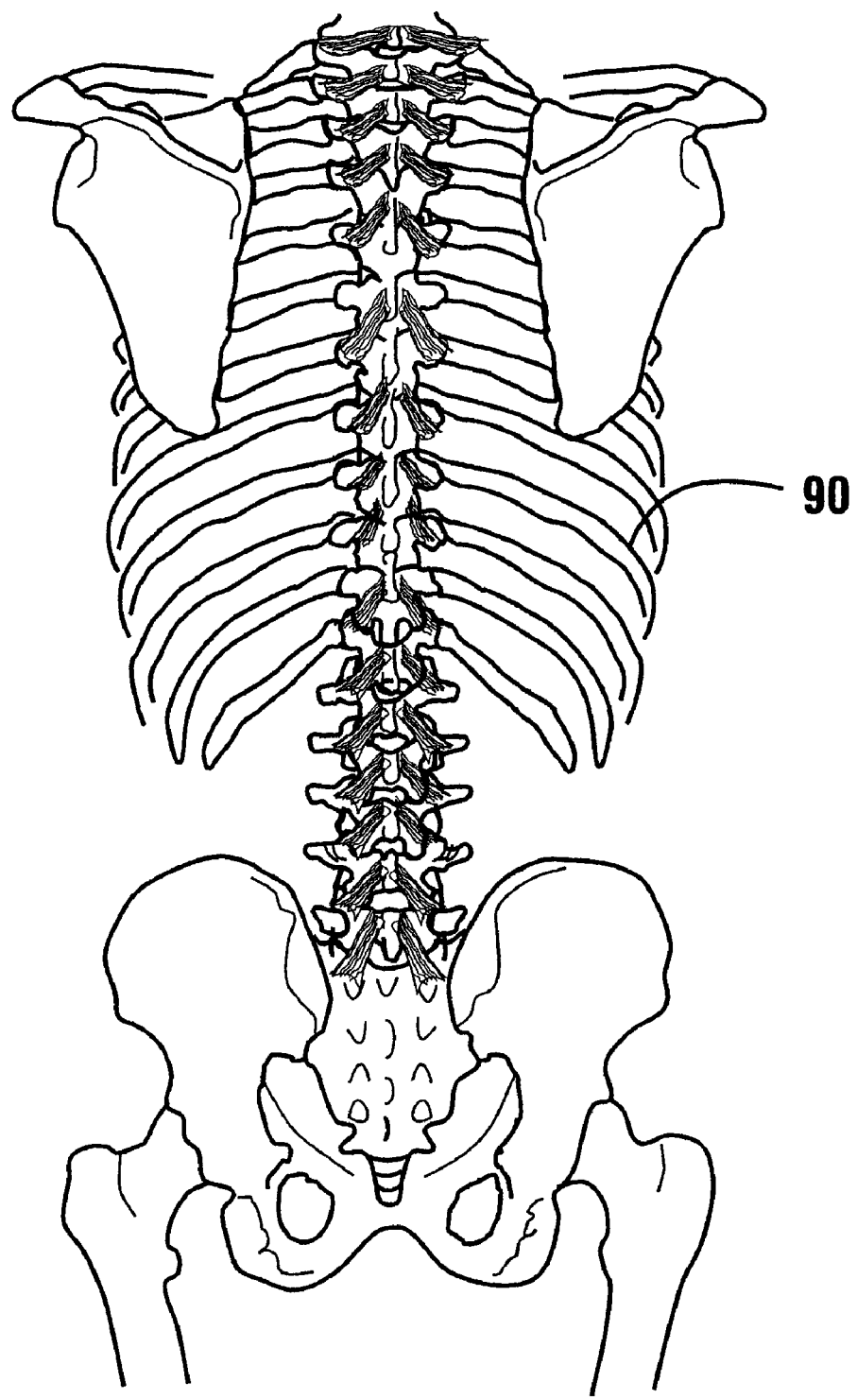
Figure 20:
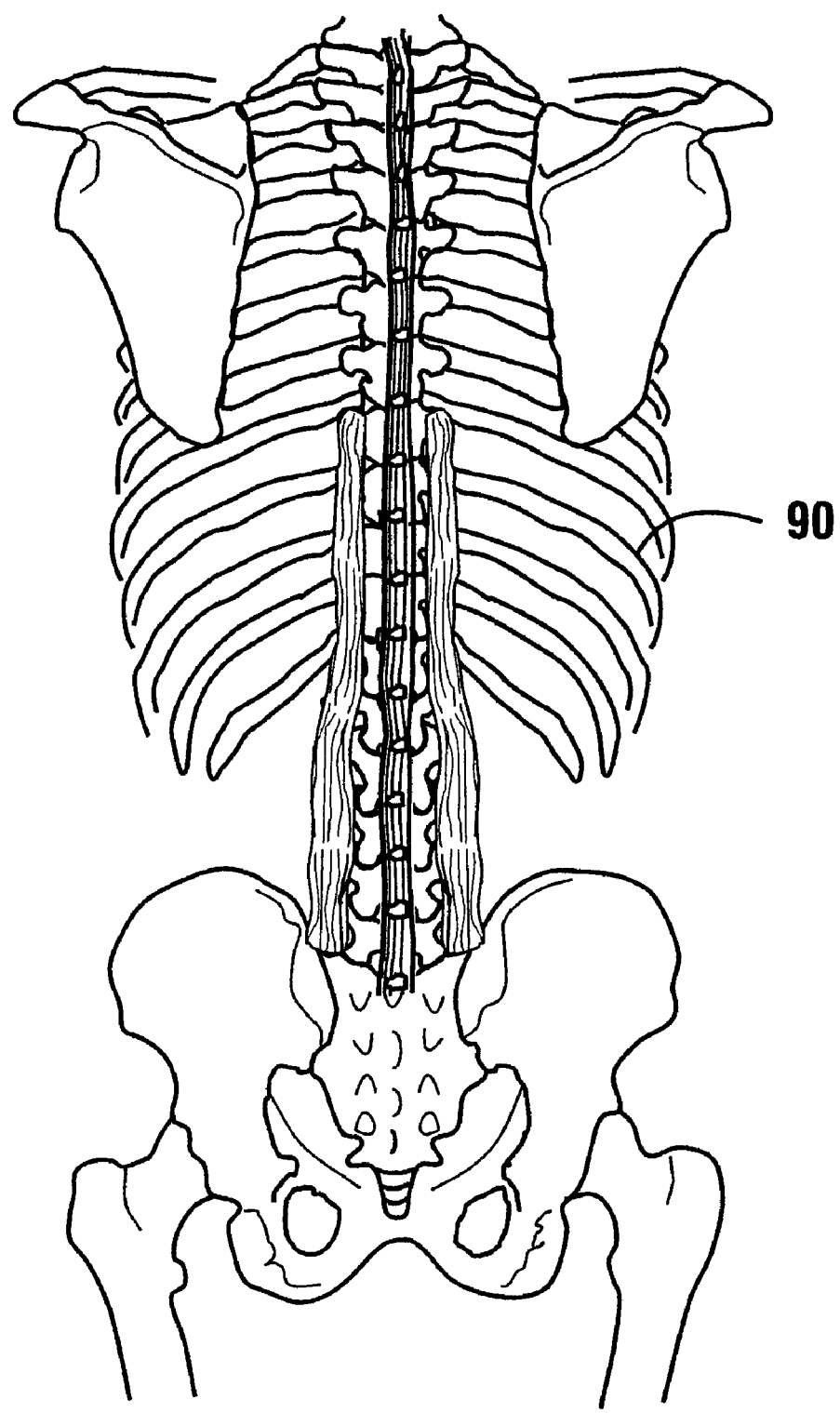
Figure 21:
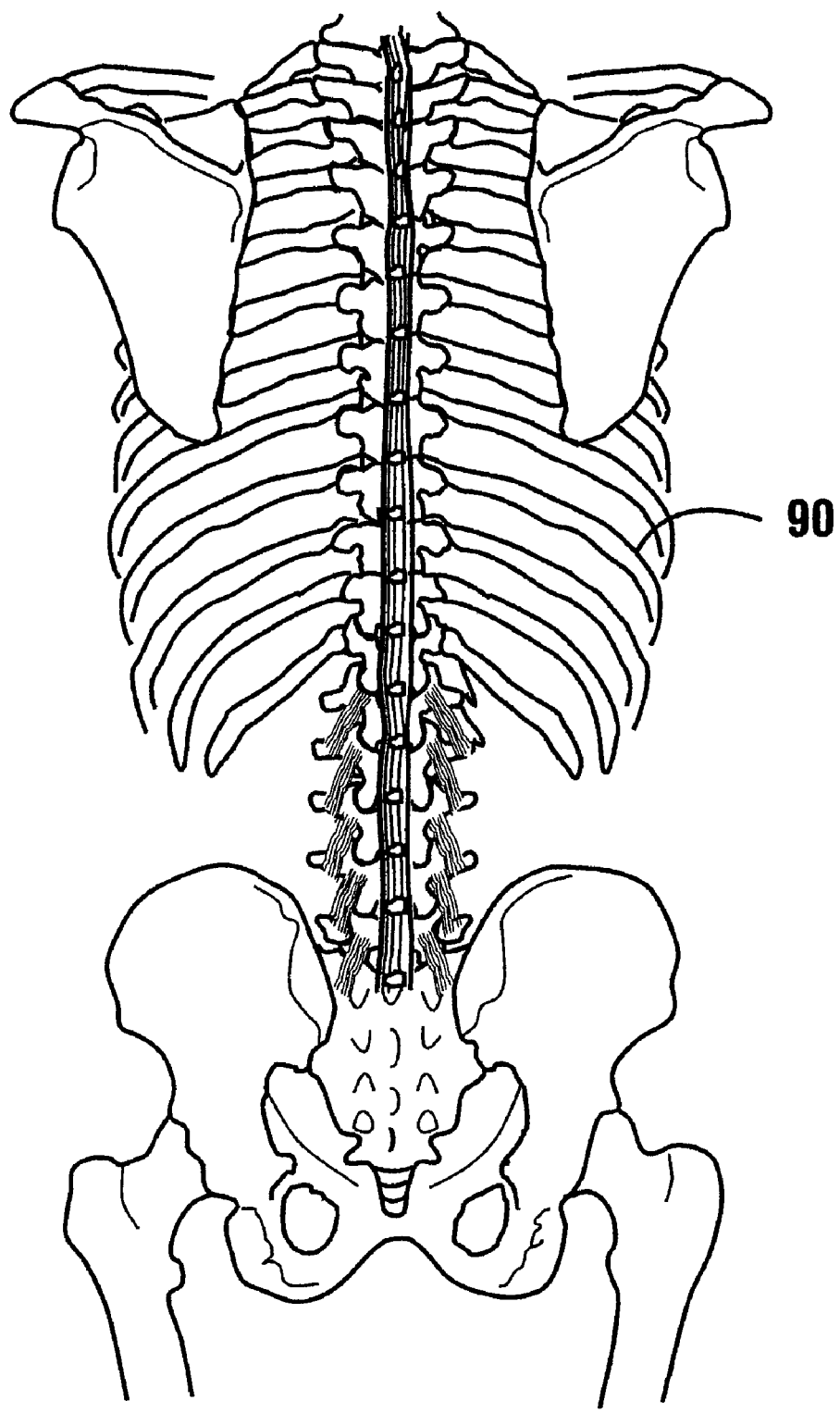
Figure 22:
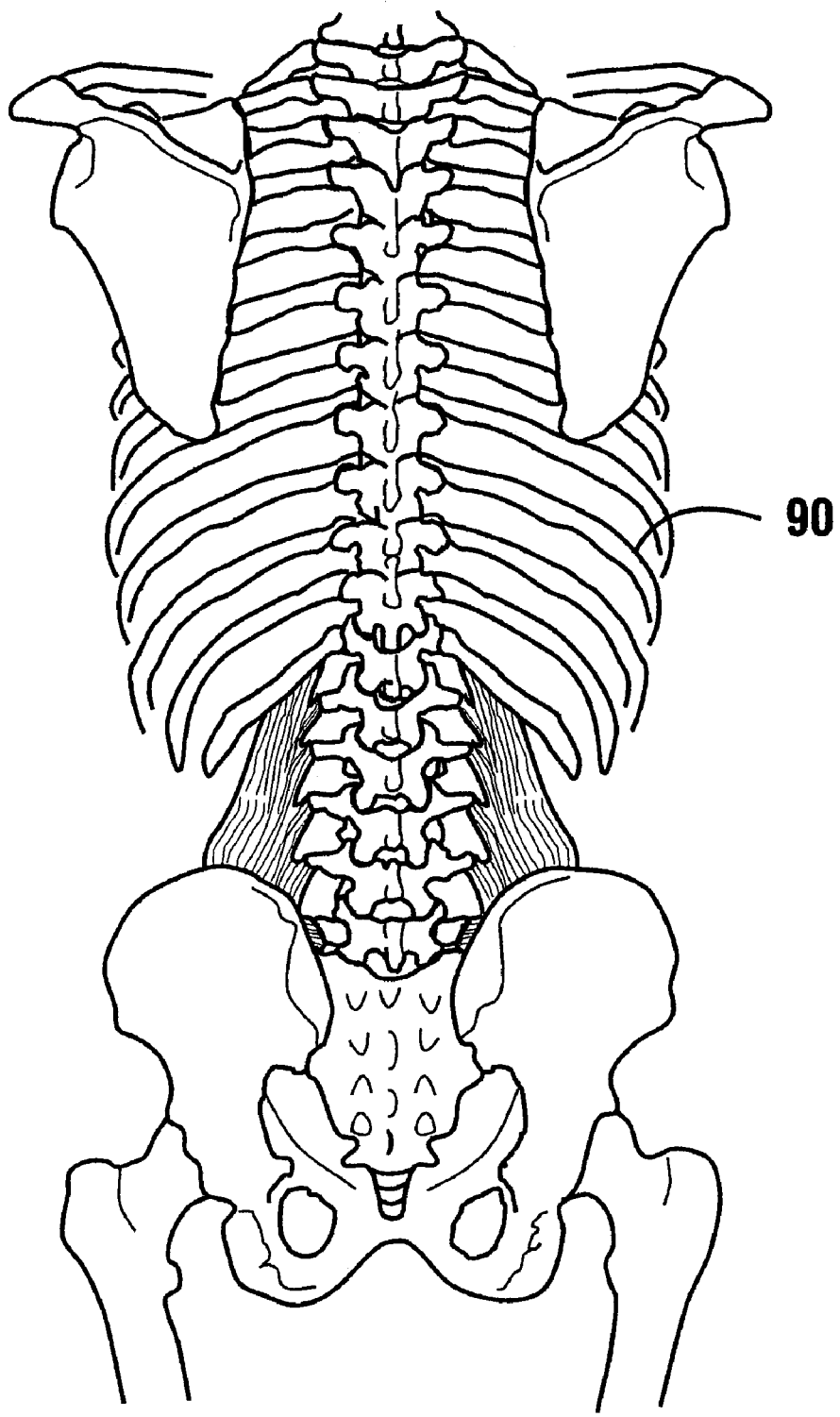
Figure 23:
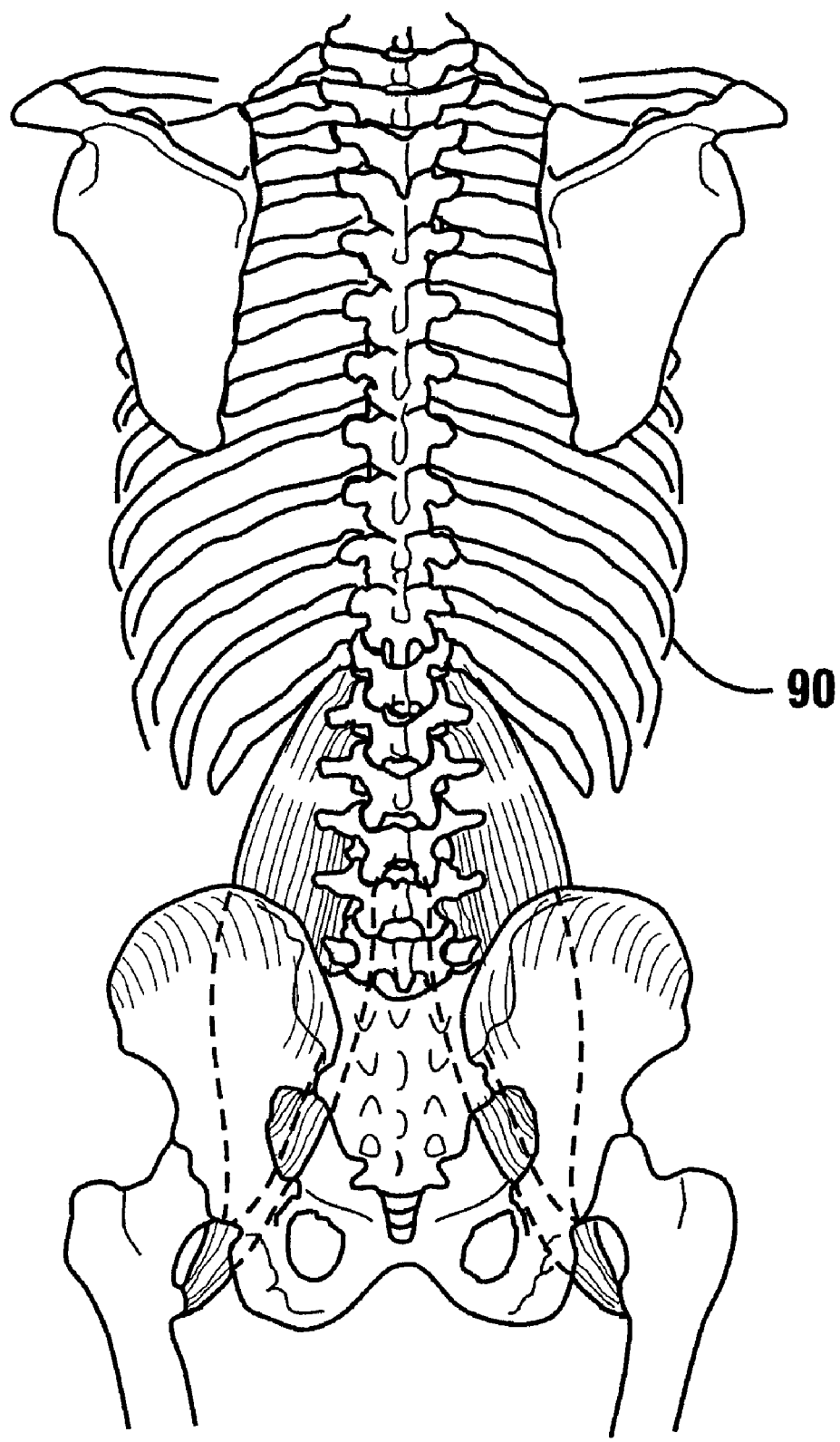

Referring now as well to FIGS. 8 and 9, there is shown in two views the mechanism for attachment of sensor pad 101 to the lower back of a human patient 48. A type of lumbar support belt 49 encircles part of the lower torso of patient 48 and is retained in place by several straps 50 of non-elastic web culminating in quick release snaps 51 at the ends thereof for adjustment and securement. Belt 49 includes a pouch therein in which is disposed a molded foam pad 52. Pad 52 is generally rectangular in configuration and about 2.54 cm (one inch) in thickness at its midpoint and tapering to about 0.3175 cm (0.125 inch) thickness at its left and right edges. The pad has a curved inner surface generally conforming to the curvature of the lower torso of a typical patient 48 and overlying sensor pad 10 to press the latter into secure physical contact with patient 48 as straps 50 are adjusted. Preferably, belt 49 is about five cm (two inches) larger than the operative portion of sensor pad 10, and pad 52 is also slightly larger than sensor pad 10, thereby to overlap the latter and assure fairly uniform pressure over the entire area of sensor pad 10 and consistent readings from electrodes 28.

The pad 52 may have three parts, namely parallel vertical sections 53 and a central stiffer section 54. Pad 52 is firm, yet flexible, and thicker in the central section 54 than in the outer sections 53 as described above. In this manner a better fit is made to accommodate the contour of the human back. Support belt 49 is preferably made of non-elastic nylon material as are straps 50 to achieve a secure and reliable connection to the patient 48.

A conductive gel may be applied to electrodes 28 (or alternative electrodes 200) to enhance conductivity of the interface between electrodes and patient 48, as is well known in the art. One suitable brand of water soluble gel is that manufactured by TECA, a subsidiary of Vickers Medical, Inc.

Alternative approaches to locating and securing the electrodes to a patient may be used. For example FIG. 37 discloses an EMG sensor device in the form of a disposable sensor supporting pad or sheet generally indicated 220. Sensor supporting sheet 220 comprises a flexible web material that is relatively thin and sufficiently flexible to conform to the contours of the patient. As shown in FIG. 38 web material 222 includes apertures 224 therethrough. Apertures 224 are sized for accepting the head portions of electrodes designated 226 therethrough. The electrodes may be of the type described herein or other types. For example when electrodes 200 are used the apertures 224 are sized such that the head portion of the electrode is enabled to contact the skin of the patient in the area of the conical portions 208. The front face 228 of the web material 222 preferably includes an adhesive thereon. The adhesive is preferably made to adhere to the skin of the patient once adjacent thereto, but may be released from the skin in response to a less than harmful removal force. The adhesive material applied on the front face is preferably sufficiently strong once adhered to prevent relative movement of the electrodes on the skin of the patient until the web material is removed by a clinician. The adhesive material on the front face 228 is preferably covered by a separable cover sheet which covers the adhesive material until the sensor supporting sheet is ready to be applied to a patient.

Figure 37:
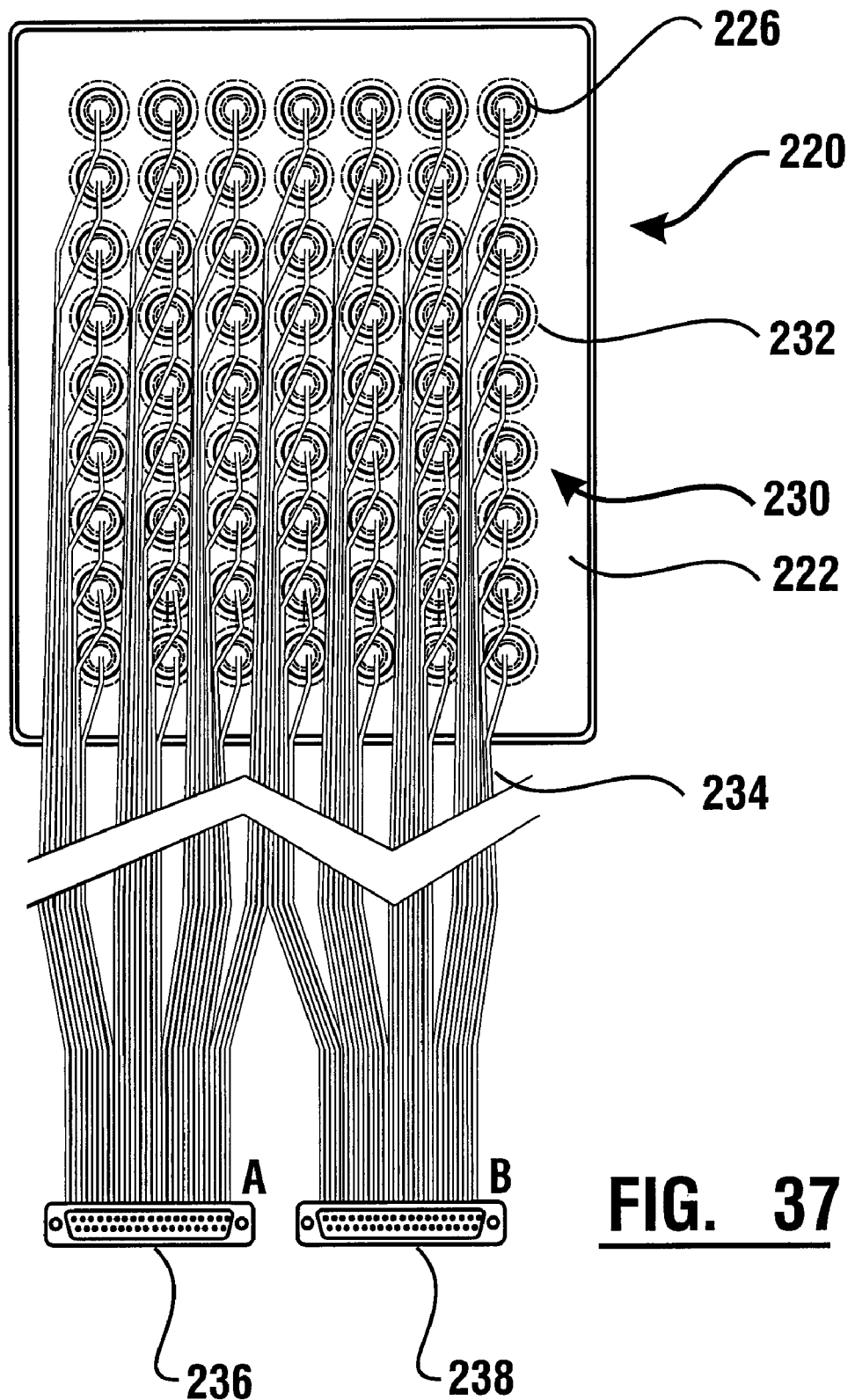
FIG. 37 is a rear plan view of an electrode array and self adhesive electrode support pad.
Figure 38:
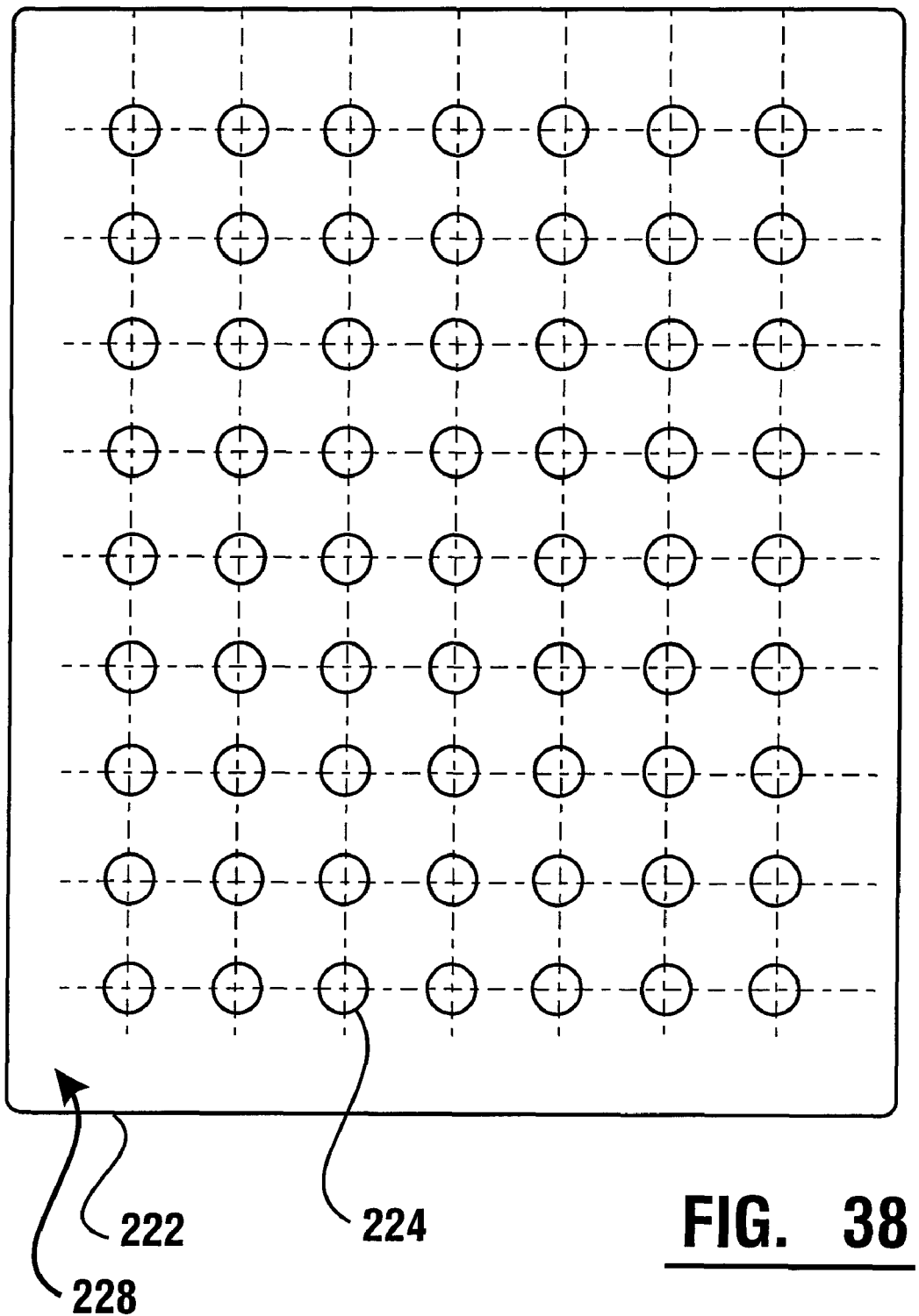
FIG. 38 is a front plan view of the self adhesive support pad shown in FIG. 37 without electrodes mounted thereon.

As shown in FIG. 37 the electrodes 226 are held to a rear face 230 of the web material 222. This is accomplished in the embodiment shown by support discs 232. Support discs 232 are preferably flexible sheet material with an adhesive or similar flexible attaching means thereon which adhere to both the electrodes and the rear face 230. The support discs include an opening therethrough which enables wires or other electrically conducting elements 234 to extend therethrough to contact the electrodes. It should be understood that while electrical wires are shown in the embodiment described in connection with FIG. 37, in other embodiments other types of electrical conductors such as electrical trace conductors or other types of conducting means may be used. As shown in FIG. 37 the wires 234 terminate at electrical connectors 236 and 238. The electrical connectors are adapted to connect the wires and the associated electrodes to the remainder of the system.

The disposable electrode array which includes sensor supporting sheet 220 is useful because it is sufficiently flexible to conform to the contours of a patient's anatomy. Further the adhesive material secures the electrode in contact with the patient's skin and generally prevents relative movement until the sensor array is ready to be removed. The disposable character of the sensor supporting sheet also reduces time associated with cleaning components between patients. The components of the system are preferably assembled in a manner that enables the wires and electrodes to be readily disconnected, cleaned and recycled into new sensor supporting sheets.

Figure 39:
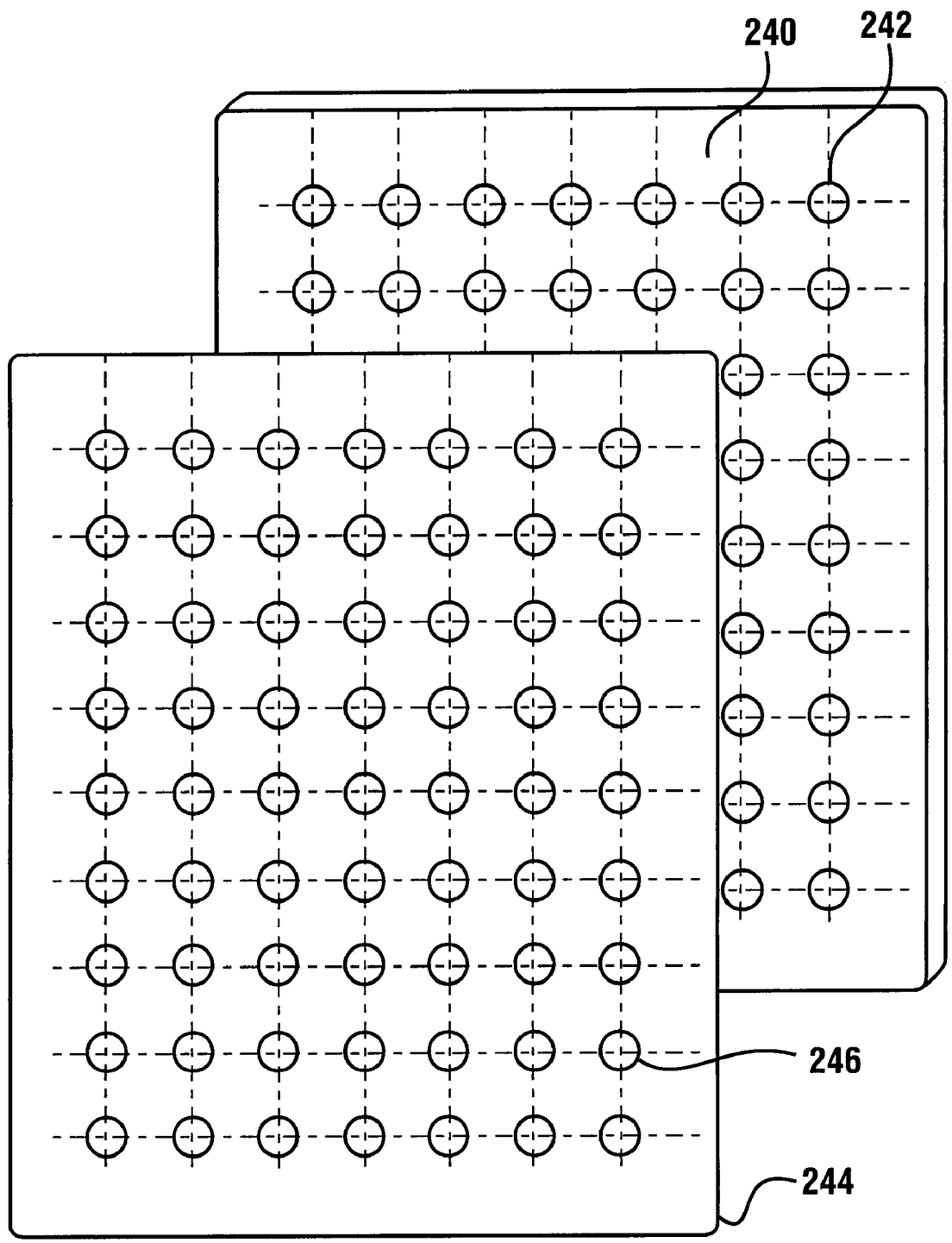
FIG. 39 is an isometric view of a reusable electrode support pad and removable adhesive web for use in connection with the reusable electrode support pad.

A further alternative configuration for an EMG sensor device is shown in FIG. 39. In this described embodiment the electrodes are supported on a flexible resilient pad 240. Pad 240 is preferably comprised of silicone or other material sufficiently flexible to conform to the contours of a patient's body. Electrodes designated 242 are positioned in supporting connection with the pad. Electrodes 242 may be mounted in apertures that extend through the pad 240 in some embodiments. Alternatively electrodes 242 may be in molded connection with the pad. In addition the wires which extend to the electrodes 242 may also be molded into the pad to facilitate connection to the electrodes and to minimize the risk of damage.

A double stick adhesive web or sheet 244 is positioned adjacent to pad 240. Adhesive sheet 244 includes apertures 246 that extend therethrough. The positions of apertures correspond to the positions of electrodes 242 such that the heads of the electrodes may extend therethrough. Adhesive sheet 244 includes adhesive on the side adjacent to the pad 240 which serves to adhere to the adhesive sheet thereto. However the nature of the adhesive and the sheet material is such that the adhesive sheet once adhered to the underlying pad may be removed therefrom without damaging the pad or the electrodes.

The adhesive sheet 244 further includes an adhesive material on the side opposite the pad 240. This adhesive material is suitable for adhering the sheet 244 and the attached pad 240 to the skin of the patient in a manner similar to the sensor supporting sheet 220. The adhesive sheet 244 preferably includes a reversable cover sheet or similar item attached to the patient side thereof to maintain the adhesive generally dirt free until the sheet is ready to be adhered to the back of the patient. When the pad 240 is ready to be brought into contact with the patient's back the sheet covering the adhesive on the patient's side of sheet 244 may be removed. The pad 240 may then be positioned and conformed to the contours of the patient and the signals from the electrodes may then be analyzed as later discussed. When the analysis and other activities are complete the pad 240 and sheet 244 may be removed from the patient's back.

A useful aspect of the structure shown in FIG. 39 is that the adhesive sheet will generally absorb the dirt, hair and other material collected from the patient. After use the sheet 244 may be separated from the adhesive pad 240. The surfaces of the electrodes may then be cleaned and the pad made ready for reuse. The ability to collect hair and other material on the disposable adhesive sheet 244 reduces the time required for cleaning the electrodes and pads. Of course in other embodiments, other approaches may be used.

Figure 40:
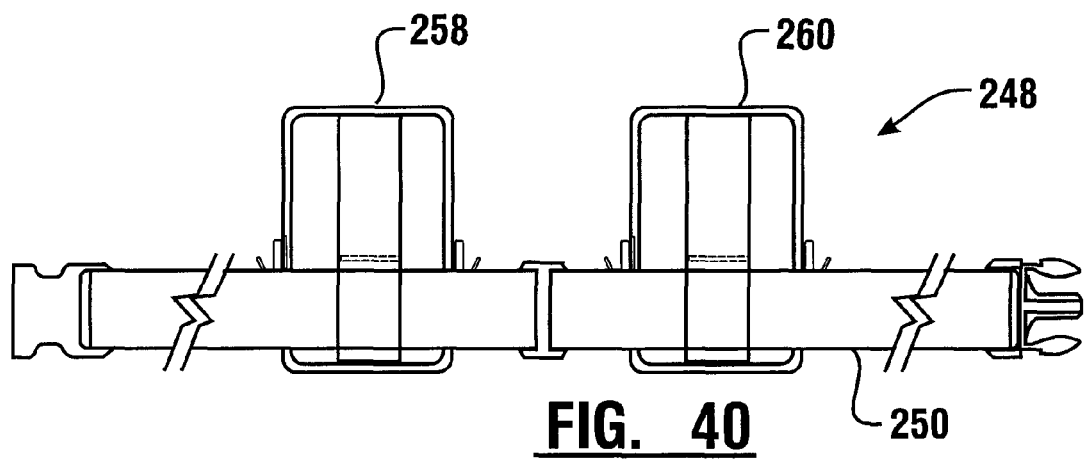
FIGS. 40, 41 and 42 are back, top and front views respectively, of the electrical component holster supporting belt worn by a patient in connection with self adhesive electrode array supporting pads.
Figure 41:
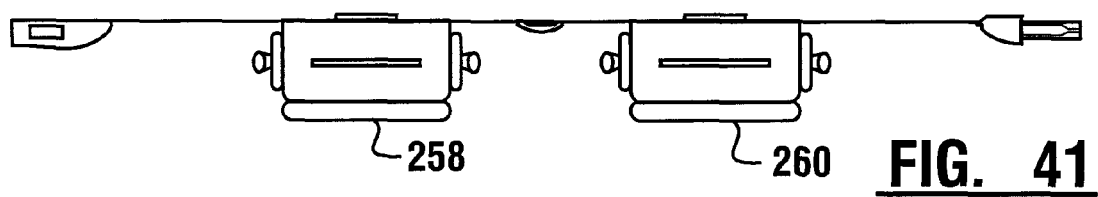
Figure 42:
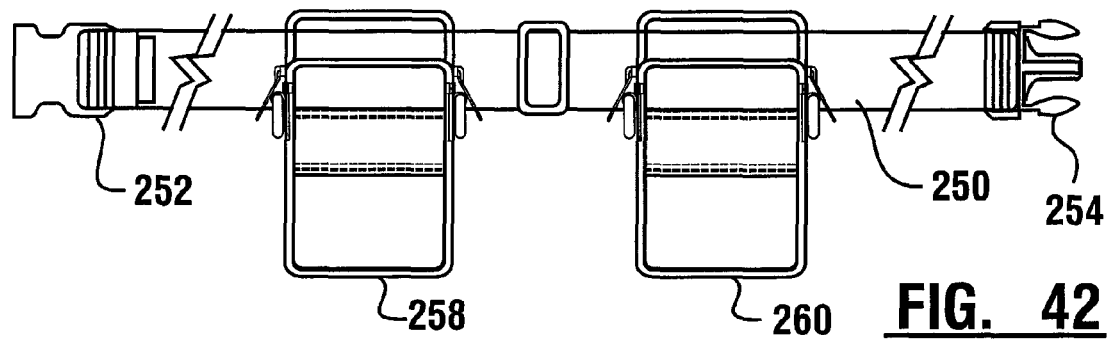

When the electrode arrays shown in FIGS. 37 and 39 are used there is generally no location on the structure supporting the electrode array to mount the electronics components for amplifying and conditioning the signals which are derived from the electrodes. As previously discussed, it is advisable to condition and/or amplify such signals as close to the source as reasonably possible to avoid the introduction of extraneous signals. To achieve this goal the holster and belt combination designated 248 and shown in FIG. 40-42 is used. Holster belt 248 includes an adjustable belt portion 250 which can be sized to be supported around a suitable area of the patient. In most cases this will be the patient's waist or hips. A quick release buckle or a reversable snap including a first end 252 and a cooperating second end 254 are attached to the belt portion.

A first pocket 258 and a second pocket 260 are supported on the belt portion 250. Each of the pockets preferably includes electrical connectors which provide an electrical connection with connectors from the electrode array such as connectors 236 and 238 shown in FIG. 37. Pockets 258 and 260 also preferably include electrical signal conditioning components which are desirable to place adjacent to the patient. This may include for example the preamplifiers and other signal generating or conditioning circuitry for conditioning the electrode signals. Pockets 258 and 260 may also include further connectors for outputting the conditional electrical signals therefrom.

It should be understood that the described form of the holster belt 248 is exemplary and in other embodiments other approaches to supporting the electrical connectors and signal conditioning components may be used. These may include for example supporting such components on other structures supported by the patient or on other types of support structures which are not supported by the patient.

Figure 43:
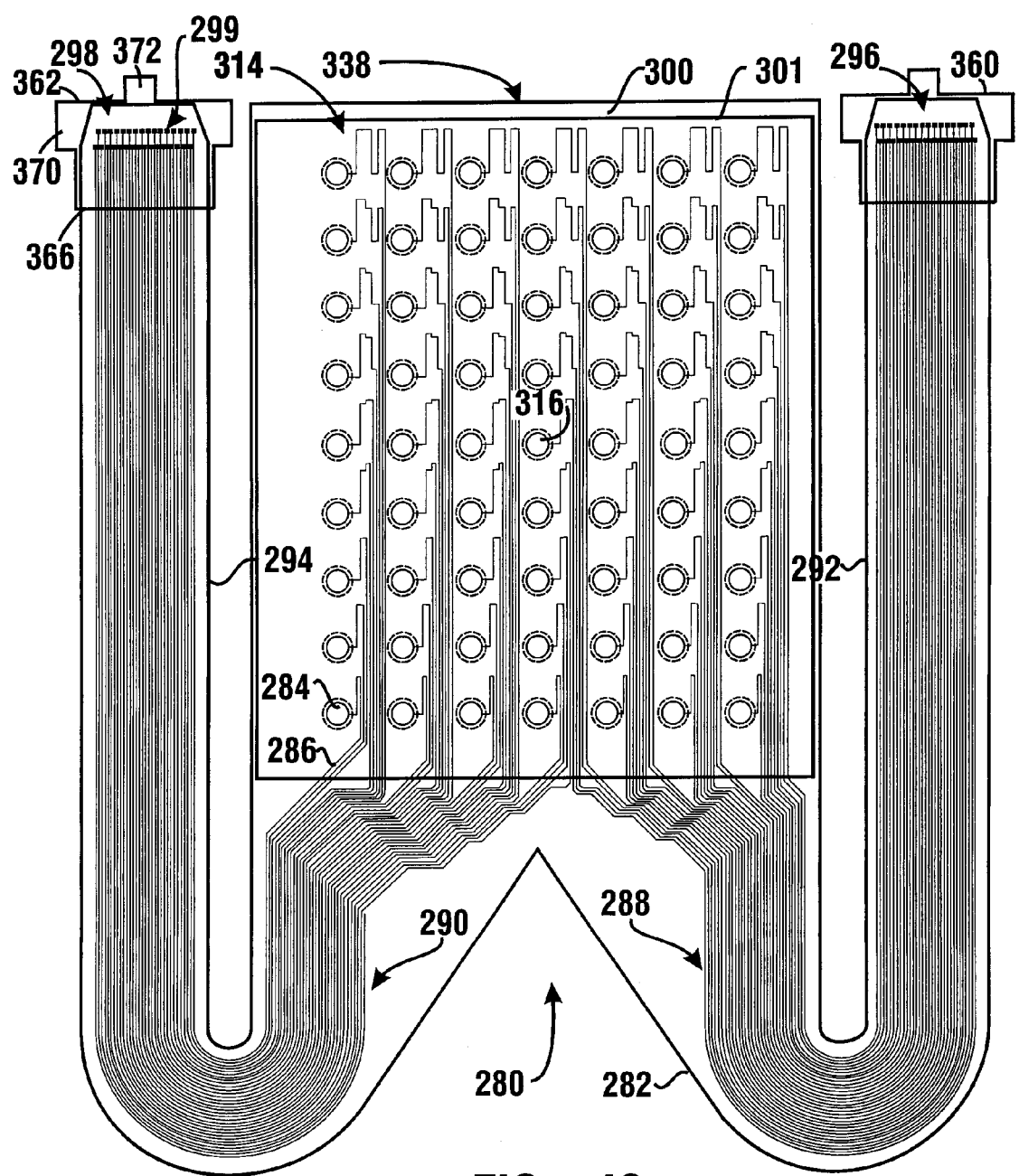
FIG. 43 schematically represents an exemplary embodiment of a flexible electrode array.

FIG. 43 schematically represents a further alternative embodiment of an EMG sensor device in the form of a flexible electrode array 280. Here both the electrodes 284 and electrical traces 286 are formed by depositing or printing electrically conductive inks on a flexible non electrically conductive substrate 282. In this described exemplary embodiment the substrate 282 is a sheet of polyester such as Mylar®; however, in other embodiments other flexible materials that are operative to support conductive materials may be used.

A plurality of the electrodes 284 are printed on the substrate 282 in a predetermined pattern. In this described exemplary embodiment the electrodes 284 are printed in uniform array 314 of nine by seven electrodes. Each electrode is printed in the shape of a solid circle with a diameter of about 1.27 cm (0.5 inches). However, in other embodiments other sizes, shapes, and patterns of electrodes can be printed based on the desired sensitivity and intended use for the flexible electrode array. Other examples of possible electrode shapes include hexagons and stars.

At lease one trace is printed on the substrate 282 for every electrode. The traces are printed in a pattern such that the traces are in electrical connection with the electrodes. The traces then converge into two groupings 288 and 290 of parallel trace lines. In this described exemplary embodiment the substrate is cut to include two long tails 292 and 294. The groupings of parallel traces 288 and 290 are printed along the tails 292 and 294 and terminate at connection ends 296 and 298. The connection ends are printed in a pattern that is operative to mate with an external electrical connector such as the Zero Insertion Force (ZIF) connector discussed later in detail. For this described exemplary embodiment the center electrode 316 is used as a reference electrode and may be connected to one or more additional trace lines.

When in use with the computerized EMG diagnostic system, the mid section 300 of the flexible electrode array is placed against the back of a patient. The tails 292 and 294 have sufficient length and flexibility to wrap around the torso of the patient and to connect to additional conditioning circuitry such as buffer/amplifiers. The additional circuitry may be located in the pouch of a holster belt as discussed previously or may be connected to a belt with a clip or other attachment device such as snaps or velcro.

Figure 44:
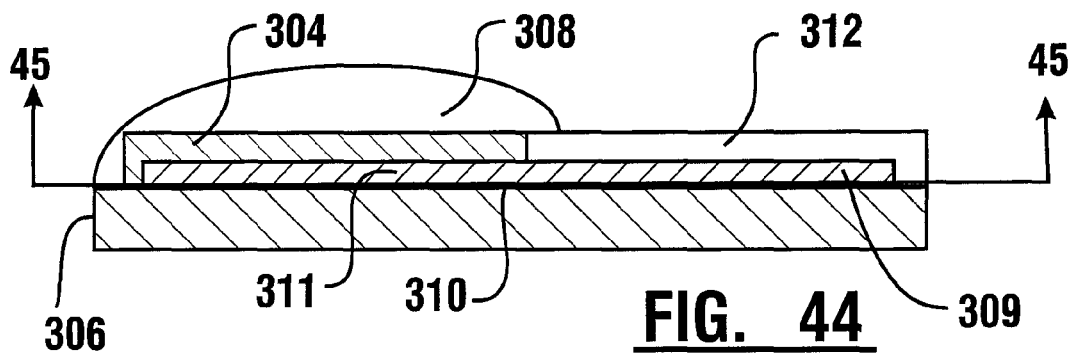
FIG. 44 is representative of a cross sectional side view of the deposited materials comprising the flexible electrode array

FIG. 44 is representative of a cross sectional view of the flexible electrode array 302. In this described exemplary embodiment each electrode 304 is silk screen printed on the substrate 306 with a highly conductive printing material such as a silver/silver chloride epoxy ink. A conductive self supporting adhesive 308 such as hydrogel is stenciled over each printed electrode and UV cured in place. In alternative embodiments the hydrogel can be cured by other means including thermal curing. The hydrogel provides additional electrical conductivity between the surface of a patient's back and the printed electrode. In addition the hydrogel enables each printed electrode to adhere to a patient's back with sufficient adhesive strength to support the flexible electrode array in place.

Figure 45:
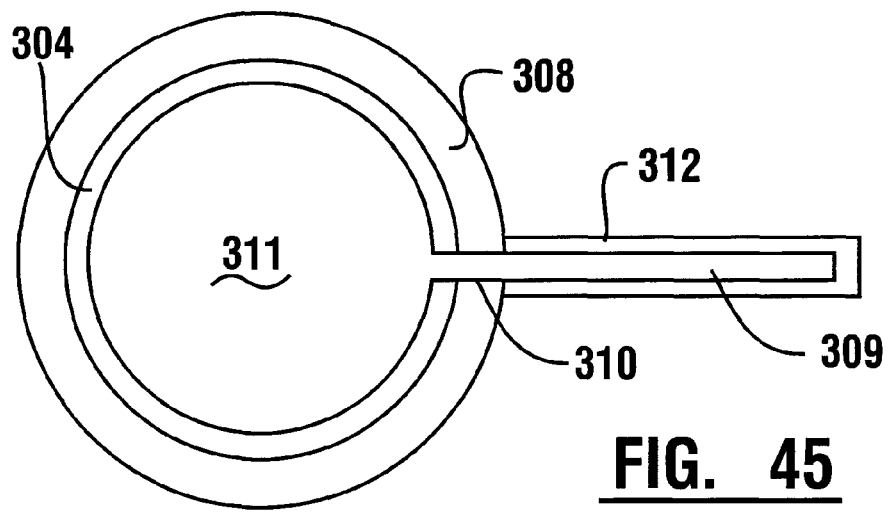
FIG. 45 is representative of a cross sectional bottom view of the deposited materials comprising the flexible electrode array.

In this described exemplary embodiment, traces 310 are silk screen printed on the substrate 306 with a silver epoxy ink 310. As shown in the cross-sectional bottom view of FIG. 45, each trace 310 includes a circular end 311. The silver/silver chloride epoxy ink of the electrode 304 is printed over the silver epoxy circular end 311 of the trace 310 to provide a strong electrical connection between the electrode and the trace deposits.

In addition, the more narrower trace line portions 309 of the traces 310 are insulated by printing additional layers of a non conductive ink 312 over the trace lines 309. In this described exemplary embodiment each conductive trace line is about 0.05 cm (0.02 inches) in width. The insulating ink line is centered over each conductive trace line and has a width of about 0.2 cm (0.08 inches). In alternative embodiments trace lines 309 may have variable widths so that the impedance of each trace is the same, even though the trace lines have different lengths.

Although in this described embodiment the electrodes and traces are silk screened on a substrate, in alternative embodiments, the flexible electrode array can be produced by any process that is operative to deposit or print a specifically defined pattern of conductive materials on a flexible sheet. Examples of such other processes includes flexographic printing with conductive inks. In other embodiments subtractive methods can be used such as chemical etching of aluminum or copper on clear polyester.

In addition, rather than insulating trace lines with non conductive inks, other embodiments may include a non conductive overlay sheet for insulating the printed trace lines. Such an overlay would leave the electrodes and connector ends exposed by including a plurality of apertures in the overlay which coincide with the printed electrodes and connector ends.

One advantage of printing both the electrode and the traces on a clear flexible plastic substrate such as polyester sheet is the reduction in the cost associated with manufacturing the flexible electrode array. The lower cost enables the flexible electrode array to become a disposable part in the computerized EMG diagnostic system; thus, eliminating the need to clean electrodes between uses of the system. In addition, using a transparent substrate such as a polyester sheet, aids in the accurate positioning of the electrodes by allowing a clinician to see the underlying anatomy of the patient through the flexible electrode array. Thus, after a clinician has marked the locations of vertebra on a patients back, the clinician can precisely position the center column of the printed electrodes over these markings.

Another advantage of using a polyester substrate such as Mylar®, is that polyester film is a material that is both tear resistant and sufficiently flexible to conform to the general shape of a patient's back. Further, the embodiments described herein achieve increased flexibility and extensibility in the design of the flexible electrode array by including a plurality of strategic slits in the substrate to make the flexible electrode array extensible (stretchy) in between electrodes. This enables the flexible electrode array to stretch or compress in three directions (horizontal, vertical, and diagonal).

Figure 46:
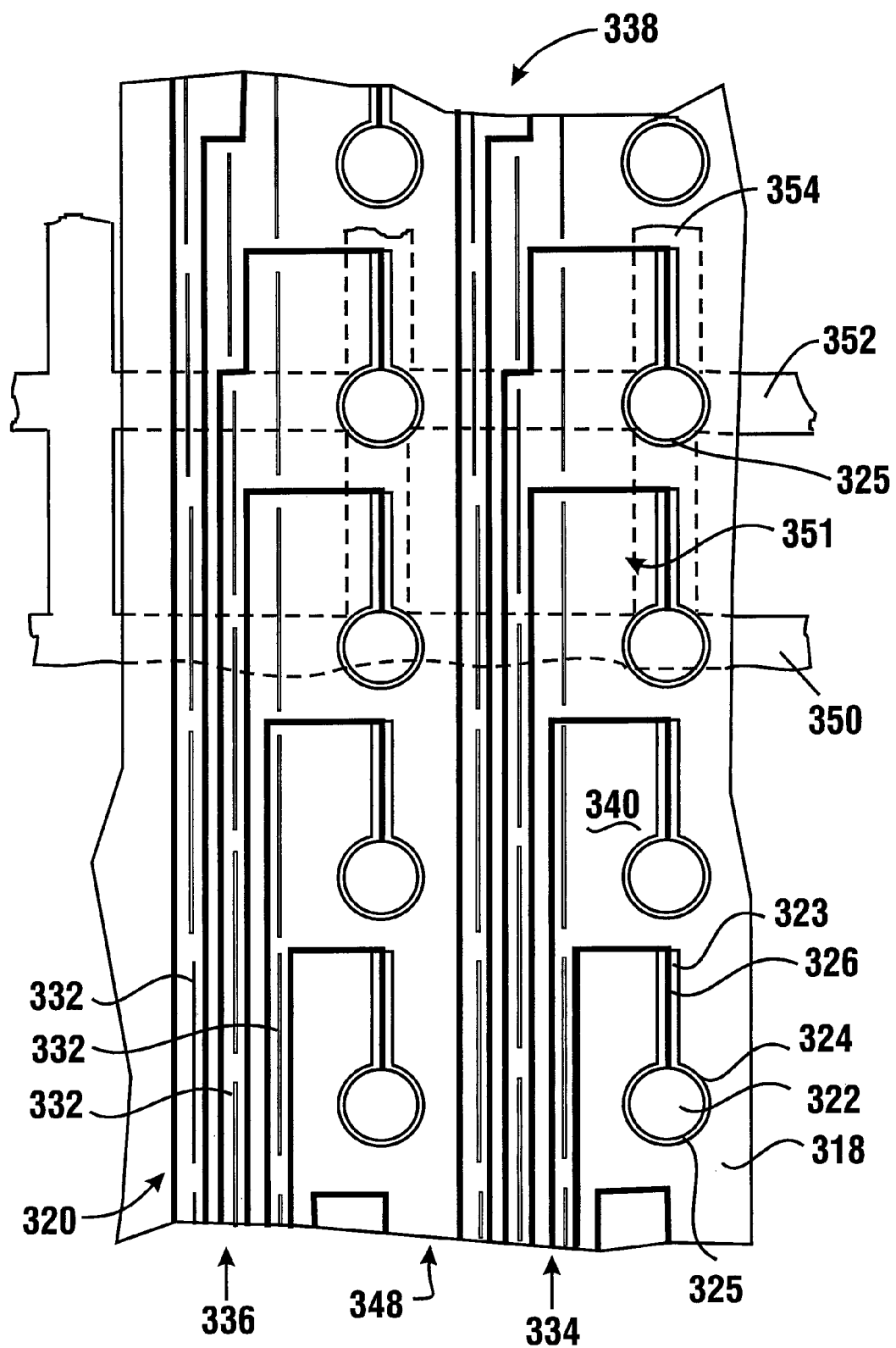
FIG. 46 schematically represents a portion of the flexible electrode array with a plurality of printed electrodes and trace lines with strategically cut perforations in the substrate for enhancing flexibility and extensibility of the electrode array.

FIG. 46 is representative of a portion of a flexible electrode array 320. In this exemplary embodiment of the array, the substrate 318 is strategically cut to include a plurality of cuts or perforations 324 through the substrate that are located along the outside perimeter of each printed electrode 322. In the exemplary embodiment the perforations extend through the substrate. However, in alternative embodiments, the perforations need not go all the way through the substrate.

Figure 47:
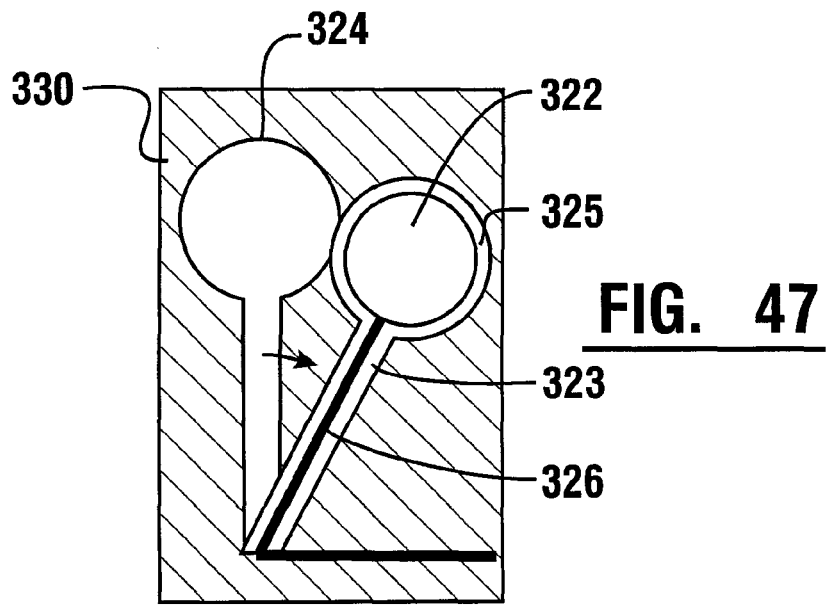
FIG. 47 is representative of a top plan view of the electrode array with the printed electrode flexing away from its original position cut in the substrate.

These perforations 324 also extend along each trace 326 adjacent an electrode 322 to form a stem portion 323 of the substrate that supports each trace. These perforations enable each printed electrode 322 and the electrode supporting portion of the substrate 325 to move in a plurality of directions with respect to the rest of the substrate 340, while remaining in electrical communication with the remainder of the electrode array. For example FIG. 47 shows a top perspective view of the printed electrode 322 and the electrode supporting portion of the substrate 325 that has been bent or flexed away from the perforation 324 in the supporting substrate 330.

When the entire flexible electrode array is placed on a patient's back, each electrode adheres to the skin of the patient's back. As the patient moves into different positions, the printed electrodes are operative to move with respect to each other in response to the patient's back muscles stretching or contracting.

Referring back to FIG. 46, this described exemplary embodiment also includes additional parallel perforations 332 in the substrate. These slits are grouped into a plurality of sets 334 and 336 which extend along the entire length of the substrate. These parallel perforations enable the substrate to stretch in one or more directions with the movement of a patient's back. Along with the perforations 324 around the individual electrodes, these parallel perforations 332 further enable the flexible electrode array to stretch or flex responsive to movement of back muscles, without individual electrodes being pulled away from their original positions on the patient's back.

As shown in FIG. 43, this described exemplary embodiment of the flexible electrode is protected by a removable cover sheet 301 that is placed on top of the array of printed electrodes 314. The hydrogel is sufficiently sticky to support the removable cover sheet 301 in place prior to the flexible electrode array being used. To separate the removable cover sheet 301 from the underlying array of electrodes 314, the cover sheet is typically peeled away from the flexible electrode array starting at the top 338 of the flexible electrode array.

As shown in FIG. 46 the perforations are located around the electrode 322 and trace 326 such that the stem portions 323 of the substrate are oriented in a common direction. One advantage of this particular pattern, is that when the removable cover sheet 301 is pealed away starting at the bottom 338 of the flexible electrode array 320, the printed electrodes will not be pulled away from the base substrate 340 at an odd angle which may tear the electrode supporting portion 325 and/or stem portion 323 from the remaining portions of the substrate 340.

This described embodiment of the flexible electrode array also encompasses a release sheet adhesively attached to the substrate on the side opposite the previously described cover sheet 301. As shown in FIG. 46, the release sheet 350 includes a plurality of rectangular apertures 351 which result in the release sheet having of a grid pattern with a plurality of rows 352 and columns 354. The rows and columns are positioned along the release sheet 350 to intersect with the electrode supporting portions 325 of the substrate. The release sheet is attached to the substrate 340 with a removable/repositionable adhesive.

For this described exemplary embodiment the flexible electrode 348 array is sandwiched between the cover sheet and the release sheet 350. This configuration helps protect the flexible electrode array during shipment. When a clinician applies the flexible electrode array to a patient, the cover is first removed; however, the release sheet is left on the flexible electrode array. As the clinician aligns the flexible electrode array 348 on the patient's back, the release sheet 350 prevents the electrode supporting portions 325 from moving relative to the substrate 340. Once the flexible electrode array is positioned correctly on the patient, the release sheet is removed.

In addition to applications for diagnosing back muscle problems, This described exemplary embodiment of the flexible electrode array can also be used in other types of diagnostic applications such as around body joints, the neck, a hand or foot, or any other area of the body that is operative to bend or flex or is curved. In such cases the pattern and sizes of electrodes can be printed on the flexible supporting sheet to suit the particular application. For instance, when diagnosing problems with a hand such a carpel tunnel, the supporting sheet could be cut in the shape of a hand. Individual electrodes may then be printed along portions of the supporting sheet to correspond with fingers, the back of the hand, and the wrist. For other body parts, other shapes and patterns of electrodes can be used.

The exemplary embodiment of the flexible array as shown in FIG. 43, includes a pair of connection ends 296 and 298. Each of the electrical trace lines terminates at one of these connection ends. To aid in the coupling of the trace lines to an external electrical connector, the trace line ends in connection points 299 which have an exposed electrically conductive surface and have a size that is operative to mate with electrical contacts of an electrical connector.

To help protect the exposed connection points 299 from damage during shipment and storage and from accidental contact with a ground or voltage source, the connection ends 296 and 298 include tail flaps 360 and 362. As shown with reference to tail flap 362, only an end portion 366 of the tail flap 362 is attached to the connection end 298. The tail flap 362 is comprised of a flexible material that enables the portions of the tail flap 362 above the connection points to be lifted away from connection points 299. In this described embodiment the tail flap 362 includes tabs 370, and 372 which assist in lifting the tail flap by hand or by an electrical connector when the connection end is inserted into an electrical connector.

Figure 48:
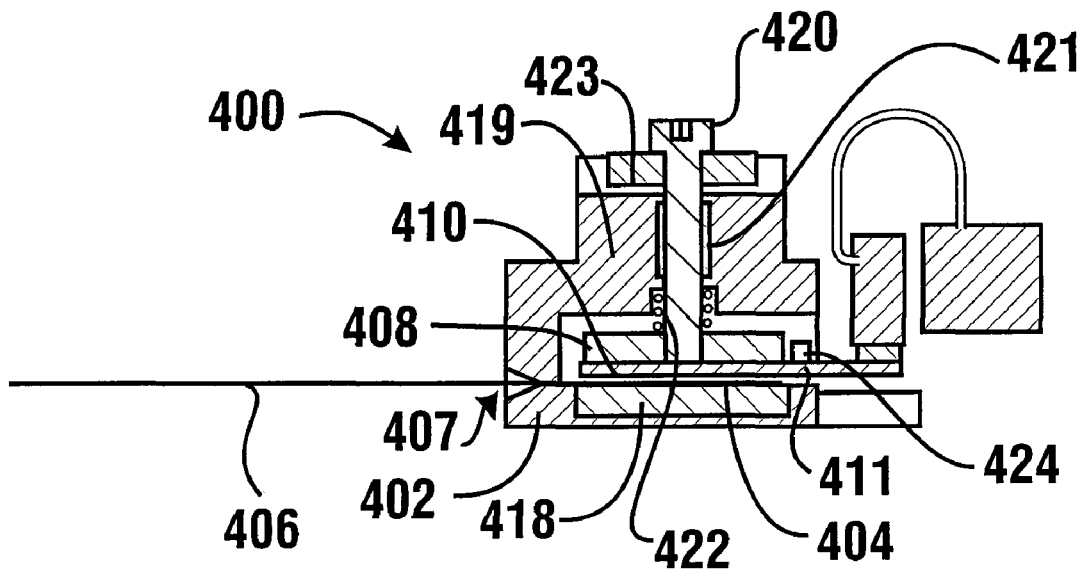
FIG. 48 is representative of a cross sectional side view of a electrode array connector.
Figure 49:
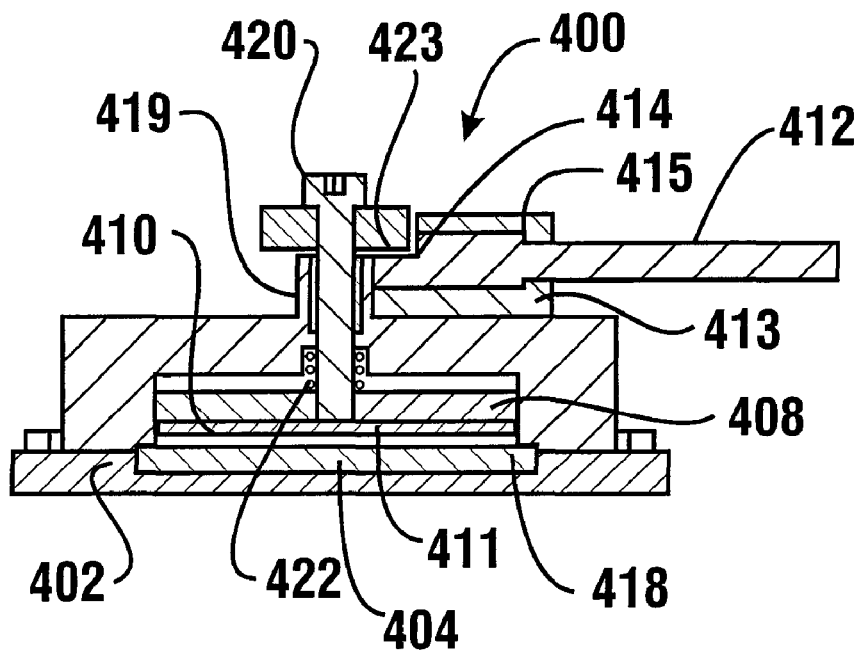
FIG. 49 is representative of a cross sectional front view of the electrode array connector.
Figure 50:
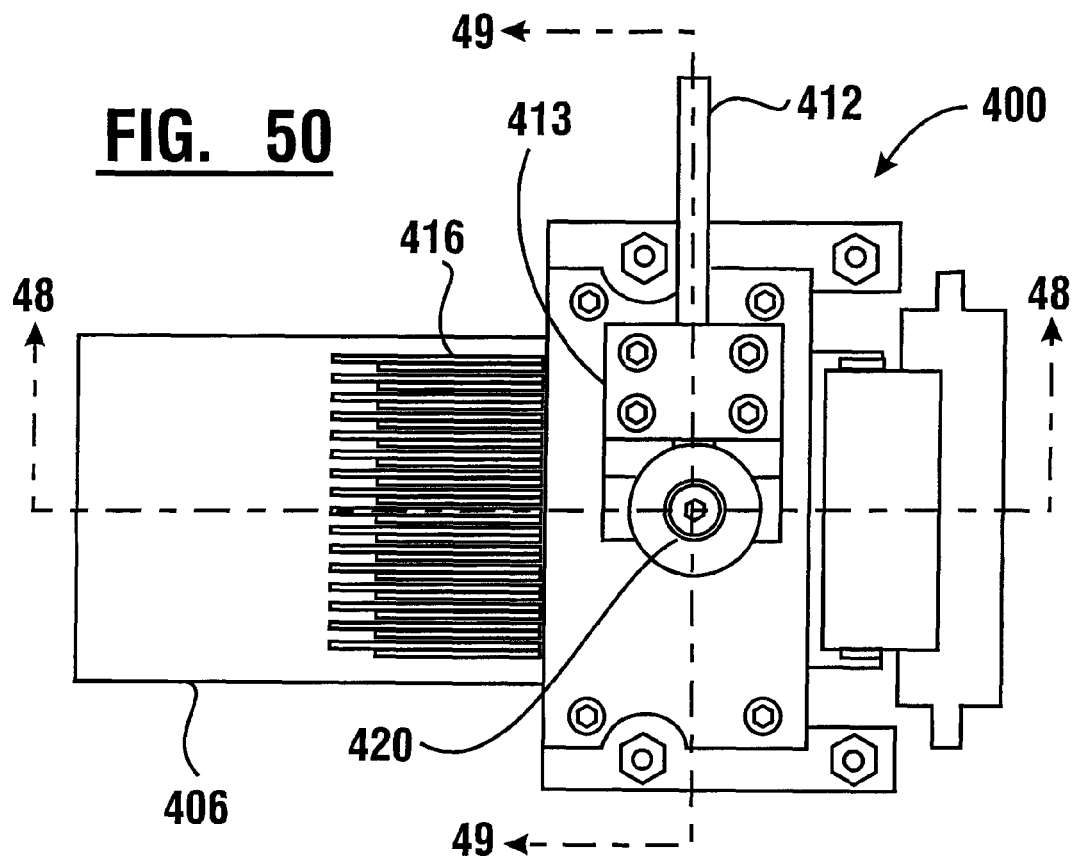
FIG. 50 is representative of a top plan view of the electrode array connector.

An exemplary embodiment of an electrical connector 400 is schematically shown in FIGS. 48-50. This exemplary connector 400 was specifically designed to mate with the connection ends of the flexible electrode array. The connector 400 is a ZIF connector so that wear is minimized between the connector 400 and the connection ends of the flexible array. This extends the usable life of both the connector and the flexible array, thus enabling many mate-demate cycles.

FIG. 48 shows a side plane view of the connector 400 which includes a base member 402. The base member includes a first surface 404 that accepts the connection end 406 of the flexible array adjacent to the first surface 404. The connector 400 also includes a head member 408 that is operative to move with respect to the base member 402. The head member 408 includes a second surface 410 that faces the first surface 404 of the base member 402.

The head member 408 is operative to move between a closed position and an open position. In the closed position the head member 408 is operative to clamp the connection end 406 between the first and second surfaces 404 and 410. When the head member 408 is in the open position, a throat area 407 is formed between the first and second surfaces 404 and 410 with sufficient space to enable the connection end 406 to freely move in and out of the throat area 407.

The connector further includes head guide 419 with a head bore 421 therethrough. The head member 408 includes a follower member 420 that extends in a direction opposite of the second surface 410 and through the bore 421. The follower member 420 is operative to slide back and forth within the head bore.

In the exemplary embodiment, the head member is biased toward the closed position with a spring 422 located between the head guide 419 and the head member 408. However, in alternative embodiments the head member may be biased in the open position.

As shown in FIG. 49, the connecter further includes a shaft guide 413 with a shaft bore 415 therethrough. The shaft bore is sized to accept a shaft member 412 therethrough. The shaft member 412 is operative to rotate within the shaft bore 415. The shaft member includes a cam surface 414 that is in slidable contact with a cam follower surface 423 of the follower member 420. As the shaft member turns, the cam surface 414 is operative to urge the follower member 420 to move within the head bore 419, which in turn moves the head member 408 away from or toward the base member 402.

Figure 51:
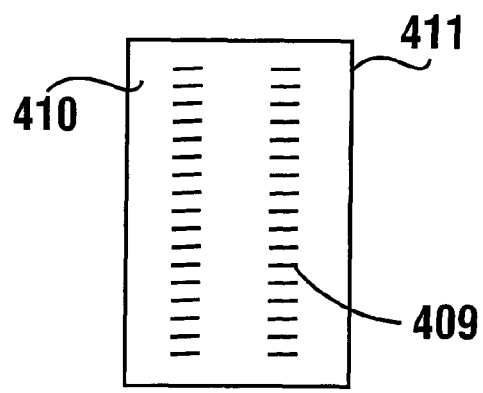
FIG. 51 is representative of a bottom plan view of a head member of the electrode array connector.

As shown in FIG. 50, the connection end 406 of the flexible array includes a plurality of traces 416. As shown in FIGS. 48 and 49, the second surface 410 of the head member 408 includes a printed circuit board 411 with a plurality of electrical contacts 409. As shown in FIG. 51, these electrical contacts 409 are arranged in a predetermined pattern that corresponds to the location of the ends of the traces 416. When the connector end 406 is clamped between the first and second surfaces 404 and 410, each electrical contact 409 on the printed circuit board 411 is in electrical connection with a corresponding trace 416.

Although the exemplary embodiment has electrical contacts located on the head member 408, in alternative exemplary embodiments, the electrical contacts 409 may be located on the base member 402 or located on both the head and base members 402 and 408.

In the exemplary embodiment of the connector the first surface 404 of the base member 402 includes a layer of foam 418. When the connection end 406 is locked between the head and base members 402 and 408, the foam 418 is operative to direct the clamping force of the connector evenly across the back of the connection end to achieve good electrical connections between each of the electrical contacts 409 and the traces 416.

To further aid the alignment of the traces 416 with the electrical contacts 409, the connector includes one or more guide pins 424 as shown in FIG. 48. This guide pins 424 are positioned on the base member 402 and are operative to guide the edges of the connection end 406 to positions that will achieve the proper registration between the traces 416 and electrical contacts 409.

Figure 52:
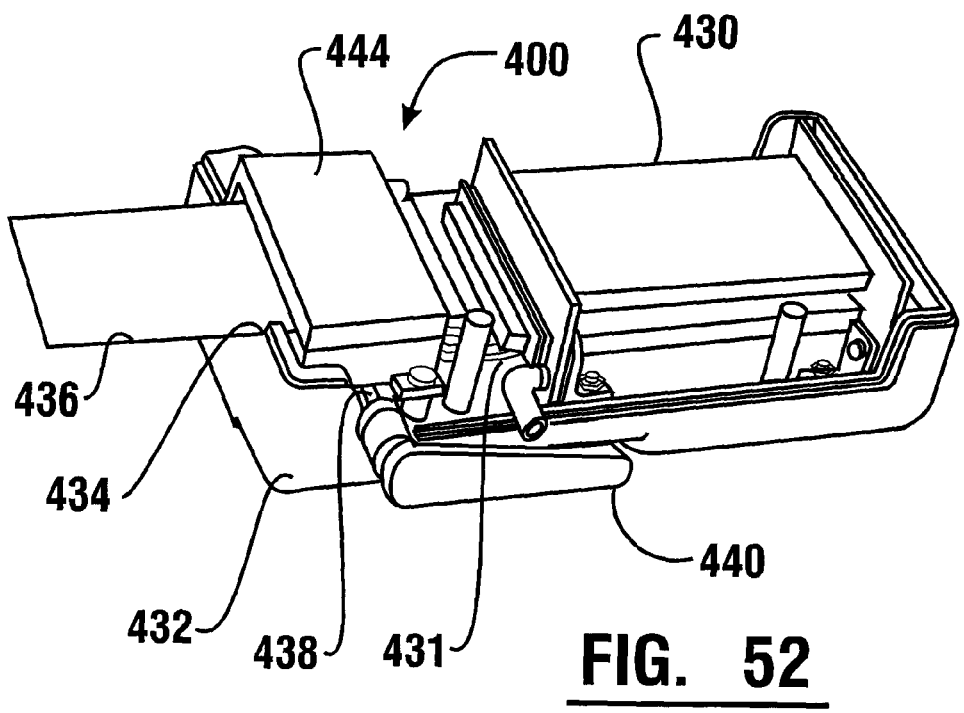
FIG. 52 is representative of an isometric view of a buffer/amplifier coupled to the electrode array connector.

As shown in FIG. 52 a buffer/amplifier 430 is connected to one of the described exemplary connectors 400 to enable the electrical coupling of a flexible array connection end 436 to the buffer/amplifier 430.

For the exemplary embodiment, both the buffer/amplifier 430 and the connector 400 are located in a common housing 432. Each of the electrical contacts in the connector are in electrical connection with the buffer/amplifier 430 through a cable 431. The housing includes a slot 434 that enables the connection end 436 of a flexible electrode array to pass through the housing and slide adjacent the base member 444 of the connector 400.

Figure 53:
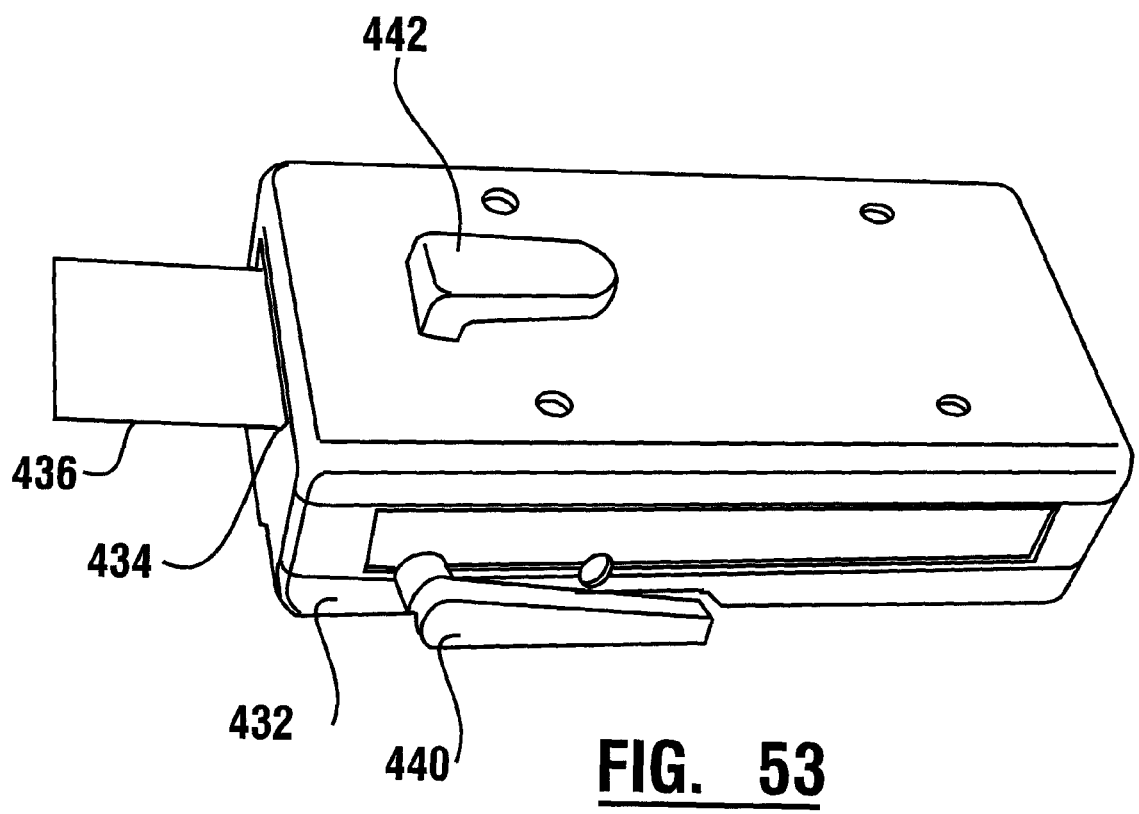
FIG. 53 is representative of an isometric view of a housing enclosing the buffer/amplifier coupled to the electrode array connector.

In this described embodiment the shaft member 438 of the connector includes a lever 440 that extends outside of the housing. The lever 440 is operative to rotate the shaft member 438 backward and forward, which in turn moves the head member between the open and closed positions. As shown in FIG. 53 the housing 430 may include a clip 442 that enables the buffer/amplifier 430 to easily attach to a belt around the torso or hips of a patient. This allows the buffer/amplifier 430 to be easily positioned as close as possible to the origin of the EMG signals being collected from the patient.

The EMG diagnostic system will now be further described with reference to use of the sensor pad 10 and electrode 28. It should be understood that except as otherwise specified other EMG sensor devices may be used in a comparable manner to that discussed herein.

Once sensor pad 10 has been located in position on a patient 48 and secured by support belt 49 and electrical interconnection made with electronic apparatus 22, the patient can be moved about and put through a series of different positions in order to develop a series of signal groups indicative of the underlying musculature. Typically, these positions are neutral, flexion, extension, left flexion, right flexion, left rotation, right rotation, sit, supine and prone, although various modifiers or alternatives may be added to or deleted from these positions. In each of the positions a scan of the electrodes 28 is made, each scan requiring only 1-10 seconds, and the signal information retained for later utilization in electronic apparatus 22.

Electrical signals from electrodes 28 are connected by way of wires 40, buffer amplifier 42, filters 43, 44 and cable 45 to analog to digital (A/D) converter 24 and then to computer 25 for analysis and conversion. The data from sensor pad 10 is collected in pseudo differential fashion, each electrode 28 being sampled relative to reference electrode 61 located in the center of pad 10. Subtraction of electrical data yields the wave form between the two electrodes of interest and the wave form is subjected to a root mean square (RMS) analysis over a predetermined time interval to yield a discrete number indicative of the signal strength. In one example of utilization of the signals, the RMS number is converted to a representative color indicia and that color indicia is displayed on the screen of display unit 26 in a location representative of the particular two electrodes 28 of interest. This data is preferably scaled or otherwise conformed to correspond to the anatomy of the patient as previously discussed using suitable scaling software in the computer.

Figure 7:
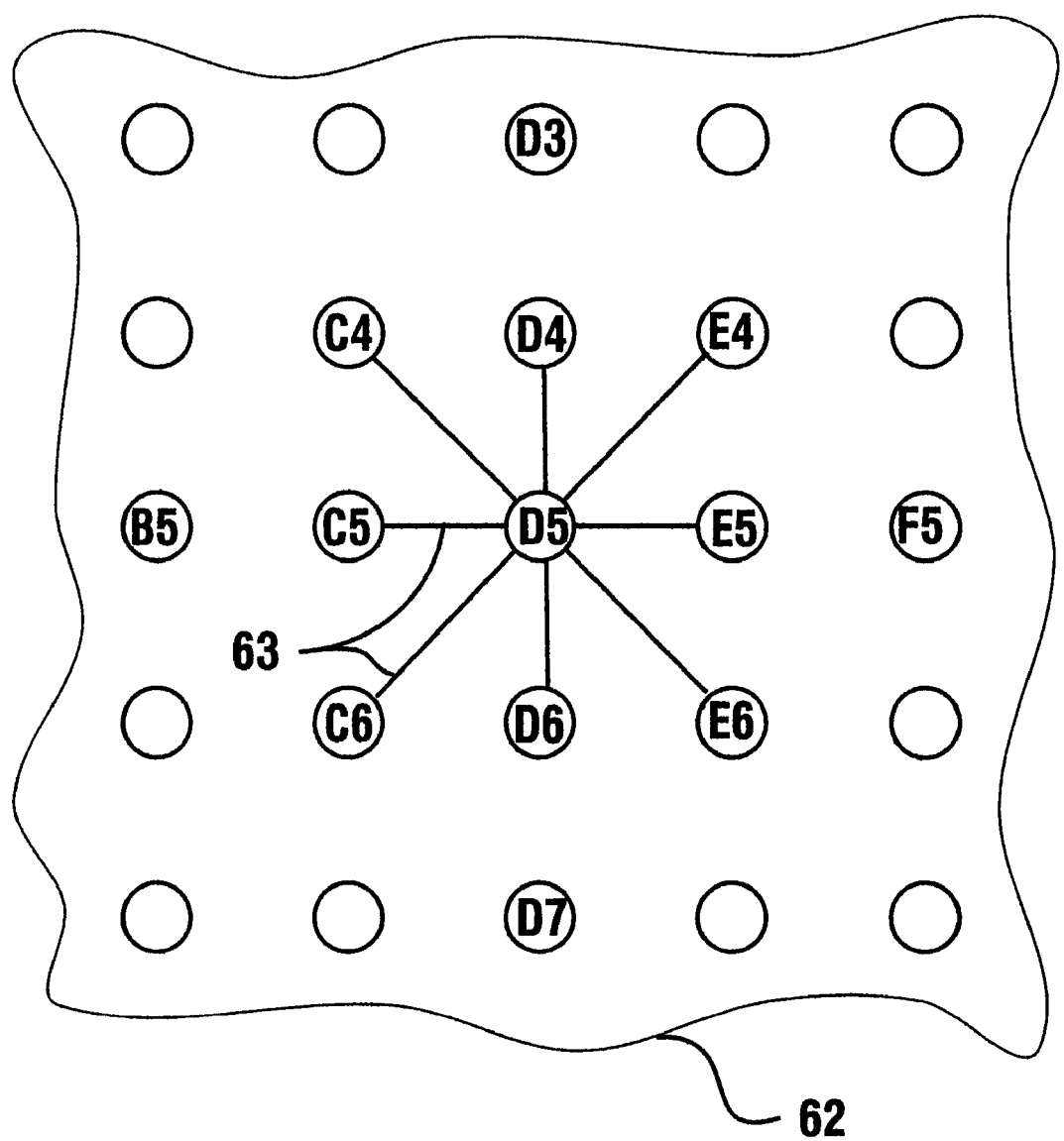
FIG. 7 is a schematic view of the screen of the display unit of an exemplary embodiment depicting the location of a portion of the electrodes of the sensor pad as circles and showing several interconnecting color bars.

This technique of measurement may best be seen in the FIG. 7 representation of a portion of the screen 62 of display unit 26. Here the electrode positions are represented by circles with alphanumeric designations therein, with the seven columns of electrodes 28 designated from A-G and the nine rows designated from 1-9. Thus, various electrode positions are shown, for example, as C4, D5, E6 with D5 representative of the reference electrode 61 position. Intermediate computer generated light bars or line segments 63 interconnect various ones of the adjacent electrode positions, i.e., C5-D5 and C6-D5 to represent the pattern of image generated by computer 25 and displayed at screen 62 of display unit 26.

Figure 3:
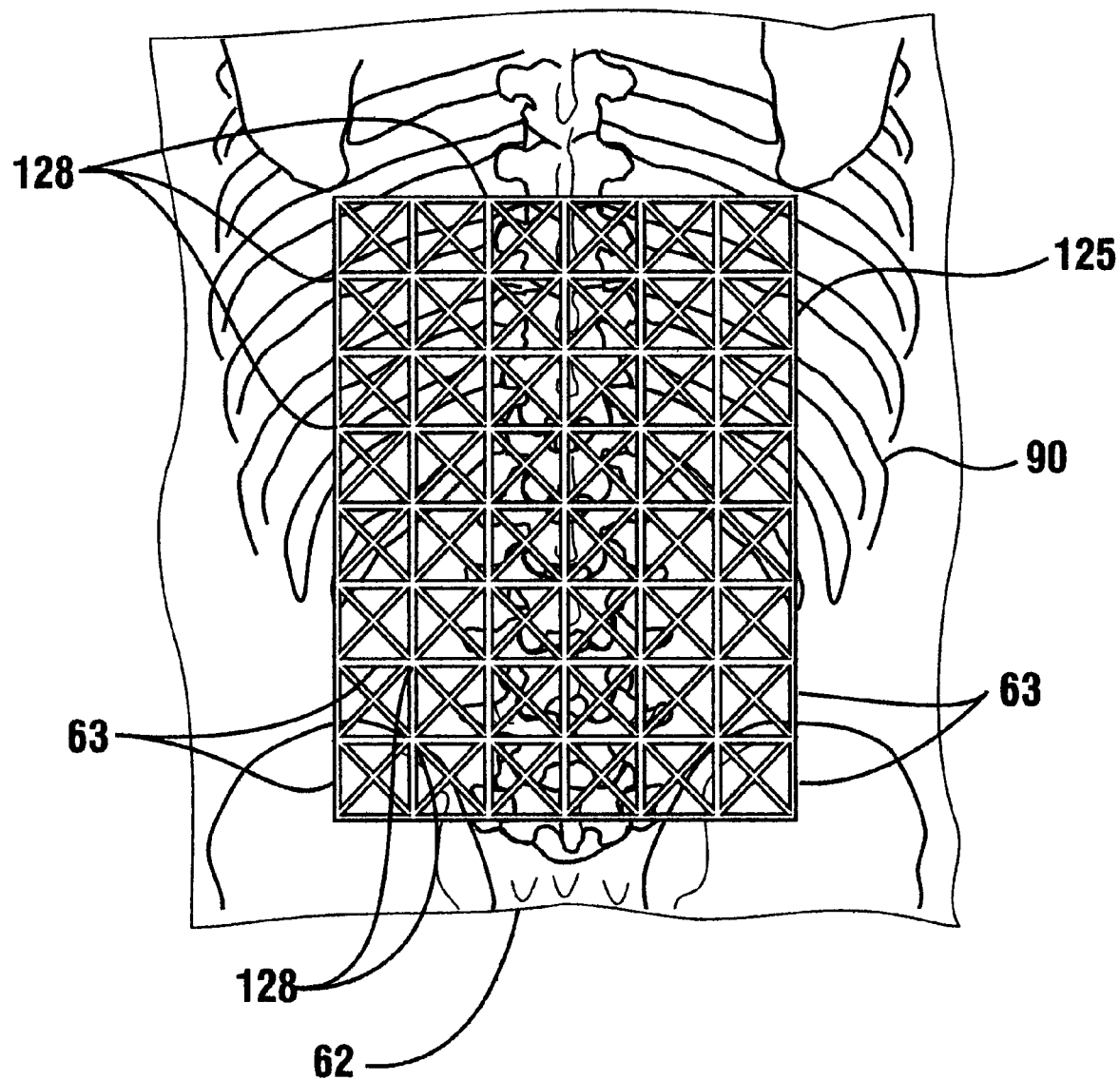
FIG. 3 is a schematic view of the screen of a display unit of an exemplary embodiment showing a full color bar matrix overlay in relation to the lower back skeletal anatomy of a human patient.

A full pattern display is shown in FIG. 3 wherein the screen 62 of display unit 26 shows the full array of light bars 63 interconnecting all of the electrode 28 positions, in a matrix overlying a display of the lower back skeletal anatomy 90 of the patient 48. This view demonstrates the spatial relationship among the locations of electrodes 28, the visual display of light bars 63 and the patient 48 anatomy 90 in a manner that can be readily visualized and utilized by the examining physician. It will be described in greater detail hereinafter that the light bar 63 display can be adjusted or modified by the physician, or automatically by the computer to produce effects including a more limited visual display of light bars 63, or variations in intensity, hue or colorization thereof to enhance the desired display. Further, it will be shown that instead of the skeletal structure 90 of the patient 48, various depictions of the standard musculature of the patient such as those templates shown in FIGS. 15-23 can be made to induce a correlation between the signals being obtained from the sensing electrodes and the specific musculature creating the abnormal condition affecting the patient.

In a scan of the complete array of electrodes, 206 color or grayscale light bars are produced on display unit 26 in positions delimited by and corresponding to the positions of the electrodes 28 on sensor pad 10. Also superimposed on display unit 26 is a graphical depiction of the musculature of the lower back of patient 48 with correlation between the two being achieved by the registration process previously described where a sensor pad is located relative to the tenth thoracic vertebrae 18 and the PSIS identifying crests 12, 14 or the L4 vertebrae, and using appropriate scaling.

In an exemplary embodiment, the diagrams of the musculature of FIGS. 15-23, may be shown at the screen of display unit 26 as a series of images, each representative of certain muscle groups of the lower back of patient 48 so that the attending physician might make a correlation between the colors and/or levels of intensity which represent the strength of contraction of the muscle underneath the electrode and the particular muscles or muscle groups, and discern what muscle is causing the particular colorization patterns being produced. It is apparent as well, that it would be possible to program computer 25 to recognize abnormal signals from the electrodes 28 being polled to provide some other indication of the abnormal situation using different evaluation techniques. It is also apparent that the signals collected from electrodes 28 can be stored in a database and processed in different ways, perhaps at later times or printed out in hard copy, if this is a desired result. The capture of data from all of the electrodes 28 occurs substantially simultaneously and is stored in computer 25 for manipulation in a myriad of possible ways, only certain of which are described herein.

Referring now to FIGS. 10-13, there are shown several variations of the techniques for monitoring and analysis of the electrical signals derived from electrode 28. As previously described, each electrode 28 is scanned relative to reference electrode 61 to develop a signal representative of the voltage level detected at the site of the particular electrode, and data representative of the signal retained in computer 25. In further processing of the signals, each signal may be compared to that of other electrodes to develop signal patterns representative of the muscle condition being evaluated. For example, FIG. 10 is a representation of signals developed at sensor pad 10 when only a depiction of a discrete dot is made at the location of each electrode 28, with no showing of color or grayscale bars. This display might be most useful in achieving a desired registration between electrode 28 display and the skeletal structure 90 display.

FIG. 11 describes a first variation for analysis of the signals where the signal of each electrode 28 in the first row 64 is compared to the corresponding electrode 28 in the same column, in the second row 65 to develop a resultant signal, represented at display unit 26 as a bar 66 joining the location of the particular electrodes. In this manner a full pattern of vertical bars 66 is developed, although only a portion is shown, with each being a unique color or grayscale and representative of the signal comparison at each electrode pair. Such arrangement of color or grayscale bars 66 may be displayed juxtaposed to patterns of muscle structure as previously described, and likely is more useful in displaying an association with muscles or muscle groups which are oriented generally vertically in the back of the patient.

FIGS. 12 and 13 represent yet other variations of signal analysis wherein different herringbone patterns of signal are derived. In FIG. 12, for example, the signal of center electrode 70 in the second row, center column (D2) is compared with electrodes 71, 72 in the first row and adjacent columns (C1) (E1) to develop intermediate color or grayscale bars 74, 75 respectively, indicative of the comparison of the electrode signals. Further color or grayscale bars corresponding to bars 74, 75 are developed throughout the array of electrodes 28 to achieve an overall pattern for display at display unit 26. Again, only a portion of the display is depicted in FIG. 12, for purposes of clarity.

FIG. 13 is yet another variation of a display that may be produced using this technique of monitoring. Here an inverted herringbone pattern consisting of color or grayscale bars 78 is achieved when the signals from electrodes 28 are compared in the described pattern. For example, electrode 79 in the first row, center column (D1) is compared to electrodes 80, 81 in the second row in adjacent columns (C2) (E2) to produce the intermediate color or grayscale bars 78. When extended throughout the array of sensor pad 10, a colored or grayscale herringbone pattern of color or grayscale bars 78 is achieved for comparison with muscle pattern displays shown in association therewith.

It is apparent that still further comparisons can be made of the signals obtained from electrodes 28, for example to compare the signal of each electrode 28 with the signals of all adjacent electrodes 28, and electronically summarize the information obtained and to produce a representative color or grayscale pattern of the results for visualization at the face of display unit 26.

Similarly, it is apparent that the resultant electrical signals from electrodes 28 and the resultant color or grayscale information can be shown at display unit 26 in different formats to emphasize the relationship between developed signals and the underlying muscle structure. With a suitably high speed computer 25, the images of differing muscle structures can be shown in association with the color or grayscale patterns as directed by the physician to provide a correlation between the patterns and the abnormal muscle elements.

It will further be understood that in various embodiments different forms of the display may be used including arrangements of various types of pixels or other types of icons or designators which are indicative of levels of muscle activity. While coloration may be used as an exemplary indicator in the diagnostic tool for purposes of correlating muscle activity and underlying anatomy, as discussed previously, other visual outputs such as grayscale images may be provided which do not involve coloration for clinicians who suffer from color blindness. Such outputs may involve varying patterns of a monochrome nature which are indicative of levels of muscle activity. Alternatively embodiments may include other types of output devices which enable the discrimination of levels of muscle activities. Such output devices may also output indicia representative of the underlying muscle topography. This may include for example output devices usable by the visually impaired such as pin array type output devices in which arrays of pins are movable relative to one another to produce surface contours. Such arrays may be produced with sufficient numbers of pins and pin densities to provide contours indicative of underlying musculature as well as electrical activity. Such devices may be multiplexed between received signals and data representative of underlying musculature to facilitate comparison through touch of muscle contour and areas of muscle activity. Such output devices may be combined with visual and other type devices to facilitate diagnosis of conditions even by clinicians who do not have a visual impairment.

Figure 25:
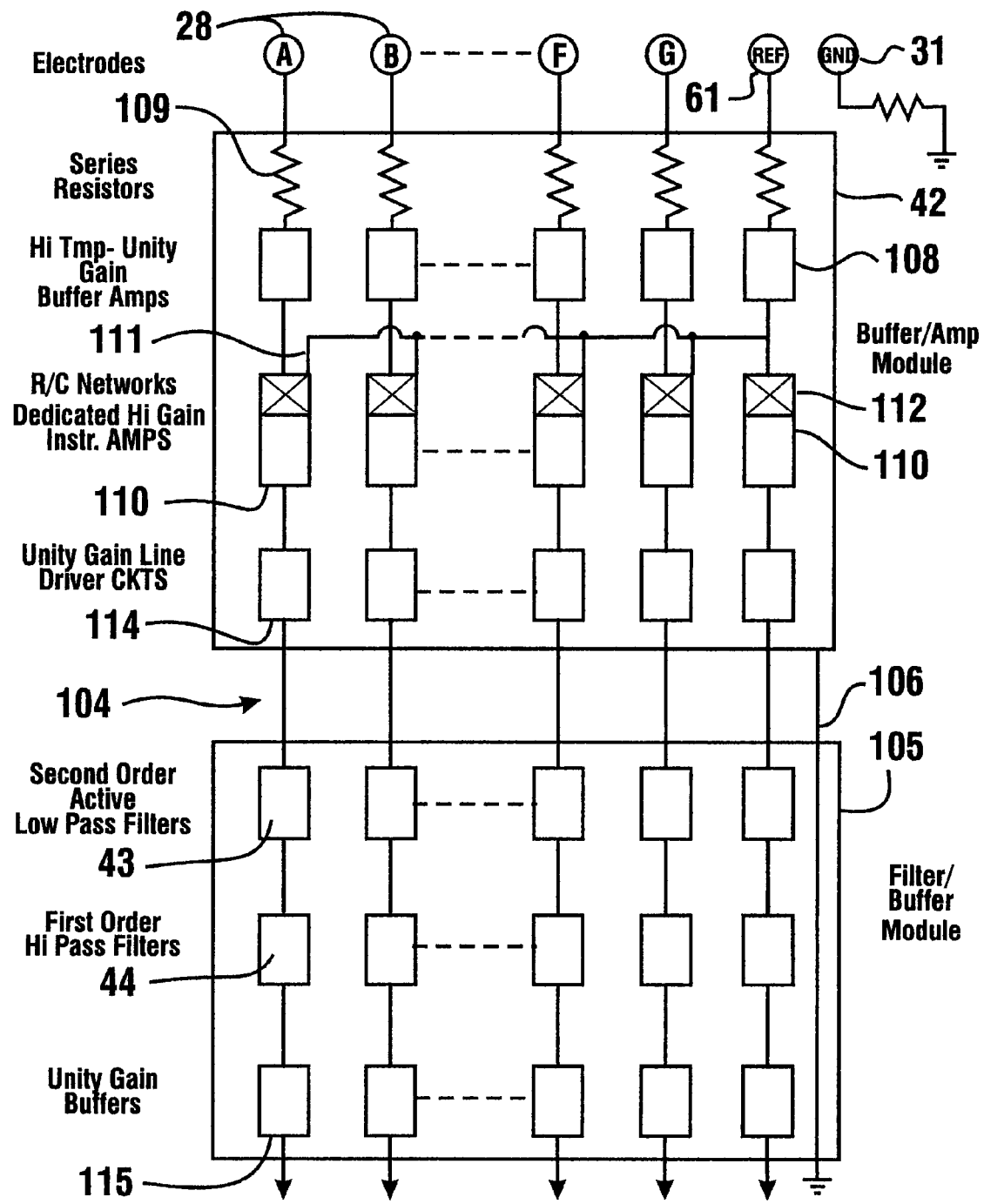
FIG. 25 is a schematic view of the components comprising the Analog Signal Conditioning Subsystem of FIG. 24.

Referring now to FIGS. 24 and 25, there is shown in more detail the components comprising the analog and digital signal portions of one exemplary embodiment including electrode subsystem 100, analog signal conditioning subsystem 101, and signal processing subsystem 102. Electrode subsystem 100 comprises the array of sixty-three electrodes 28, only a few of which are shown and labeled as A, B, F, G, Ref. and Gnd. in correspondence with previous descriptions. Wires 40 connect electrodes 28 to buffer amplifier 42, shown in block form on FIG. 24 and in more detail in FIG. 25.

A long shielded interconnect cable 104 connects the outputs of buffer amplifier 42 to more remotely located Filter/Buffer module 105 which includes low and high pass filters 43, 44. In turn, a short shield cable 45 completes the analog signal portion, being connected to analog to digital converter card 24 in computer 25, the latter components being essential parts of the signal processing subsystem 102. As indicated, a single continuous shield path, depicted by dashed lines 107, is established between Buffer/Amplifier module 42 and computer 25, assuring that minimal interference is generated in the signals of interest from extraneous sources.

The enclosures used for the Filter/Buffer module 105 and the Buffer/Amplifier module 42 are shielded with a layer of conductive material. All enclosure shields are connected in series with the interconnect cable shields, resulting in a single continuous shield path from the Buffer/Amplifier input connector to the data acquisition computer 25 chassis ground.

The array of electrodes 28 mounted on sensor pad 10, as previously described, must conform to the human back, ensure consistent electrode impedance with the skin, not interfere substantially with patient movement, and be easy to use. The electrodes 28 in this described exemplary embodiment are in a nine row by seven column configuration and the sensor pad 10 is held in place with a fabric brace with or without pressure sensitive adhesive. Of course other configurations of electrodes may be used in other embodiments. Likewise the disposable type and reusable adhesive type sensor arrays discussed previously may be used.

The analog signal conditioning subsystem 101 provides buffering, voltage amplification and analog filtering for the array of electrodes 28. In one embodiment one electrode in the array is designated as the reference electrode 61, and all other electrode voltages are measured with respect to the reference electrode 61. Other embodiments may employ other approaches for acquiring signals indicative of relative levels of electrical activity.

Each of the electrode 28 signals is connected by way of wires 40 to high impedance, unity gain buffer amplifiers 108 by way of a 10K Ohm series resistor 109. The purpose of resistor 109 is to provide a measure of resistive isolation for safety purposes, as well as to increase the electrostatic discharge (ESD) immunity of the amplifier.

Following the buffer amplifiers 108, each channel has a dedicated high gain instrumentation amplifier 110. The inverting input of each instrumentation amplifier 110 is connected to the buffered signal from the reference electrode channel as shown by connector 111. Thus, the output of each instrumentation amplifier 110 represents the voltage of a given electrode with respect to the reference electrode 61. RC networks 112 connected to the inputs of the instrumentation amplifier 110 serve as low pass filters to block unwanted high frequency signals. The outputs of the instrumentation amplifiers 110 feed into unity-gain, line-driver circuits 114 that are capable of driving the capacitive load of the long shielded interconnect cable 104, without oscillation.

The ground electrode 31 is connected to the patient and is connected to ground through a resistor. In one exemplary embodiment electrode 31 is connected to the analog signal ground on the digital converter card through a one million Ohm resistance. The exemplary form of the analog to digital converter card 24, is a sixty-four channel multiplexed converter capable of operating in pseudo-differential input mode. The Buffer/Amplifier module 42 and Filter/Buffer module 105 are each connected to ground as represented by line 106.

Each of the sixty-three signal inputs into Filter/Buffer 105, via cable 104, is connected to a second order active low pass filter 43. The output of low pass filter 43 is connected to the input of first order, high pass filter 44. The output of each high pass filter 44 is connected to unity gain buffer 115 that is capable of driving the capacitive load of the analog to digital converter card 24 interconnect cable 45, without oscillation. Electronic power for Filter/Buffer module 105 is provided by an external linear power supply. Filter/Buffer module 105 provides power for Buffer/Amplifier module 42 via the interconnect cable 104. Ground sense line 106 from the Buffer/Amplifier modules 42 passes directly through the Filter/Buffer module 105.

Figure 26:
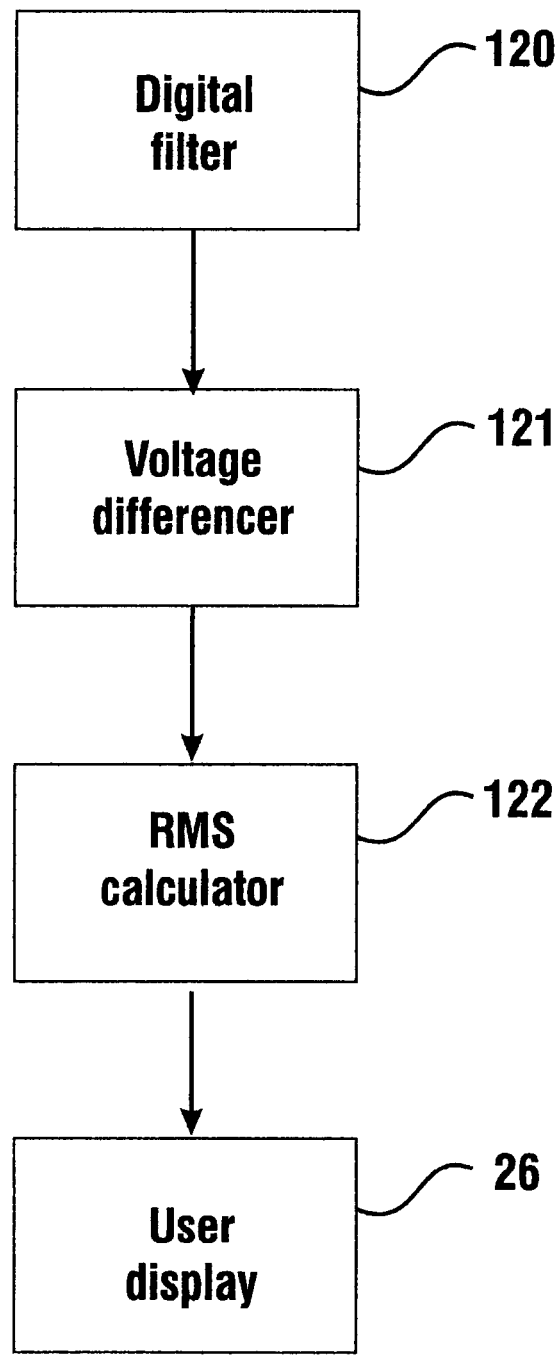
FIG. 26 is a schematic view of the components comprising the Signal Processing Subsystem of FIG. 24.

Signal processing subsystem 102 is shown in block diagram form in FIG. 26 and consists of the major elements of a digital filter 120, voltage differencer 121 and RMS calculator 122. First, digital filtering techniques are used to reduce noise on the measured signal. Next, a voltage differencer 121 determines the voltage waveform between all adjacent electrodes 28. Finally, the root-mean-square (RMS) voltage between all adjacent electrodes is calculated and used to characterize the level of muscle activity between adjacent electrodes. The signal processing subsystem is preferably implemented in software on a PC-compatible computer 25.

The digital signal conditioning system consists of high pass, low pass and band-cut digital filters incorporated into the data analysis software. The high and low pass filters are designed to reject signals outside of the frequency range of interest, and have amplitude rolloffs of 80 dB/decade. The primary purpose of these digital filters is to block common-mode error signals introduced near the corner frequencies of the analog filters. The band-cut or notch filter drastically reduces 60 Hz signals, in order to eliminate unwanted pickup of power line emissions. In an exemplary embodiment, oversampling is used which interpolates additional pseudo sample points between actual sample points to improve performance of filters, for example to achieve good frequency discrimination in the 60 Hz notch filter. In one exemplary embodiment 10x oversampling is used.

The output of the electrode voltage data acquisition subsystem consists of a set of voltage waveforms of each electrode 28 with respect to a particular reference electrode. The voltage differencer 121 computes the voltage waveform between each pair of adjacent electrodes (vertically, horizontally and diagonally) by differencing the voltage waveforms for the two adjacent electrodes. RMS calculator 122 provides the RMS value of each adjacent electrode pair waveform as a scalar number which is computed from the waveform using a conventional RMS calculation.

The user display subsystem 26 presents the processed data to the practitioner in a readily understandable format. In the described embodiment the data is displayed as images on a screen or other visual output device. Of course as discussed previously, in other embodiments other output devices may be used. A digitized illustration of a muscle layer in the human back as shown in FIGS. 14-23 is used as the background of the image. The user may select any muscle layer as the image background. A computer generated image 125 of the processed electrode 28 data is overlaid on the selected background illustration, and is spatially registered to that image. As previously discussed the spacial registration may be preferably achieved through scaling based on the dimensions of the patient input to the computer.

The electrode data image 125 in the described embodiment consists of colored or grayscale lines or light bars 63 drawn between the locations of each of adjacent electrodes 28, which are at each intersection 128 of each of the seven vertical columns and nine horizontal rows of light bars 63 as shown in FIG. 3 and as has been previously described. The color or grayscale (intensity level) of each line 63 indicates the value of the RMS voltage between the adjacent electrodes. The user can dynamically specify a maximum RMS value and a minimum RMS value which are used to map voltages to colors and/or levels of intensity. The resulting display is thus a false-color RMS voltage gradient field display, and is overlaid on and registered to the underlying muscle layer illustration. In an exemplary embodiment that uses color, the range of RMS values may be mapped from high RMS to low RMS in the following order: red, orange, yellow, green, blue. In an exemplary embodiment that uses levels of intensity (e.g grayscale), the range of RMS values may be mapped from high RMS to low RMS with grayscale values ranging respectively from black, through one or more shades of gray to white.

Figure 27:
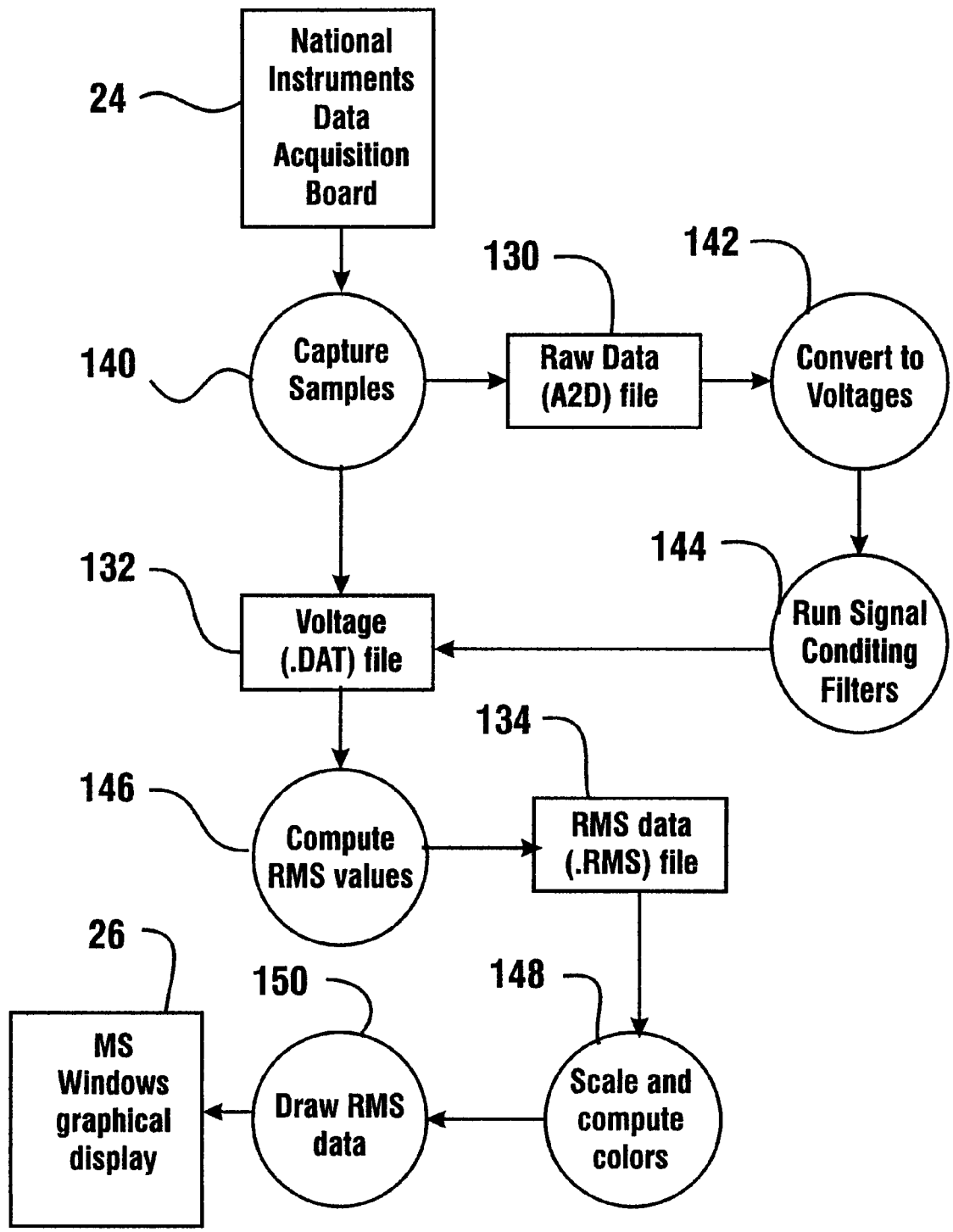
FIG. 27 is a logic diagram showing the data flow in the software of the system.

The software architecture of the signal processing system 102 is shown schematically in FIG. 27 as a diagram of the main data flow in the software. Essentially, this is a linear flow of computations, each of which takes a datum or file as input and generates a datum or file as output. Three types of data files are generated and stored and once created may be opened and displayed many times at later dates. The data files are described as well in FIG. 29 and comprise the Analog to Digital (A2D) file 130, Voltage (DAT) file 132 and Root Mean Square (RMS) file 134.

The format of header 135 for each of the files, 130, 132, 134 is depicted in FIG. 28 and in one embodiment contains information in an identical ASCII header format consisting of version information 152, patient information 154, which are the vital statistics on the patient being diagnosed, pad information 155 which provides specifics of sensor pad 10, calibration information 156, data acquisition settings 157 and display settings 158. The calibration information is derived after the sensor pad 10 location is determined on the back of the patient, being input by the operator to specify where certain parts of the patient's back are in relation to the electrodes on the pad, as previously described.

The A2D files 130 contain the actual analog to digital values at the output of analog to digital converter 24 which are collected during a test. Computer 25 scans all electrode channels rapidly enough to reconstruct the analog signal at all frequencies of interest. In one embodiment the minimum frequency of interest is about 30 Hz and the maximum about 150 Hz. The structure of the A2D files 130 is shown in FIG. 29 with each scan sample being stored in a two byte word in little endian format. The files 130 contain the analog to digital value and a header 135.

The voltage files 132 contain the voltage data from a test, after it has been converted from analog to digital values to voltages and signal conditioning filters have been applied. The voltage files 132 of this embodiment also contain the header 135 followed by the voltage values in the format shown in FIG. 29, each sample being stored as an IEEE double floating point value.

The RMS files 134 contain the RMS values of the differences between the voltage waveforms of adjacent electrodes 28. During display of an RMS file 134, the values can be mapped to colors or grayscale and displayed as colored or grayscale line segments or bars 63 at display unit 26.

Again, the RMS files 134 may contain header 135 followed by the RMS information. The RMS voltage difference is calculated for each pair of adjacent electrodes 28. The row and column position of each of the two electrodes are also stored in the format described in FIG. 29. Also included is information of the minimum and maximum RMS value in each scan and the total number of adjacent electrode pairs.

Summarizing then, the flow of data as depicted in FIG. 27 occurs as computer 25 generates signals to capture samples 140 from data acquisition board 24 at the input to computer 25 to create raw data or A2D files 130. Computer 25 then acts to convert the signals to voltage at 142 and run signal conditioning filters 144 to create voltage files 132. Computer 25 is then programmed to compute the RMS values at 146 and create the RMS data file 134. Subsequently, computer 25 operates to scale and compute color or grayscale values at 148, and then to draw the RMS data at 150 and eventually provide the color or grayscale bar matrix 125 depicted in FIG. 3.

The general architecture for the software operated in computer 25 can be seen from the source file 160 structure depicted in FIG. 30. The document view and visual interface 161 contain main initialization, menu and toolbar commands, message handlers and document/view commands. Dialog popups 162 allow for entering patient information, calibration information and the like and for editing various parameters. Further files include data acquisition, filtering and calculation 163, reading and writing header information and data 164, utilities 165, and bitmaps, icons and resource files 166. These routines are fairly typical for handling the information flow in the ways specified previously and are well understood in the art, not requiring detailed description herein. Further scaling software components for correlating the stored anatomical data to the anatomy of the particular patient is also preferably provided.

An embodiment of the previously discussed diagnostic system has been used to study the EMG data produced by the system for test subjects with no known back conditions to develop data associated with a normal back condition.

In this study, the above described flexible electrode array shown in FIG. 43 was used for the sensor device in the system. Each sensor device included a nine by seven, array of 63 surface electrodes spaced 1.2 centimeters center-to-center housed on the above described flexible substrate. The electrodes were numbered according to their row and column position (R, C) and referenced to the central electrode (5, 4). For each test subject, the electrodes were simultaneous applied to the lower back following anatomical landmarks associated with the respective test subject. As described previously the method for mounting the sensor device to each test subject included applying the array vertically with electrode (7, 4) over the L4 spinous process of the test subject. Then for each test subject the distances from the electrode (7, 4) on the L4 spinous process to the left lateral iliac crest and to the T7 spinous process were measured in centimeters to provide a scale corresponding to the respective test subject.

Although only 63 electrodes are in the array, bipolar information from 206 electrode pair combinations was obtained. The electromyographic activity between adjacent electrodes was collected by the system over one second and was converted to its RMS voltage. The RMS values were displayed by the system as proportionately colored bars. Using a 264-color spectrum, the highest RMS value was displayed in red, the lowest in blue. Remaining spectral colors were interposed. The resulting display represented the calculated myoelectric activity of the low back, with the highest RMS values (red) representing the region of greatest muscular activity.

In one study volunteers were selected who did not have a history of diabetes, thyroid disorders, or serious back injury (tumor, infections, trauma, herniated disc, or surgery to the spine) and who did not report experiencing any low back pain in the past 12 months.

A test subject was put through a standardized protocol that included monitoring the back with the test subject in three different positions of "upright", "flexion", and "weighted". For the upright position, each test subject stood at ease, feet shoulder-width apart, with arms at the sides. For the flexion position, each test subject stood as before with the anterior trunk bent forward at 20 degrees from vertical. For the weighted position, each test subject stood holding a three-pound dumbbells in each hand, directly in front of the body, at shoulder height with the elbows extended.

Images were obtained from each position three times for each patient. Each image contained 206 RMS values. The maximum RMS value in each image was selected. The average of this RMS value was calculated and recorded for each of the three positions. Age, sex, height, and weight were recorded for each test subject. Body mass index (BMI) was calculated as weight in kilograms divided by height in centimeters squared. BMI was analyzed as a continuous variable and assigned to one of three categories: up to 23, 23-27, and 27 and above. Pearson's correlation analysis, univariate regression, and model building multivariable regression method were applied to determine significance related to RMS values in each of the three test positions.

FIG. 54 shows a table derived from the data acquired from this study. Here the table shows normal reference ranges for maximum RMS values by body mass index and sex.

It was determined that RMS values were reduced proportional to body mass index (BMI) for both sexes in each test possibly because the myoelectric signals attenuated through adipose tissue. Also only BMI and gender were statistically significant independent predictors of RMS values in the upright| and flexion positions. BMI was a significant independent predictor of RMS values in the weighted position. As a result BMI was used to determine normal reference ranges from this data. Also sex was incorporated into the normal ranges determined for this data for the upright and flexion positions, but not in the weighted position.

Also, from this study it was determined that 73% of the test subjects (136 out of 186) demonstrated symmetrical myoelectric activity that originated at a single central focus centered on the spine.

Further studies have been performed using the same diagnostic system and protocol described above in example 2. These further studies have involved test subjects with known back conditions such as a facet condition and a disc condition. From the data generated by these studies, sets of predetermined EMG characteristics have been identified which correspond to these known back conditions. Such predetermined EMG characteristics correspond to different sets of features of EMG data which are usable to distinguish one back condition from another.

An exemplary embodiment of a method for using an EMG diagnostic system to distinguish between normal back conditions and one or more pain causing back conditions has been developed which uses this predetermined EMG characteristic data. In this embodiment, the method comprises acquiring data representative of EMG signals from a detection area on a back of a patient using a sensor device such as those described previously or any other device capable of acquiring EMG signals from a back of a patient. The method further includes evaluating the data acquired from the sensor device to determine EMG characteristics for the patient and determining whether predetermined EMG characteristics associated with at least one of a facet condition (e.g facet joint syndrome) and a disc condition (e.g. discongenic low back pain) and a muscle condition correspond to the EMG characteristics determined for the patient. Such EMG characteristics for a patient are also referred to herein as EMG data for the patient.

FIG. 55 shows a chart 500 of predetermined EMG characteristics for a plurality of back conditions 502 including: "normal", "muscle", "facet", "disc", "chronic pain-free", and "chronic exacerbation". It is to be understood that the back conditions listed in this table are only examples. Other embodiments may characterize different and/or additional back conditions.

The chart includes for each condition, characterization data (e.g. distinguishing features of EMG data) for each of a plurality of categories or types of EMG characteristics. These categories are shown in columns in the chart 500 and include an RMS category 504, a sequence category 506, a pattern category 508, a balance category 510, and a coefficient of variation category 512.

The RMS category 504 corresponds to how the maximum RMS voltage acquired from the sensor device for each of the three positions of the patient corresponds to the maximum RMS voltage for a normal back condition for each position. For purposes of making this determination, normal reference ranges for maximum RMS voltage values corresponding to each position for patients with normal back conditions and with a corresponding gender and/or body mass index (or a percent ideal body weight) may be determined from normal range data such as that shown in FIG. 54 or other data representative of normal levels of maximum RMS voltage for the particular type of sensor device used in the test. For each condition 502, the table shown in FIG. 55, shows in the RMS column 504 how the measured maximum RMS voltage compares (e.g. normal, above normal, below normal) to the normal range of maximum RMS voltage.

In an exemplary embodiment, the system may include software that is operative to calculate the maximum RMS voltage for the three positions. The software may also be operative to compare the calculated RMS voltages to data representative of predicted normal RMS voltages for similar patients. For example, the system may include a data store comprised of data (such as the data shown in FIG. 54) representative of ranges of RMS voltages for normal back condition for different types or characteristics of patients (e.g. gender, body mass index). In addition the software may be operative to output a determined characterization of the results of the comparison (e.g. normal, above normal, below normal).

This determination of normal, above normal, or below normal maximum RMS values may then be manually used to lookup one or more matching back conditions from the table such as shown in FIG. 55 to assist in identifying a back condition diagnosis for the patient. However, it is to be understood that in alternative exemplary embodiments, the software may be operative to correlate the determined characterization for maximum RMS voltage for a measurement to a corresponding predetermined characterization data stored in the data store for different back conditions to further the identification by the software of a back condition diagnosis for the patient.

As shown in FIG. 55, data associated with whether maximum RMS voltage is above or below a normal range or approaches the upper and lower limits of a normal range can be used to distinguish between a facet condition, a disc condition, and a muscle condition. For example, a facet condition may be identified as a possible condition when the maximum RMS voltage is determined to be below a predetermined normal range for the patient. Also a disc condition may be identified as a possible condition when the maximum RMS voltage is determined to be in the upper or elevated range for normal RMS voltages. In addition a muscle condition may be identified as a possible condition when the maximum RMS voltage is determined to be above a predetermined normal range for the patient.

With respect to the table shown in FIG. 55, the sequence 506 category corresponds to the sequence of positions (e.g. upright, flexion, and weighted) placed in an order based on the maximum RMS voltages measured for each position. For a normal back condition, the typical order as shown in FIG. 55 (irrespective of sex and BMI) from low to high maximum RMS voltage is: upright, flexion, and weighted. Thus for a normal back condition, the sensor device typically produces a maximum RMS voltage for the patient in the flexion position that is greater than when the patient is in an upright position. Also for the normal back condition, the sensor device typically produces a maximum RMS voltage for the patient in the weighted position that is greater than when the patient is in the flexion position.

As shown in FIG. 55, a muscle condition and a facet condition typically share this normal sequence. However, as shown in FIG. 55, the back condition associated with a disc condition typically shows a different sequence in which the maximum RMS voltages for the weighted position is less than that for the flexion position (although still greater than that for the upright position). In addition, some conditions such a chronic exacerbation may have maximum RMS voltages for each of the positions which are compressed with respect to the differences in maximum RMS voltages between positions shown for a normal condition.

In an exemplary embodiment, the system may include software that is operative to automatically determine and output a determined characterization for the sequence of positions in order of low to high maximum RMS voltage. This output may then be manually used to lookup one or more matching back conditions from the table such as shown in FIG. 55 to assist in identifying a back condition diagnosis for the patient.

However, it is to be understood that in alternative exemplary embodiments, the software may be operative to correlate the determined characterization for the sequence of positions for a measurement to corresponding predetermined characterization data stored in the data store for different back conditions to further the identification by the software of a back condition diagnosis for the patient.

With respect to the table shown in FIG. 55, the pattern 508 category corresponds to characteristics of the locations and intensity of muscle activity across the two dimensional area of the back that may be determined from the data monitored by the sensor device for the different back conditions. The relative locations of higher or elevated muscle activity compared to the locations of lower muscle activity across the detection area are shown characterized in terms of uniformity, centrality, symmetry, and organization. Such pattern characterizations can be generally discerned through a visual inspection of the images (e.g. FIG. 3) displayed by the system responsive to the RMS data generated for the array of electrodes in the sensor device. Such visual characterizations of the images produced for a patient may be manually compared to the pattern characterizations shown in a table such as shown in FIG. 55 to assist in identifying a back condition diagnosis for the patient.

However, it is to be understood that in alternative exemplary embodiments, software operating in a computer of the system may use statistical analysis, image processing, expert systems, neural networks, pattern matching, and any other computer processing technique to determine and correlate pattern characterizations for the relative locations and levels of muscle activity acquired from the sensor device. Such determined pattern characterizations can be displayed to a user for use with manually identifying a back condition diagnosis from a table such as shown in FIG. 55. Also, the software may further be operative to correlate the determined pattern characterizations for a measurement to corresponding predetermined characterization data stored in the data store for different back conditions to further the identification by the software of a back condition diagnosis for the patient.

In addition, as discussed previously, differences in patient BMI can influence the magnitude of the maximum RMS voltages determined by the array. Also, the range of RMS voltages produced by an array will vary widely depending on the positions of the patient, as well as the different types of back conditions. Thus the graphical representations (colors, levels of intensity) produced from the maximum RMS voltages for different patients may vary significantly.

To compensate for the differences in the RMS voltage values determined for different types of patients, back conditions, and positions of the patient, an exemplary embodiment of the system may include an input device and/or a software user interface control which allows the technician performing the measurements to adjust how the system correlates RMS voltage values to the different colors and/or grayscale levels of intensity displayed for the graphical representation of the maximum RMS voltages.

For example, the technician may use the input device and/or user interface control of a computer of the system to input an adjustment value. In one exemplary embodiment, the adjustment value may correspond to an offset value or multiplication factor which increases or decreases the ranges of RMS voltage values which are mapped to particular colors and or grayscale levels of intensity.

In another exemplary embodiment, the adjustment value may correspond to a value which is used by the software to visually enhance (through color and/or contrast) relatively higher levels of muscle activity and visually de-emphasize relatively lower levels of muscle activity. In such an embodiment, RMS voltage values below the adjustment value may be displayed with the color or grayscale intensity level corresponding to low levels of muscle activity. Also, RMS voltage values above the adjustment value may be mapped to colors or grayscale intensity levels which span the entire set of colors or grayscale intensity levels corresponding to relatively higher levels of muscle activity. For example, the software may be responsive to an adjustment value of 20 to map all RMS voltage values below 20 to display as blue in a color image, or as white in a grayscale image. The software may also map RMS voltage values at or above the adjustment value of 20 to correspond to displayed colors ranging from green to red for a color image, or displayed levels of intensity ranging from light gray to black for a grayscale image.

In alternative exemplary embodiments, rather than or in addition to an input device or user interface control which inputs an adjustment value used to alter the display of the RMS voltages, the system may include an electrical circuit which amplifies or attenuates the signals generated by the sensor device or another component in the diagnostic system.

As shown in FIG. 55, data associated with patterns in the EMG data acquired for the two dimensional detection area of the sensor device can be used to distinguish between a normal condition, a facet condition, a disc condition, a muscle condition, and other conditions such as sacroiliitis, spondy losis, spondy lolisthesis, spinal stenosis.

Figure 58:
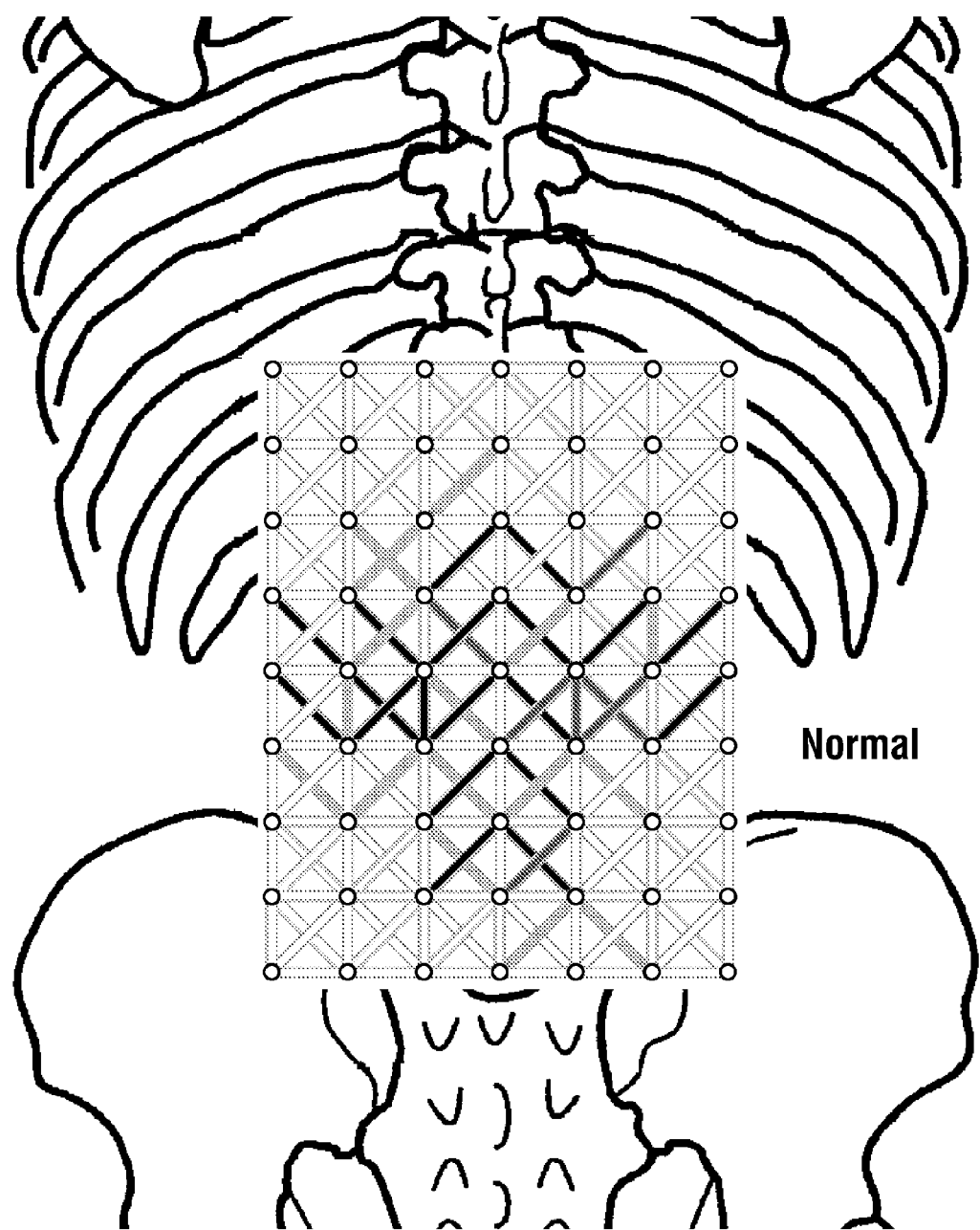
FIG. 58 shows an example of an image generated from EMG data which shows characteristics of a normal back condition.

A normal back condition may be identified when an image of the relative levels of muscle activity in a back for each of the positions of the patient shows a pattern characteristic of "uniform", "central", "symmetrical" and "organized". FIG. 58 shows an example of an image generated by an exemplary embodiment of the diagnostic system which has the characteristics of a normal back condition.

Here the uniform pattern characteristic corresponds to the characteristic in which the spatial patterns across the detection area representative of elevated muscle activity are substantially the same for each position of the patient. The central pattern characteristic corresponds to the presence of grouping of electrode pairs showing an elevated level of muscle activity that is substantially: located in the center of the spine; surrounding the L3,4,5 vertebrae; and balanced on each side (left and right) of the spine. The "symmetry" pattern characteristic corresponds to muscle activity on the left side of the spine that is substantially the mirror image of muscle activity on the right side of the spine. The organized pattern characteristic may correspond to the groupings of elevated muscle activity having a generally central peak that is surrounded by gradually and relatively lower but still elevated levels of muscle activity.

Figure 56:
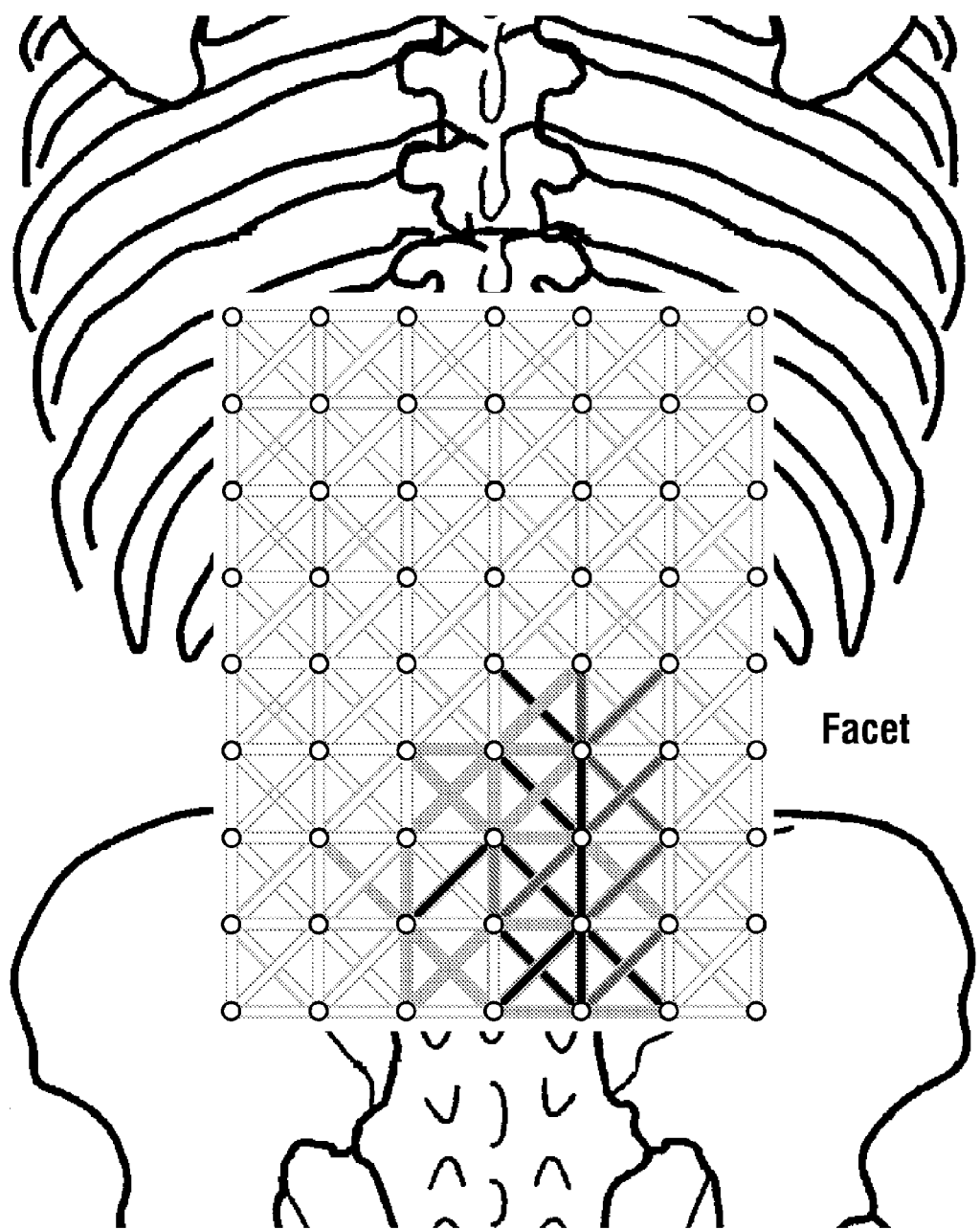
FIG. 56 shows an example of an image generated from EMG data which shows patterns of groupings of elevated muscle activity corresponding to a facet condition.

A facet condition may be identified as a possible back condition when an image of the relative levels of muscle activity in a back for one or more of the positions shows a pattern characteristic of uniform, "unilateral shift" and organized. FIG. 56 shows an example of an image generated by an exemplary embodiment of the diagnostic system which has the characteristics of a facet condition.

Here the uniform and organized pattern characteristics correspond to those previously described for the normal back condition. The unilateral shift pattern characteristic corresponds to a grouping which has a peak of muscle activity that is laterally offset from the longitudinal axis of the vertebral column. The presence of a unilateral shift pattern can be used in the exemplary embodiment to distinguish a normal back condition from a facet condition.

Figure 57:
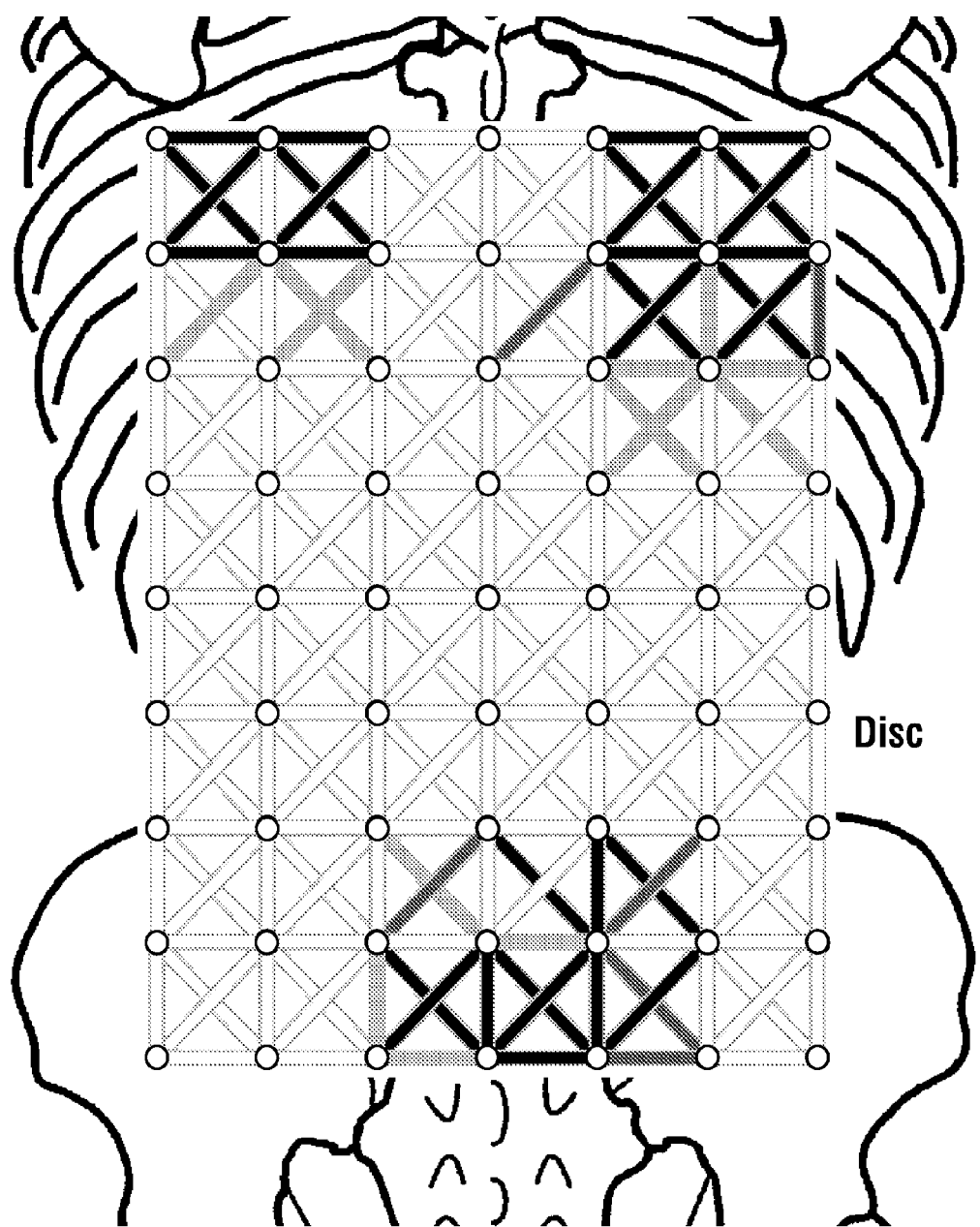
FIG. 57 shows an example of an image generated from EMG data which shows patterns of groupings of elevated muscle activity corresponding to a disc condition.

A disc condition may be identified as a possible back condition when an image of the relative levels of muscle activity in a back for one or more of the positions shows pattern characteristics of uniform, "variable symmetry", "2D or multi-focal", and "accommodation". FIG. 57 shows an example of an image generated by an exemplary embodiment of the diagnostic system which has the characteristics of a disc condition.

Here the uniform, central and symmetry characterization patterns correspond to those described previously for normal or facet conditions. For a disc condition, "variable symmetry" indicates that the images are generally symmetrical with corresponding groupings on each side of the spine that may have different levels of peak activity. The "2D or Multi-focal" characteristic corresponds to the presence of multiple and separated groupings of electrode pairs showing elevated levels of muscle activity which are located about the spine. The "accommodation" characteristic corresponds to the multiple groupings having an arrangement which suggests that secondary muscle groups may be doing the job of primary muscle groups. In exemplary embodiments, the variable symmetry, 2D or multi-focal, and accommodation pattern characteristics can be used to distinguish a disc condition from a normal, facet, muscle, or other condition.

Figure 59:
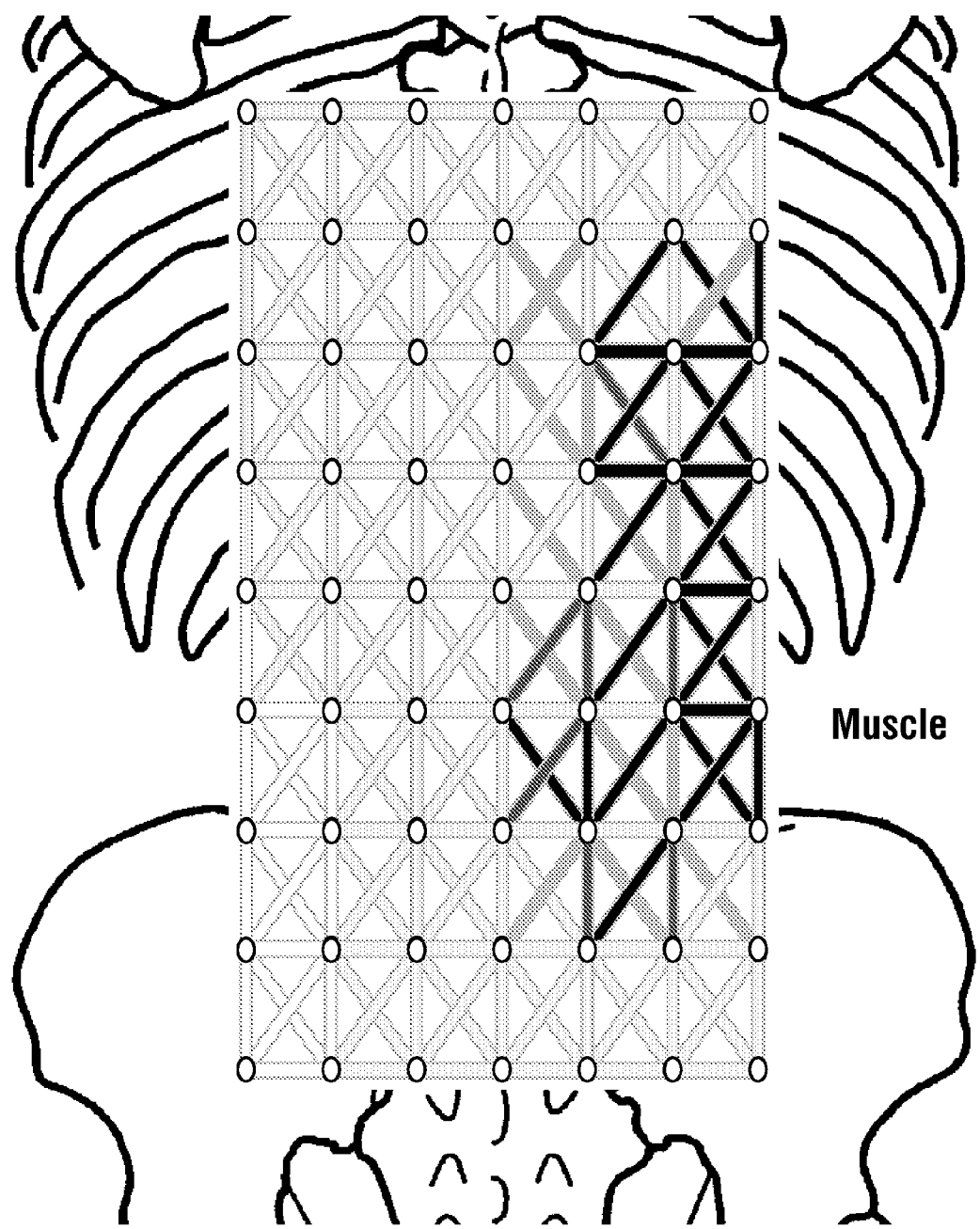
FIG. 59 shows an example of an image generated from EMG data which shows characteristics for a muscle condition.

A muscle condition may be identified as a possible condition when an image of the relative levels of muscle activity in the back for one or more of the positions shows pattern characteristics of "variable uniformity", "unilateral", "asymmetrical", and organized. FIG. 59 shows an example of an image generated by an exemplary embodiment of the diagnostic system which has these characteristics for a muscle condition.

The variable uniformity pattern characteristic corresponds to some positions showing the same pattern (e.g. upright and flexion), but the other position shows increased variability in the pattern (e.g. weighted position). The unilateral pattern characteristic corresponds to one or more groupings of elevated muscle activity which are substantially not located on the longitudinal axis of the vertebral column, but are shifted to one side or the other with respect to the vertebral column. The asymmetrical pattern characteristic corresponds to muscle activity on one side of the spine which is not substantially the mirror image of muscle activity on the right side.

Please note that the original images used to produce FIGS. 56-59 were produced in color. Because black and white copies of such color images made with a copier/scanner do not produce relatively darker levels of grayscale which accurately reflect elevated levels of muscle activity, the original color bars in the image have been redrawn as grayscale bars for FIGS. 56-59. In these drawings, the darker bars correspond to elevated levels of muscle activity and relatively higher levels of RMS voltage compared to the lighter bars.

FIG. 55 shows examples of other conditions that may be identified by characterizing patterns in the images acquired for patients in the described different positions. For example a chronic pain-free condition may have pattern characteristics which may include: uniform, "non-central", asymmetrical, "disorganized", and accommodation. Here the non-central and disorganized pattern characteristics may correspond to an image with generally no significantly elevated groupings of muscle activity. Any groupings that may be visible may be multi-focal or unilateral.

A chronic exacerbation condition may have pattern characteristics corresponding to one or more of the previously described muscle, facet, or disc conditions. The etiology and history of the patient's pain and the possible causes of the pain such as bending, lifting, twisting, or nothing may be used to assist in identifying a precipitating event.

In addition to data representative of the maximum RMS voltage characterization (in the RMS column 504), the determined sequence of positions (in the sequence column 506), and the pattern characteristics (in the pattern column 508) described previously, the table shown in FIG. 55 includes examples of other types of characterization data that may be used to determine a back condition for a patient. For example the balance column 510 and coefficient of variation 512 include additional characteristics that may be used to assist with identifying a particular back condition.

In exemplary embodiments, whether the EMG signals are or are not characterized as balanced may be determined by comparing the RMS voltage for an electrode pair on one side of the image with respect to the vertebral column to the RMS voltage for an electrode pair at the corresponding position on the opposite side of the image with respect to the vertebral column. In an embodiment, corresponding electrode pairs on each side of the image are balanced if their respective RMS voltages are within 20%. If predetermined number of electrode pairs are not balanced, the image for the position may be identified as being unbalanced. In general the normal and facet conditions typically produce balanced images, while the disc and muscle conditions typically produce unbalanced images.

In exemplary embodiments, the coefficient of variation characterization data corresponds to the level of variation between multiple scans for a common position. In an embodiment, variation less than 10 percent may be characterized as normal. For example, for a flexion position, three measurements (or scans) may be taken which produce maximum RMS voltages of 45, 47, 43 respectively with a mean of 45. The variation of the first and third measurements is only 2 away from the mean, and therefore is less than ten percent of the mean. Thus the measurements for the flexion position would be characterized as having a normal coefficient of variation. As shown in FIG. 55, a muscle condition typically is associated with measurements that have a coefficient of variation that is less than 10 percent, while the facet condition typically is associated with measurements that have a coefficient of variation that is greater than 10 percent. Disc conditions may have a coefficient of variation that varies from below or above 10 percent from position to position.

It is to be understood that whether through a manual correlation using a table such as shown in FIG. 55, or through an automatic correlation by software using data stored in a data store corresponding to the table of data shown in FIG. 55, one or more of the described categories of EMG characterization data may be used to correlate or identify a back condition diagnosis for a patient.

In some cases, not all of the EMG characterization data determined for a measurement will point to the same back condition diagnosis. Thus in a further exemplary embodiment, the categories may be ranked in terms of statistical accuracy with identifying the correct back condition. Such ranking data may be included in with a table such as shown in FIG. 55 or be stored in a data store and used either manually or automatically with software to assist in identifying a more likely back condition associated with the patient.

It is to be noted that a patient may have more than one type of back condition, thus conflicting characterizations for different categorizes (e.g. RMS, sequence, pattern, etc.) or for different positions (e.g. upright, flexion, weighted) may be used to correlate more than one type of back condition with a patient.

Although certain embodiments have been disclosed and specifically described herein, these embodiments are for purposes of illustration and are not meant to limit the present invention. Upon review of this specification, certain improvements, modifications, adaptations and variations upon the methods and apparatus disclosed which do not depart from the spirit of the present invention will immediately become apparent. Accordingly, reference should be had to the appended claims in order to ascertain the true scope of the present invention.

For example, the apparatus might be applied to areas of human anatomy other than the lower back musculature, most obviously to mid-back, upper back or neck areas. Still further, it would be feasible to apply the teachings of exemplary embodiments to the extremities of the human patient or even to areas of the head. Exemplary embodiments may also be applied to the analysis of signals from other types of sensors and the techniques described herein used in the diagnosis and treatment of other conditions. While the exemplary form is used in the diagnosis of conditions in human beings, the techniques and apparatus of exemplary embodiments may also find applicability in diagnostic and treatment activities related to patients which comprise other living organisms.

In addition, the teachings described herein may also be used for detecting the position and intensity of other electrical signals within areas of the anatomy of a living body. Various organs and systems are known to produce such electrical signals. The analysis of such signals and their correlation may provide useful information for diagnosis and treatment.

In addition, systems of the exemplary embodiments may be modified to provide therapeutic benefit as well as to serve a diagnostic function. For example electrode arrays may be used to provide electrical stimulus selectively in areas corresponding to the electrodes. Such electrical stimulus may be used to treat muscle or other disorders. By way of example an electrode array may be used to determine the identities of muscles which are the source of a spasmodic or pain condition in the manner previously discussed. Once such muscles have been identified appropriate electrical circuitry may be provided to deliver electrical stimulation selectively so as to treat the underlying muscular structures. Alternative approaches and techniques may be used based on the nature of the underlying conditions being detected and the appropriate method of treatment.

The previous described embodiments of the diagnostic system have used a sensor device corresponding to an EMG electrode array that is applied adjacent of the skin surface of the patient. However, it is to be understood that in alternative embodiments of the described methods for diagnosing back conditions or other conditions responsive to electrical signals acquired from the body of a patient, other types of sensor devices may be used such as the invasive sensors used with electromyography and fine-wire electromyography.

Computer software instructions used in operating the EMG diagnostic system and method and associated computers may be loaded from computer readable media or articles of various types into the respective computers. Such computer software may be included on and loaded from one or more articles such as diskettes, compact disks (CDs) and DVDs. Such software may also be included on articles such as hard disk drives, tapes, flash memory devices, or ready only memory devices. Other articles which include data representative of the instructions for operating computers in the manner described herein are suitable for use in achieving operation of the EMG diagnostic system in accordance with embodiments described herein The embodiments of the EMG diagnostic system described herein have been described with reference to particular software components and features. Other embodiments may include other or different software components which provide similar functionality.

Thus the method and apparatus of one or more of the embodiments described herein achieve one or more of the above stated objectives, eliminates difficulties encountered in the use of prior devices and systems, solves problems and attains the desirable results described herein.

In the foregoing description certain terms have been used for brevity, clarity and understanding. However no unnecessary limitations are to be implied therefrom because such terms are for descriptive purposes and are intended to be broadly construed. Moreover the descriptions and illustrations herein are by way of examples and the invention is not limited to the details shown and described.

In the following claims any feature that is described as a means for performing a function shall be construed as encompassing any means capable of performing the recited function and shall not be limited to the particular means shown in the foregoing description or mere equivalents. The description of the exemplary embodiment included in the Abstract included herewith shall not be deemed to limit the invention to features described therein.

Having described the features, discoveries and principles of the invention, the manner in which it is constructed and operated and the advantages and useful results attained; the new and useful structures, devices, elements, arrangements, parts, combinations, systems, equipment, operations and relationships are set forth in the appended claims.

We claim:

1. A method comprising:
   a) through operation of at least one processor, determining electromyographic (EMG) data for a patient responsive to EMG signals detected from a detection area on a back of the patient using an EMG sensor device in operative connection with the at least one processor;
   b) determining whether the EMG data for the patient determined in (a) is indicative of the patient having either:
      i) a facet condition and not a disc condition; or
      ii) a disc condition and not a facet condition;
   responsive to a comparison between the EMG data for the patient and predetermined data representative of characteristics in EMG data that distinguish between the facet condition and the disc condition.

2. The method according to claim 1, wherein (b) includes comparing the EMG data for the patient to the predetermined data, wherein the predetermined data includes data which is usable to determine that EMG data is indicative of which one of the facet condition, the disc condition, and a muscle condition, wherein indicia corresponding to the predetermined data is displayed on an object.

3. The method according to claim 2, wherein (b) includes determining, responsive to comparing the EMG data for the patient to the predetermined data, that the patient is associated with either the facet condition or the disc condition, and not the muscle condition.

4. The method according to claim 1, wherein (b) is carried out through operation of the at least one processor, further comprising:
   c) through operation of the at least one processor, outputting through at least one display device in operative connection with the at least one processor, indicia indicating that the patient is associated with which one of the facet condition or the disc condition determined in (b).

5. The method according to claim 1, comprising:
   determining a relative position of at least one grouping of portions in the detection area corresponding to a higher level of muscle contraction relative adjacent portions in the detection area.

6. The method according to claim 5, wherein prior to (b) further comprising:
   (c) through operation of the at least one processor, displaying through a display device in operative connection with the processor, at least one image representative of the detection area, wherein the at least one image shows the relative position of the at least one grouping in the detection area corresponding to the relatively higher level of muscle contraction.

7. The method according to claim 6, further comprising: adjusting the at least one image displayed in (c) to enable the relative position of the at least one grouping to be more visually distinguishable in the at least one image from the adjacent portions.

8. The method according to claim 1, wherein in (a) the sensor device comprises a flexible electrode array comprised of a plurality of electrodes.

9. A method comprising:
   a) through operation of at least one processor, determining electromyographic (EMG) data for a patient responsive to EMG signals detected from a detection area on a back of the patient using an EMG sensor device in operative connection with the at least one processor;
   b) determining from the EMG data for the patient determined in (a), relative positions of at least two to three spaced apart groupings of portions in the detection area corresponding to relatively higher levels of muscle contraction relative to further portions in the detection area between the two to three groupings;
   c) determining whether the EMG data for the patient determined in (a) corresponds to a facet condition or a disc condition responsive to predetermined data representative of characteristics in EMG data that distinguish between the facet condition and the disc condition, including determining that the groupings determined in (b) correspond to predetermined data associated with the disc condition.

10. A method comprising:
    a) through operation of at least one processor, determining electromyographic (EMG) data for a patient responsive to EMG signals detected from a detection area on a back of the patient using an EMG sensor device in operative connection with the at least one processor;
    b) determining from the EMG data for the patient determined in (a), relative positions of three spaced apart groupings of portions in the detection area corresponding to relatively higher levels of muscle contraction relative to further portions in the detection area between the three spaced apart groupings, wherein two of the three determined groupings are generally horizontally aligned and are respectively located on opposed sides of the spine of the patient, wherein a third one of the three determined groupings traverses a vertebral column of the patient and is located vertically lower than the two horizontally aligned groupings;
    c) determining whether the EMG data for the patient determined in (a) corresponds to a facet condition or a disc condition responsive to predetermined data representative of characteristics in EMG data that distinguish between the facet condition and the disc condition, including determining that the groupings determined in (b) correspond to predetermined data associated with the disc condition.

11. A method comprising:
    a) through operation of at least one processor, determining electromyographic (EMG) data for a patient responsive to EMG signals detected from a detection area on a back of the patient using an EMG sensor device in operative connection with the at least one processor;
    b) determining from the EMG data for the patient determined in (a), a presence of only a single grouping of portions in the detection area indicative of relatively higher levels of muscle contraction relative to remaining portions in the detection area, wherein the single grouping traverses a vertebral column of the patient, wherein a center of the single grouping is spaced laterally from a longitudinal axis of the vertebral column of the patient;
    c) determining whether the EMG data for the patient determined in (a) corresponds to a facet condition or a disc condition responsive to predetermined data representative of characteristics in EMG data that distinguish between the facet condition and the disc condition, including determining that the grouping determined in (b) corresponds to predetermined data associated with the facet condition.

12. A method comprising:
a) through operation of at least one processor, determining electromyographic (EMG) data for a patient responsive to EMG signals detected from a detection area on a back of the patient, using an EMG sensor device in operative connection with the at least one processor, including determining data representative of at least one maximum root mean square (RMS) voltage associated with the EMG signals;
b) determining whether the EMG data for the patient determined in (a) corresponds to a facet condition or a disc condition responsive to predetermined data representative of characteristics in EMG data that distinguish between the facet condition and the disc condition, including determining whether the data representative of the at least one maximum RMS voltage is above, below, or within at least one range of predetermined normal maximum RMS voltages.

13. The method according to claim 12, wherein the at least one range of predetermined normal maximum RMS voltages is selected responsive to at least one of percent ideal body weight and gender of the patient from a plurality of ranges of predetermined normal maximum RMS voltages corresponding respectively to data representative of at least one of different ranges of percent ideal body weight and different genders.

14. The method according to claim 13, wherein (b) includes determining that the EMG data for the patient is indicative of the facet condition responsive to determining that the data representative of the at least one maximum RMS voltage is below the at least one range of predetermined normal maximum RMS voltages.

15. The method according to claim 13, wherein (b) includes determining that the EMG data for the patient is indicative of the disc condition responsive to determining that the data representative of the at least one maximum RMS voltage is above the at least one range of predetermined normal maximum RMS voltages.

16. A method comprising:
a) detecting electromyographic (EMG) signals from a detection area on a back of a patient when the patient is in at least three different positions using an EMG sensor device in operative connection with at least one processor;
b) through operation of the at least one processor, determining EMG data for the patient responsive to the EMG signals detected in (a), including determining data representative of maximum root mean square (RMS) voltage associated with the EMG signals for each of the at least three different positions;
c) determining a sequence for the at least three different positions, which sequence corresponds to a sequence of the respective maximum RMS voltages determined for the at least three positions ordered by magnitude;
d) determining whether the EMG data for the patient determined in (b) corresponds to a facet condition or a disc condition responsive to a comparison between the sequence determined in (c) and at least one predetermined sequence that distinguishes between the facet condition and the disc condition.

17. The method according to claim 16, wherein (a) includes detecting EMG signals while the patient is standing: in a first position with the back of the patient in a generally vertical orientation; in a second position with the back of the patient bent forward with respect to the generally vertical orientation; and in a third position with the arms of the patient held out in front of the patient while holding weights, wherein (d) includes determining that the EMG data for the patient is indicative of the disc condition responsive to determining that the sequence determined in (c) for the at least three different positions corresponding to lowest to highest maximum RMS voltage for the respective positions corresponds to an order of: the first position, the third position, and the second position.

18. The method according to claim 16, wherein (a) includes detecting EMG signals while the patient is standing: in a first position with the back of the patient in a generally vertical orientation; in a second position with the back of the patient bent forward with respect to the generally vertical orientation; and in a third position with the arms of the patient held out in front of the patient while holding weights, wherein (d) includes determining that the EMG data for the patient is indicative of the facet condition responsive to determining that the sequence determined in (c) for the at least three different positions corresponding to lowest to highest maximum RMS voltage for the respective positions corresponds to an order of: the first position, the second position, and the third position.

19. A method comprising:
a) detecting electromyographic (EMG) signals from a detection area on a back of a patient using an EMG sensor device;
b) determining through operation of at least one processor, EMG data for the patient responsive to the EMG signals detected in (a);
c) comparing the EMG data for the patient to predetermined EMG data, wherein the predetermined EMG data correlates a plurality of back conditions to respective sets of features of EMG data, wherein the back conditions correlated in the predetermined EMG data include both a facet condition and a disc condition;
d) determining whether the EMG data for the patient is indicative of the facet condition and not the disc condition or the disc condition and not the facet condition, responsive to (c).

20. The method according to claim 19, wherein the at least one processor is in operative communication with at least one data store, wherein the at least one data store includes the predetermined EMG data stored therein, wherein the back conditions correlated in the predetermined EMG data include the facet condition, the disc condition, and a muscle condition;
wherein (a) includes detecting the EMG signals from the patient when the patient is in at least three different positions including at least one of: in a first position with the back of the patient in a generally vertical orientation; in a second position with the back of the patient bent forward with respect to the generally vertical orientation; and in a third position with the arms of the patient held out in front of the patient while holding weights;
wherein (c) is carried out through operation of the at least one processor,
wherein (b) includes at least one of:
i) determining the relative positions of at least one grouping of portions in the detection area corresponding to relatively higher levels of muscle contraction relative further portions in the detection area adjacent the at least one grouping;
ii) determining data representative of at least one maximum RMS voltage associated with the EMG signals and determining whether the data representative of the at least one maximum RMS voltage is above, below, or within at least one range of predetermined normal maximum RMS voltages stored in the at least one data store;

iii) determining data representative of maximum RMS voltage associated with the EMG signals for each of the at least three different positions, determining a sequence for the at least three different positions, which sequence corresponds to a sequence of the respective maximum RMS voltages determined for the at least three positions ordered by magnitude;

wherein in (c) the predetermined EMG data stored in the at least one data store includes at least one of:

data which associates the facet condition with features of EMG data representative of the presence of only a single grouping of portions in the detection area indicative of relatively higher levels of muscle contraction relative remaining portions in the detection area, wherein the single grouping traverses the vertebral column of the patient, wherein a center of the single grouping is spaced laterally from a longitudinal axis of the vertebral column of the patient;

data which associates the disc condition with features of EMG data representative of the relative positions of at least two to three spaced apart groupings of portions in the detection area corresponding to relatively higher levels of muscle contraction relative further portions in the detection area between the two to three groupings;

data which associates the facet condition with features of EMG data representative of the at least one maximum RMS voltage being below the at least one range of predetermined normal maximum RMS voltages;

data which associates at least one of the disc condition or a muscle condition with features of EMG data representative of the at least one maximum RMS voltage being above the at least one range of predetermined normal maximum RMS voltages;

data which associates at least one of the facet condition and the muscle condition with features of EMG data representative of the sequence for the at least three different positions corresponding to lowest to highest maximum RMS voltage for the respective positions corresponding to an order of: the first position, the second position, and the third position;

data which associates the disc condition with features of EMG data representative of the sequence for the at least three different positions corresponding to lowest to highest maximum RMS voltage for the respective positions corresponding to an order of: the first position, the third position, and the second position;

further comprising:

e) outputting through at least one display device in operative connection with the at least one processor, indicia indicative of the determination in (d).

21. At least one non-transitory computer readable media including computer executable instructions operative to cause at least one computer to carry out a method comprising:

a) determining electromyographic (EMG) data for a patient responsive to EMG signals detected from a detection area on a back of the patient using an EMG sensor device;

b) comparing the EMG data for the patient determined in (a) to predetermined EMG data, wherein the predetermined EMG data defines characteristics in EMG data determined from EMG signals that are usable to distinguish between the facet condition and the disc condition; and c) responsive to (b), determining whether the EMG data for the patient determined in (a) is indicative of either:
i) facet condition and not a disc condition; or
ii) a disc condition and not a facet condition.

22. At least one non-transitory computer readable media including computer executable instructions operative to cause at least one computer to carry out a method comprising:

a) through operation of the at least one computer, determining electromyographic (EMG) data for a patient responsive to EMG signals detected from a detection area on a back of the patient using an EMG sensor device;

b) through operation of the at least one computer, determining whether the EMG data determined in (a) is indicative of either:
i) a facet condition and not a disc condition; or
ii) a disc condition and not a facet condition;

responsive to predetermined data representative of characteristics in EMG data that distinguish between a facet condition and a disc condition; and c) through operation of the at least one computer, outputting through a display device, indicia indicative of the determination made in (b).

23. The media according to claim 22, wherein (b) includes determining that the EMG data for the patient is indicative of a facet condition and not a disc condition, responsive to the at least one computer determining that the EMG data indicates the presence of a single grouping of portions in the detection area corresponding to relatively higher levels of muscle contraction relative to remaining portions in the detection area, wherein the single grouping traverses the vertebral column of the patient, wherein a center of the single grouping is spaced laterally from a longitudinal axis of the vertebral column of the patient.

24. The media according to claim 22, wherein (b) includes determining that the EMG data for the patient is indicative of a disc condition and not a facet condition, responsive to the at least one computer determining that the EMG data indicates the presence of at least two to three spaced apart groupings of portions in the detection area corresponding to relatively higher levels of muscle contraction relative to further portions in the detection area between the two to three groupings.

25. The media according to claim 22, wherein (b) includes determining that the EMG data for the patient is indicative of a disc condition and not a facet condition, responsive to the at least one computer determining that the EMG data indicates the presence of three spaced apart groupings of portions in the detection area corresponding to relatively higher levels of muscle contraction relative to further portions in the detection area between the three spaced apart groupings, wherein two of the three determined groupings are generally horizontally aligned and are respectively located on opposed sides of the spine of the patient, wherein a third one of the three determined groupings traverses a vertebral column of the patient and is located vertically lower than the two horizontally aligned groupings.

26. The media according to claim 22, wherein in (a) the EMG data is determined from EMG signals from the patient when the patient is in at least three different positions, further comprising prior to (b):

d) through operation of the at least one computer, determining data representative of maximum RMS voltage associated with the EMG signals for each of the at least three different positions;

e) determining a sequence for the at least three different positions, which sequence corresponds to the at least three different positions being in an order from lowest magnitude to highest magnitude for the corresponding respective maximum RMS voltages determined for the at least three positions;

wherein the determination in (b) is carried out responsive to the sequence determined in (e), wherein the predetermined data associates the facet condition and the disc condition with respectively different orders of the at least three different positions for the sequence.

27. The media according to claim 26, wherein in (a) the at least three positions of the patient include: in a first position with the back of the patient in a generally vertical orientation; in a second position with the back of the patient bent forward with respect to the generally vertical orientation; and in a third position with the arms of the patient held out in front of the patient while holding weights.

28. The media according to claim 27, wherein (b) includes determining that the EMG data for the patient is indicative of a facet condition and not a disc condition, responsive to the at least one computer determining that the sequence determined in (e) corresponds to predetermined data corresponding to an order of: the first position, the second position, and the third position.

29. The media according to claim 27, wherein (b) includes determining that the EMG data for the patient is indicative of a disc condition and not a facet condition, responsive to the at least one computer determining that the sequence determined in (e) corresponds to predetermined data corresponding to an order of: the first position, the third position, and the second position.

30. A method comprising:
a) through operation of at least one computer, determining electromyographic (EMG) data for a patient responsive to EMG signals detected from a detection area on a back of the patient using an EMG sensor device; and
b) determining whether the EMG data determined in (a) is indicative of either:
  i) a facet condition and not a disc condition; or
  ii) a disc condition and not a facet condition;
when compared to predetermined data representative of characteristics in EMG data that distinguish between a facet condition and a disc condition.

* * * * *